US009198675B2

(12) United States Patent
Nelson et al.

(10) Patent No.: US 9,198,675 B2
(45) Date of Patent: Dec. 1, 2015

(54) RECIPROCATING SURGICAL INSTRUMENT

(71) Applicants:IMDS Corporation, Providence, UT (US); Keith J. Nelson, Logan, UT (US)

(72) Inventors: Keith J. Nelson, Logan, UT (US); Daniel F. Justin, Orlando, FL (US); Douglas M. Lorang, San Jose, CA (US); Andrew R. Fauth, River Heights, UT (US); Daniel J. Triplett, Providence, UT (US); Trevor K. Lewis, Lehi, UT (US); Gavin Sontag, Fort Worth, TX (US); Nathan D. Hansen, Hyde Park, UT (US); Karen E. Mohr, Salt Lake City, UT (US); Joseph Q. Marietta, Kalamazoo, MI (US); M. Mary Sinnott, Logan, UT (US)

(73) Assignees: IMDS LLC, Providence, UT (US); Keith J. Nelson, Logan, UT (US)

( * ) Notice: Subject to any disclaimer, the term of this patent is extended or adjusted under 35 U.S.C. 154(b) by 212 days.

(21) Appl. No.: 13/865,909

(22) Filed: Apr. 18, 2013

(65) Prior Publication Data
US 2013/0304070 A1 Nov. 14, 2013

Related U.S. Application Data

(63) Continuation-in-part of application No. 13/231,121, filed on Sep. 13, 2011, now Pat. No. 9,033,986, which is a continuation-in-part of application No. 13/102,351, filed on May 6, 2011, now abandoned, (Continued)

(51) Int. Cl.
*A61B 17/00* (2006.01)
*A61B 17/16* (2006.01)
(Continued)

(52) U.S. Cl.
CPC ......... *A61B 17/1659* (2013.01); *A61B 17/1624* (2013.01); *A61B 18/148* (2013.01);
(Continued)

(58) Field of Classification Search
CPC .................... A61B 17/1659; A61B 17/32002; A61B 2017/320028; A61B 2017/320032; A61B 17/1668; A61B 17/1671; A61B 2017/0046; A61B 2017/0477; A61B 18/148; A61B 17/1624; A61B 2218/007; A61B 2018/00196; A61B 17/1628; A61B 17/1604; A61B 17/320783; A61B 17/1644; A61B 2018/1861; A61B 17/162; A61M 1/0008
See application file for complete search history.

(56) References Cited

U.S. PATENT DOCUMENTS 3,596,525 A 8/1971 Niesz
3,884,238 A 5/1975 O'Malley et al.
(Continued)

FOREIGN PATENT DOCUMENTS

WO WO 93/11910 A1 6/1993
WO WO 99/13789 A2 3/1999
(Continued)

OTHER PUBLICATIONS

Arthoscopic Smith & Nephew Dyonics & Powermax Elite., http://global.smith-nephew.com/us/DYINICS.sub (2013).
(Continued)

*Primary Examiner* — Christopher Beccia
*Assistant Examiner* — Diana S Jones
(74) *Attorney, Agent, or Firm* — Craig Buschmann; Ryan L. Marshall; Brinks Gilson & Lione

(57) ABSTRACT

A surgical rasping and/or shaving system functions in multiple orthopedic applications, including but not limited to shoulder, knee, hip, wrist, ankle, spinal, or other joint procedures. The system may comprise a tissue removal member with a rasping and/or shaving head which may be low profile and offer a flat cutting/rasping/shaving surface, or with a cutting head with at least one cutting edge. The tissue removal member is configured to be driven by an attached hub that translates a rotational movement into a reciprocating motion. Suction for removal of bone fragments or other tissues is provided through an opening spaced apart from or adjacent to the rasping surface. A radiofrequency ablation (RF) electrode may be carried on the system to provide ablation or coagulation of soft tissues.

18 Claims, 78 Drawing Sheets

Related U.S. Application Data which is a continuation-in-part of application No. 12/765,451, filed on Apr. 22, 2010, now Pat. No. 8,617, 164.

(60) Provisional application No. 61/245,487, filed on Sep. 24, 2009, provisional application No. 61/382,750, filed on Sep. 14, 2010, provisional application No. 61/382,758, filed on Sep. 14, 2010, provisional application No. 61/382,772, filed on Sep. 14, 2010, provisional application No. 61/332,308, filed on May 7, 2010, provisional application No. 61/332,795, filed on Sep. 14, 2010, provisional application No. 61/635,196, filed on Apr. 18, 2012.

(51) Int. Cl.
*A61B 18/14* (2006.01)
*A61M 1/00* (2006.01)
*A61B 17/32* (2006.01)
*A61B 17/3207* (2006.01)
*A61B 18/00* (2006.01)
*A61B 18/18* (2006.01)

(52) U.S. Cl.
CPC .......... *A61B 17/162* (2013.01); *A61B 17/1604* (2013.01); *A61B 17/1628* (2013.01); *A61B 17/1644* (2013.01); *A61B 17/32002* (2013.01); *A61B 17/320783* (2013.01); *A61B 2017/320008* (2013.01); *A61B 2017/320028* (2013.01); *A61B 2017/320032* (2013.01); *A61B 2018/00196* (2013.01); *A61B 2018/1861* (2013.01); *A61B 2217/005* (2013.01); *A61B 2218/007* (2013.01); *A61M 1/008* (2013.01)

(56) References Cited

U.S. PATENT DOCUMENTS

| | | | |
|---|---|---|---|
| 4,108,182 A | 8/1978 | Hartman et al. | |
| 4,210,146 A | 7/1980 | Banko | |
| 4,246,902 A | 1/1981 | Martinez | |
| 4,314,560 A | 2/1982 | Helfgott et al. | |
| 4,530,357 A | 7/1985 | Pawlaski et al. | |
| 4,589,414 A | 5/1986 | Yoshida et al. | |
| 4,625,725 A | 12/1986 | Davison et al. | |
| 4,662,371 A | 5/1987 | Whipple et al. | |
| 4,700,702 A | 10/1987 | Nilsson | |
| 4,727,941 A | 3/1988 | Fulton | |
| 4,728,319 A | 3/1988 | Masch | |
| 4,936,845 A | 6/1990 | Stevens | |
| 5,152,744 A | 10/1992 | Krause et al. | |
| 5,185,934 A | 2/1993 | Tilman | |
| 5,285,816 A | 2/1994 | Herlihy | |
| 5,364,395 A | 11/1994 | West, Jr. | |
| 5,387,215 A | 2/1995 | Fisher | |
| 5,403,276 A | 4/1995 | Schechter et al. | |
| 5,411,513 A | 5/1995 | Ireland et al. | |
| 5,437,630 A | 8/1995 | Daniel et al. | |
| 5,490,860 A | 2/1996 | Middle et al. | |
| 5,527,331 A | 6/1996 | Kresch et al. | |
| 5,540,693 A | 7/1996 | Fisher | |
| 5,593,415 A | 1/1997 | Adrian | |
| 5,632,759 A | 5/1997 | Rexroth | |
| 5,643,304 A | 7/1997 | Schechter et al. | |
| 5,669,876 A | 9/1997 | Schechter et al. | |
| 5,685,840 A | 11/1997 | Schechter et al. | |
| 5,707,374 A | 1/1998 | Schmidt | |
| 5,810,860 A | 9/1998 | Adrian | |
| 5,811,049 A | 9/1998 | Kashiwagi | |
| 5,814,049 A | 9/1998 | Pratt et al. | |
| 5,817,050 A | 10/1998 | Klein | |
| 5,833,643 A | 11/1998 | Ross et al. | |
| 5,904,681 A | 5/1999 | West, Jr. | |
| 5,925,055 A | 7/1999 | Adrian et al. | |
| 5,957,881 A | 9/1999 | Peters et al. | |
| 6,042,593 A | 3/2000 | Storz et al. | |
| 6,048,345 A | 4/2000 | Berke et al. | |
| 6,083,228 A | 7/2000 | Michelson | |
| 6,193,715 B1 | 2/2001 | Wrublewski et al. | |
| 6,368,324 B1 | 4/2002 | Dinger et al. | |
| 6,451,017 B1 | 9/2002 | Moutafis et al. | |
| 6,451,022 B2 | 9/2002 | Dinger et al. | |
| 6,537,280 B2 | 3/2003 | Dinger et al. | |
| 6,595,996 B2 | 7/2003 | Dinger et al. | |
| 6,610,066 B2 | 8/2003 | Dinger et al. | |
| 6,635,060 B2 | 10/2003 | Hanson et al. | |
| 6,751,875 B2 | 6/2004 | Jones | |
| 6,827,725 B2 | 12/2004 | Batchelor et al. | |
| 7,070,604 B1 | 7/2006 | Garito et al. | |
| 7,226,459 B2 | 6/2007 | Cesarini et al. | |
| 7,390,330 B2 | 6/2008 | Harp | |
| 7,510,563 B2 | 3/2009 | Cesarini et al. | |
| 7,569,057 B2 | 8/2009 | Liu et al. | |
| 7,666,186 B2 | 2/2010 | Harp | |
| 7,837,700 B2 | 11/2010 | Harp | |
| 7,883,476 B2 | 2/2011 | Miller et al. | |
| 7,922,737 B1 | 4/2011 | Cesarini et al. | |
| 2001/0037114 A1 | 11/2001 | Dinger et al. | |
| 2001/0039427 A1 | 11/2001 | Dinger et al. | |
| 2004/0049217 A1 | 3/2004 | Ross et al. | |
| 2005/0065529 A1 | 3/2005 | Liu et al. | |
| 2006/0026117 A1 | 2/2006 | Raman et al. | |
| 2006/0058732 A1 | 3/2006 | Harp | |
| 2006/0079919 A1 | 4/2006 | Harp | |
| 2006/0089633 A1 | 4/2006 | Bleich et al. | |
| 2006/0108342 A1 | 5/2006 | Fang | |
| 2006/0129159 A1 | 6/2006 | Lee | |
| 2006/0129160 A1 | 6/2006 | Liu et al. | |
| 2006/0161189 A1 | 7/2006 | Harp | |
| 2006/0200153 A1 | 9/2006 | Harp | |
| 2006/0200154 A1 | 9/2006 | Harp | |
| 2006/0200155 A1* | 9/2006 | Harp .............................. 606/85 |
| 2006/0206117 A1 | 9/2006 | Harp | |
| 2006/0224160 A1 | 10/2006 | Trieu et al. | |
| 2006/0259055 A1 | 11/2006 | Thorne et al. | |
| 2007/0016238 A1 | 1/2007 | Marietta | |
| 2007/0021766 A1 | 1/2007 | Belagali et al. | |
| 2007/0208353 A1 | 9/2007 | Shadduck | |
| 2008/0021487 A1 | 1/2008 | Heisler | |
| 2008/0047143 A1 | 2/2008 | Quan et al. | |
| 2008/0058820 A1 | 3/2008 | Harp | |
| 2008/0103446 A1 | 5/2008 | Torrance et al. | |
| 2009/0177202 A1 | 7/2009 | May et al. | |

FOREIGN PATENT DOCUMENTS

| | | |
|---|---|---|
| WO | WO 03/037194 A1 | 5/2003 |
| WO | WO 03/053278 A2 | 7/2003 |
| WO | WO 2004/002331 A1 | 1/2004 |
| WO | WO 2004/028351 A2 | 4/2004 |
| WO | WO 2005/009213 A2 | 2/2005 |
| WO | WO 2005/020826 A1 | 3/2005 |
| WO | WO 2006/047598 A1 | 5/2006 |
| WO | WO 2006/108342 A1 | 10/2006 |
| WO | WO 2009/005458 A1 | 1/2009 |

OTHER PUBLICATIONS

Arthrex CoolCut, Sabertooth and Excaliber, Clearcut (Burrs), https://www.arthrex.com/innovations/top-left.cfm?adid=27 (2008).
Arthrex; Product Brochure, pp. 1-2 (2008).
Arthronet; Product Brochure, Cat.sub.—D.sub.—R00 / Seite 1-15 (2003).
CONMED Linvatec; ReAct Shaver, Product Brochure, CBR 0038 pp. 1-2 (Sep. 2008).
CONMED Linvatec Product Catalog 6, Rasp (2007).
CONMED; Product Brochure, CBR 0030 Rev.4, p. 1 (Jun. 2008).
CONMED; Product Brochure, CCA 9030, pp. 1-102 (Dec. 2006).
European Search Report for related European Application No. 10819175.0, mailed Oct. 17, 2014 (7 pages).

(56) References Cited

OTHER PUBLICATIONS

FMS (DePuy Mltek, Inc) Shavers and Burrs, http://www.depuymitekfms.com/products/shavers (2008).
Myarthrex Product Brochures; LR06551; Arthrex.com (2008).
PCT International Search Report and Written Opinion for related Application No. PCT/US2010/032081, mailed Feb. 1, 2011.
PCT International Preliminary Report on Patentability for related Application No. PCT/US2010/032081, mailed Apr. 5, 2012.
PCT International Search Report and Written Opinion for related Application No. PCT/US2011/035537, mailed Jul. 12, 2011.
PCT International Preliminary Report on Patentability for related Application No. PCT/US2011/035537, mailed Nov. 22, 2012.
PCT International Search Report and Written Opinion for related Application No. PCT/US2011/051415, mailed Mar. 13, 2012.
PCT International Preliminary Report on Patentability for related Application No. PCT/US2011/051415, mailed Mar. 28, 2013.
Rhinoplasty, The, http:www.therhinoplastycenter.com/poweredrasp.html, pp. 1-4, (May 20, 2009).
Vokurka, J.; Shaver (Micro Debridor) in Otorhinolarynoglogy, International Congress Series 1240:1411-1415 (2003).

* cited by examiner

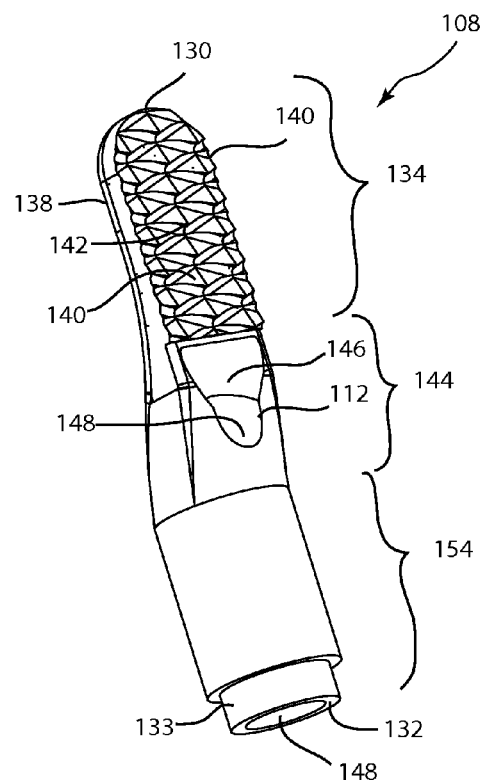
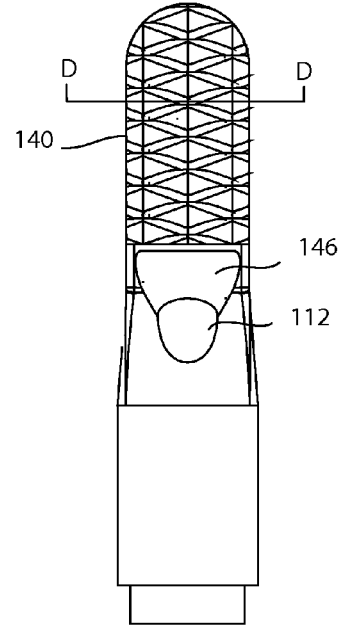
Fig. 3A  Fig. 3B
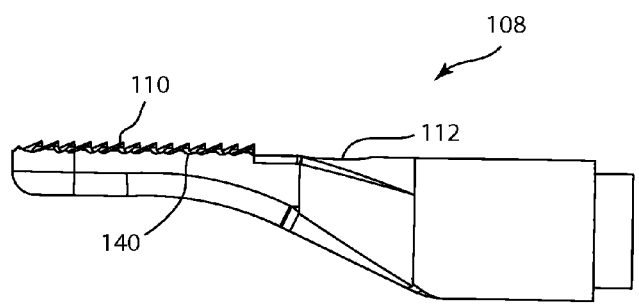
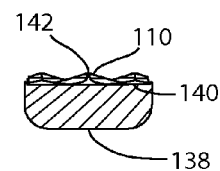
Fig. 3C  Fig. 3D

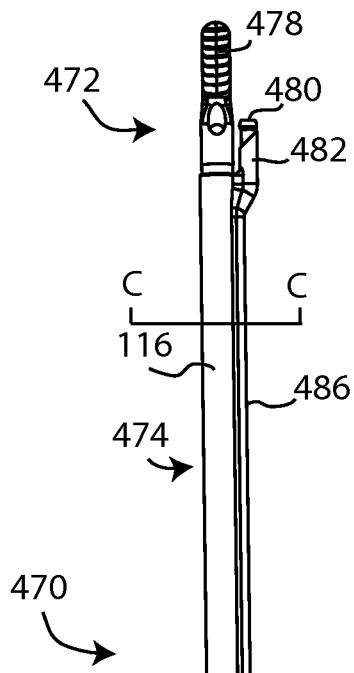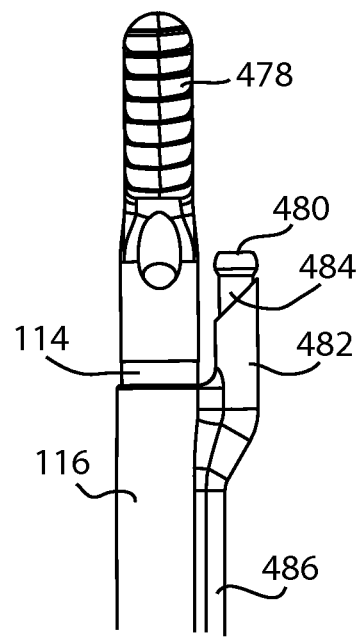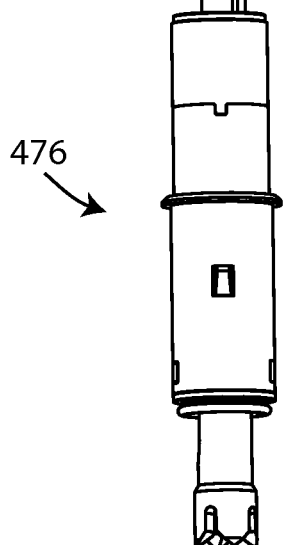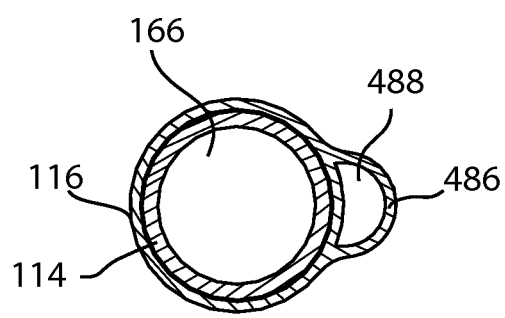
Fig. 25A
Fig. 25B
Fig. 25C

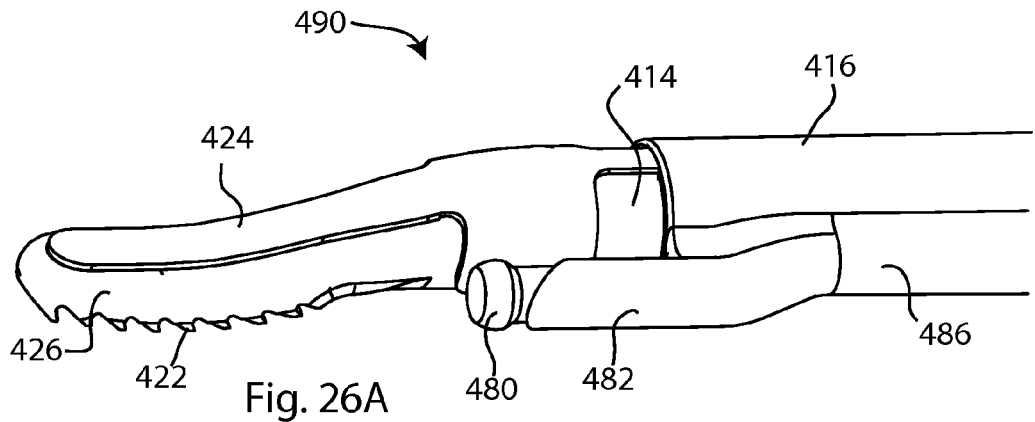
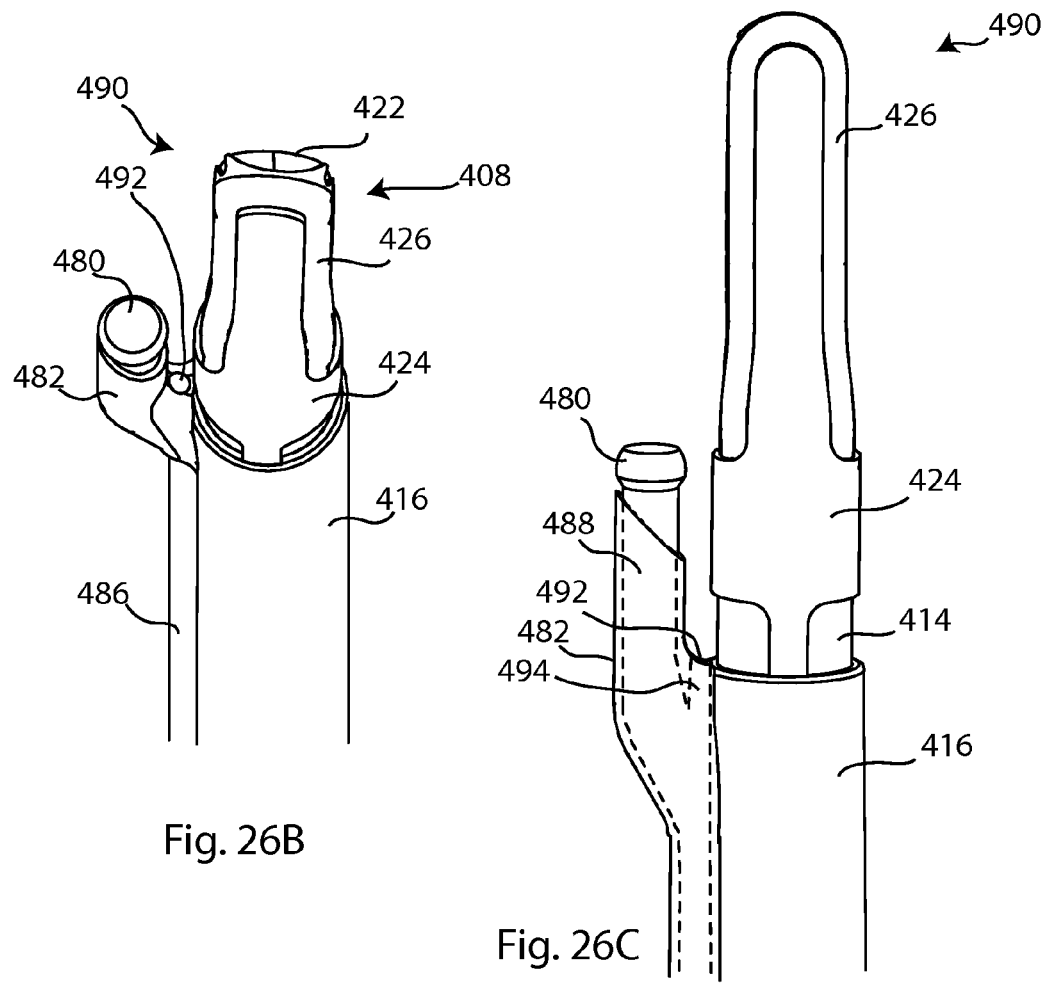
Fig. 26A
Fig. 26B
Fig. 26C

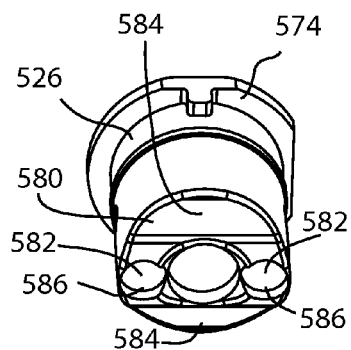
Fig. 33A
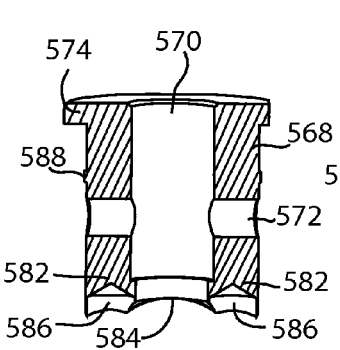
Fig. 33B
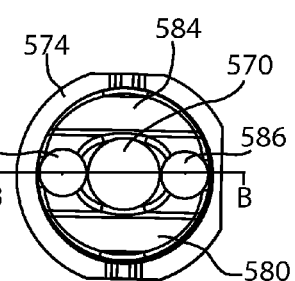
Fig. 33C
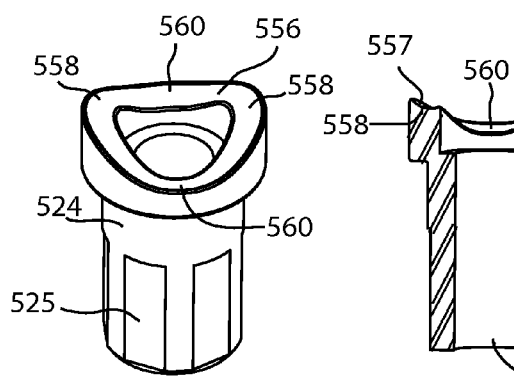
Fig. 32A
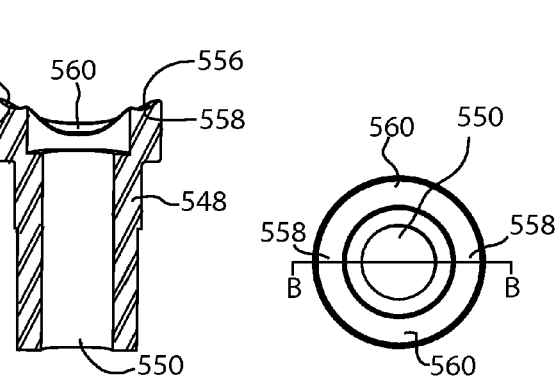
Fig. 32B
Fig. 32C

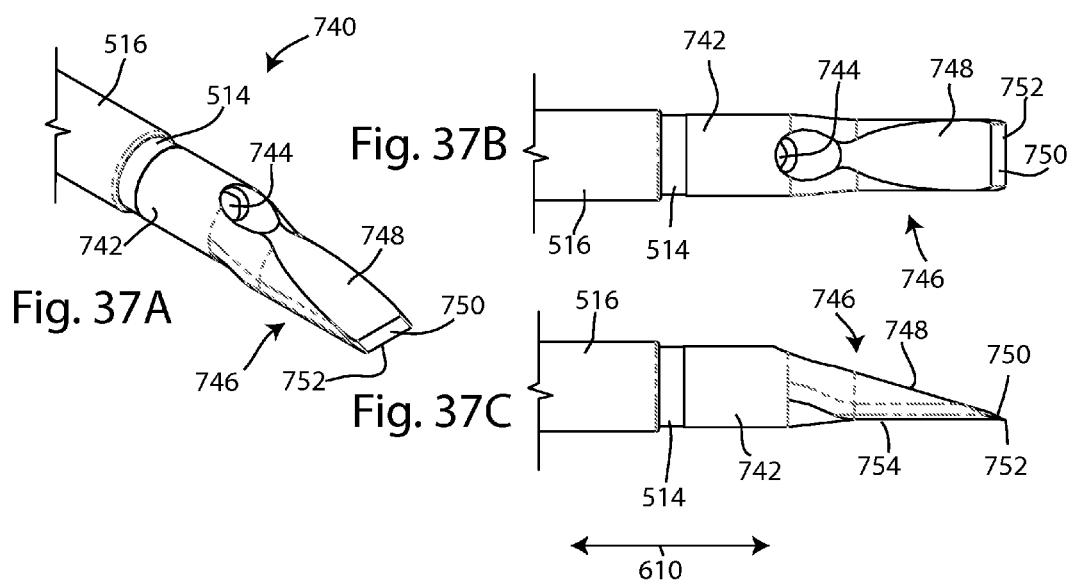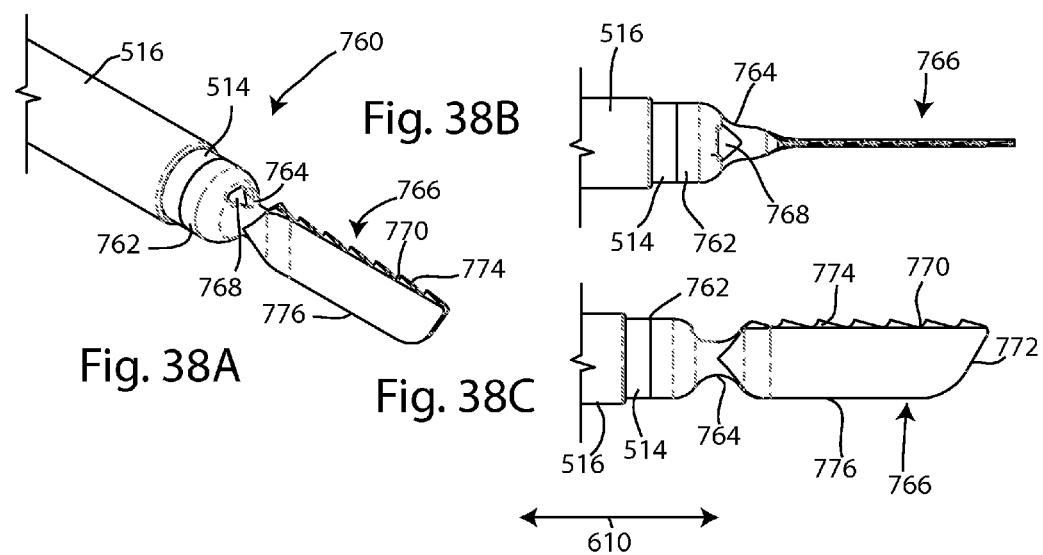

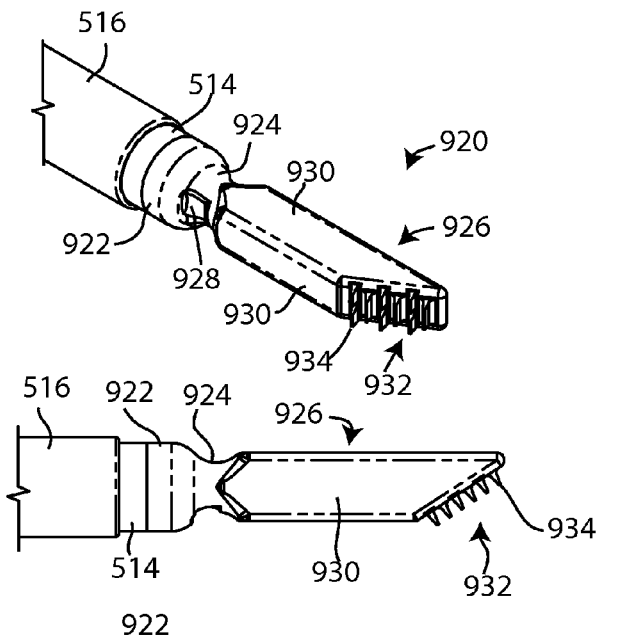
Fig. 46A
Fig. 46B
Fig. 46C
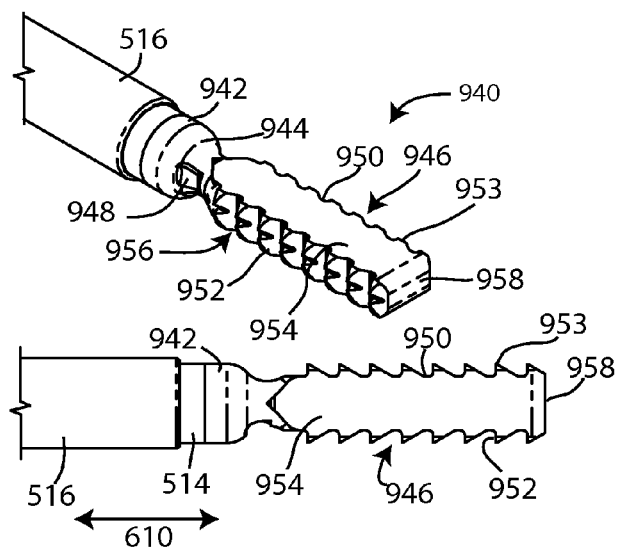
Fig. 47A
Fig. 47B

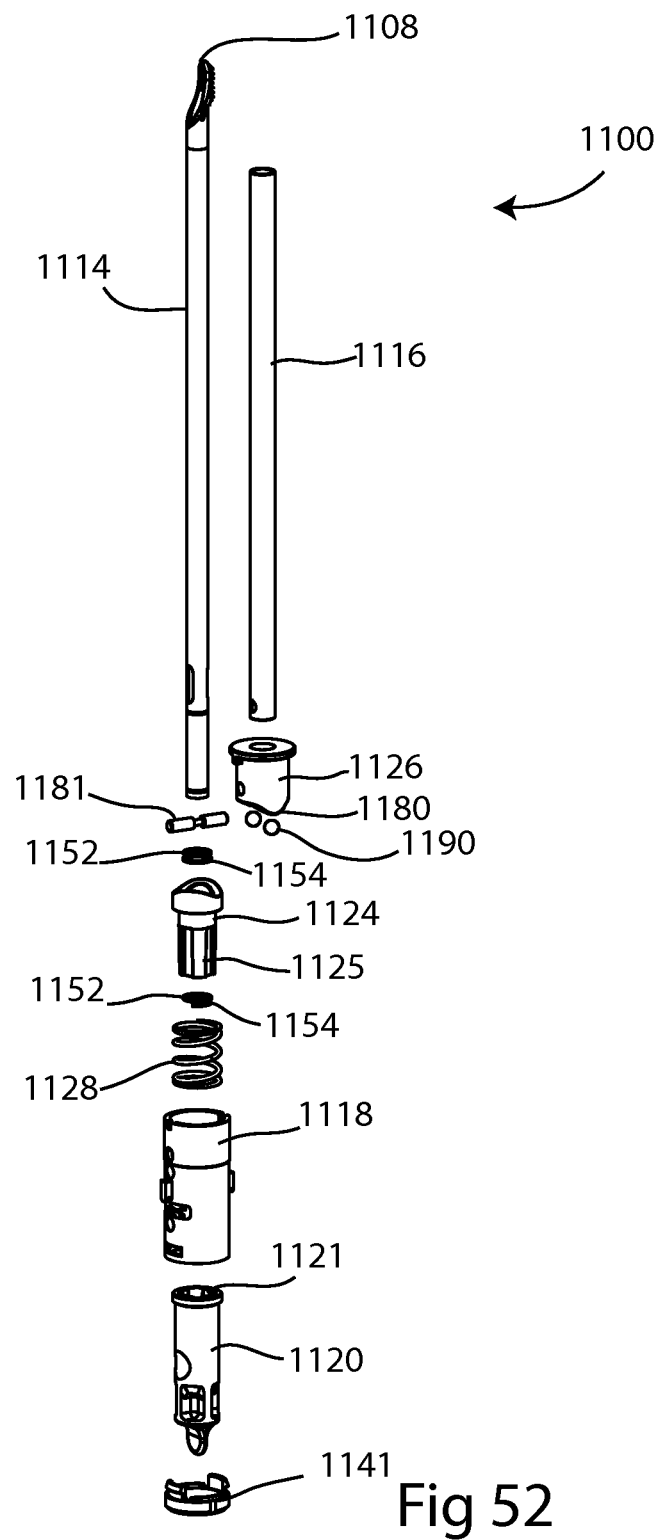

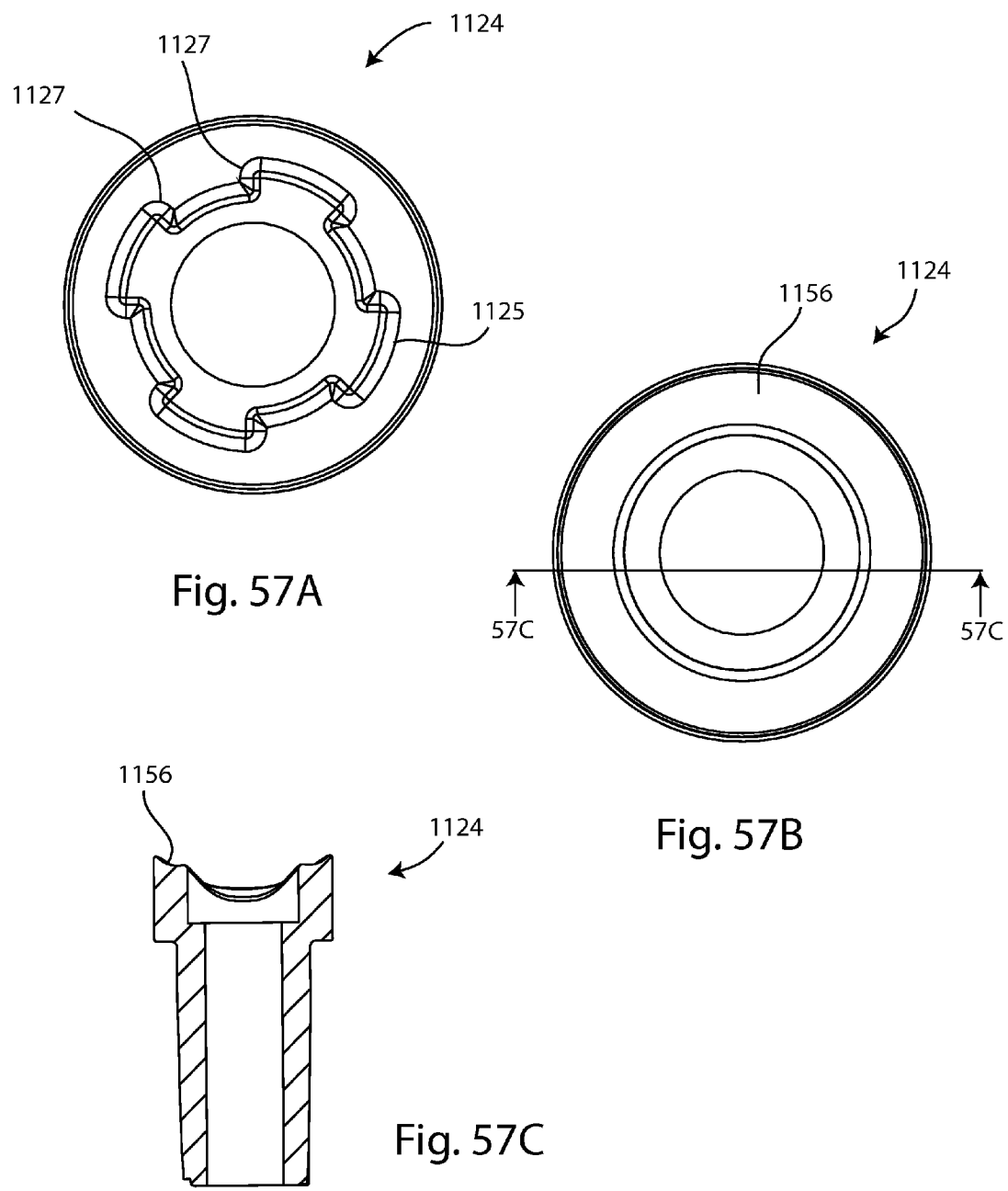

RECIPROCATING SURGICAL INSTRUMENT

CROSS-REFERENCE TO RELATED APPLICATIONS

This application is a continuation-in-part of:

pending U.S. application Ser. No. 13/231,121, filed Sep. 13, 2011, and is entitled RECIPROCATING SURGICAL INSTRUMENT, which is a continuation-in-part of:

pending U.S. application Ser. No. 13/102,351, filed May 6, 2011, and is entitled SURGICAL RASP WITH RADIOFREQUENCY ABLATION, which is a continuation-in-part of:

pending U.S. application Ser. No. 12/765,451, filed Apr. 22, 2010, and is entitled SURGICAL RASPING SYSTEMS AND METHODS, which is a non-provisional of:

U.S. Provisional Patent Application No. 61/245,487, filed Sep. 24, 2009, and is entitled SURGICAL RASPING SYSTEM.

U.S. application Ser. No. 13/231,121 is also a non-provisional of:

U.S. Provisional Patent Application No. 61/382,750, filed Sep. 14, 2010, and is entitled RECIPROCATING SURGICAL INSTRUMENTS; and U.S. Provisional Patent Application No. 61/382,758, filed Sep. 14, 2010, and is entitled RECIPROCATING SURGICAL INSTRUMENTS WITH ANGLED CUTTING FACES; and U.S. Provisional Patent Application No. 61/382,772, filed Sep. 14, 2010, and is entitled CUTTING HEADS FOR RECIPROCATING SURGICAL INSTRUMENTS.

U.S. application Ser. No. 13/102,351 is also a non-provisional of:

U.S. Provisional Patent Application No. 61/332,308, filed May 7, 2010, and is entitled RECIPROCATING RASP WITH RF ABLATION PROBE; and U.S. Provisional Patent Application No. 61/382,795, filed Sep. 14, 2010, and is entitled RECIPROCATING SURGICAL INSTRUMENTS WITH ADDED FUNCTIONALITY.

This application is also a non-provisional of:

U.S. Provisional Patent Application No. 61/635,196, filed Apr. 18, 2012, and is entitled RECIPROCATING SURGICAL INSTRUMENT.

The above-identified documents are incorporated herein by reference in their entirety.

FIELD OF THE DISCLOSURE

This disclosure relates to surgical tissue removal devices by which anatomical tissues may be cut and removed from a joint or other operative site. Specifically, this disclosure relates to instruments having reciprocating motion and/or suction.

BACKGROUND OF THE INVENTION

Surgical procedures including subacromial decompression, arthroscopic resection of the acromioclavicular joint (also known as the Mumford procedure), and anterior cruciate ligament reconstruction involving notchplasty, may all necessitate removal of osteophytes. Other conditions such as chondromalacia and osteochondritis dissecans may call for removal of osteophytes or chondrocytes. It is known to use shavers and burrs having rotational cutting surfaces to remove these hard tissues. However, the round cutting surface of a shaver or burr system is not advantageous to creating or preparing a flat surface. Additionally, the forces applied while using a rotational round cutting surface tend to pull the cutting end to either side by a moment force pivoting on the hand making precise control difficult. Working in confined spaces may exacerbate these issues, as adjacent soft tissues may easily be grabbed by a rotating cutting surface. An instrument with a reciprocating, instead of rotary, cutting end may provide a surgeon with greater control over the instrument and enhanced ability to selectively remove targeted tissues, especially in confined areas and/or during arthroscopic procedures. One type of reciprocating instrument may include cutting ends with rasping surfaces for preparation of flat joint surfaces. Another type of reciprocating instrument may include cutting ends with cutting, sawing or punching action for trimming of unwanted tissue.

BRIEF DESCRIPTION OF THE DRAWINGS

Various embodiments of the present technology will now be discussed with reference to the appended drawings. It is appreciated that these drawings depict only typical embodiments of the technology and are therefore not to be considered limiting of the scope of the claims herein.

FIG. 3A in an enlarged isometric view of a rasp head of the rasping system of FIG. 1A; FIG. 3B is a front view of the rasp head of FIG. 3A; FIG. 3C is a side view of the rasp head of FIG. 3C; FIG. 3D is a cross-sectional view of the rasp head of FIG. 3A taken along section line D-D;

FIG. 25A is a bottom view of a reciprocating rasp device including an auxiliary device; FIG. 25B is an enlarged view of a head portion of the device of FIG. 25A; FIG. 25C is a cross-sectional view of a shaft portion of the device of FIG. 25A taken along line C-C;

FIG. 26A is a top isometric view of a reciprocating rasp device including an auxiliary device, RF ablation system, and an infusion system; FIG. 26B is a top view of the device of FIG. 26A, FIG. 26C is a side isometric view of the device of FIG. 26A;

FIG. 32A is an isometric view of a rotatable cam of the system of FIG. 27; FIG. 32B is a cross-sectional view of the rotatable cam of FIG. 32A taken along line B-B; FIG. 32C is an end view of the rotatable cam of FIG. 32A;

FIG. 33A is an isometric view of a fixed cam of the system of FIG. 27; FIG. 33B is a cross-sectional view of the fixed cam of FIG. 33A taken along line B-B; FIG. 33C is an end view of the fixed cam of FIG. 33A;

FIG. 37A is an isometric view of a distal end of a tissue removal member having a cutting head with a chisel-type edge; FIG. 37B is a top view of the cutting head of FIG. 37A; FIG. 37C is a side view of the cutting head of FIG. 37A;

FIG. 38A is an isometric view of a distal end of a tissue removal member having a cutting head with a saw-type edge; FIG. 38B is a top view of the cutting head of FIG. 38A; FIG. 38C is a side view of the cutting head of FIG. 38A;

FIG. 46A is an isometric view of a distal end of a tissue removal member having a distal face cutting head; FIG. 46B is a side view of the cutting head of FIG. 46A; FIG. 46C is a top view of the cutting head of FIG. 46A;

FIG. 47A is an isometric view of a distal end of a tissue removal member having a rectangular cutting head; FIG. 47B is a side view of the cutting head of FIG. 47A;

FIG. 52 is an exploded view of the reciprocating surgical instrument of FIG. 50;

FIG. 57A is a bottom view of the proximal end of the rotatable cam of FIG. 56A; FIG. 57B is a top view of the distal end of the rotatable cam of FIG. 56A; FIG. 57C is a cross-sectional side view of the rotatable cam of FIG. 56A, taken along the line 57C-57C in FIG. 57B;

72A with the shaving blade in the extended position.

DETAILED DESCRIPTION OF THE PREFERRED EMBODIMENTS

Figure 1A:
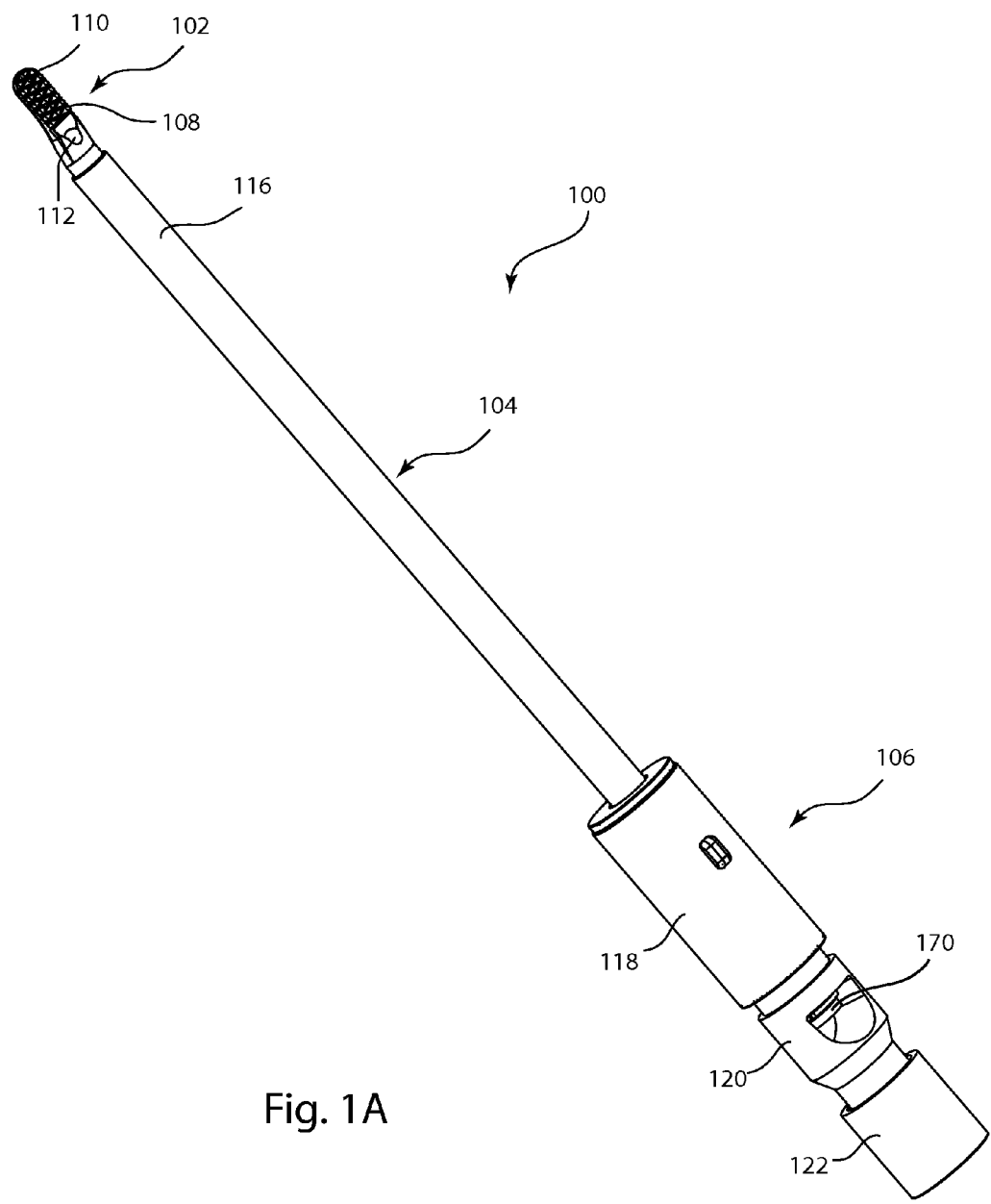
FIG. 1A is an isometric view of a reciprocating rasping system.

The present disclosure relates to tissue removal devices and methods by which body tissues may be cut or shaved and removed during surgery. Those of skill in the art will recognize that the following description is merely illustrative of the principles of the disclosure, which may be applied in various ways to provide many different alternative embodiments. This description is made for the purpose of illustrating the general principles of this invention and is not meant to limit the inventive concepts in the appended claims.

The present disclosure provides rasping and shaving systems that are shaped to be functional in multiple orthopedic surgery applications, including but not limited to shoulder, knee, hip, wrist, ankle, spinal, or other joint procedures. The system comprises a rasping and/or shaving head which may be low profile and offer a flat cutting/rasping/shaving surface, and is configured to be driven by an attached hub that will translate a rotational movement into a reciprocating motion. Suction for removal of bone fragments or other tissue fragments may be provided through an opening in or adjacent to the rasping head. This device provides an alternative method of removing tissue to the currently used shavers and burrs that offer a rotational cutting surface. By applying a reciprocating cutting surface, the surgeon has greater control over the instrument and is better able to create/prepare a flat, convex, or concave surface. The reciprocating force of the device applies resisting pressure to the surgeon's hand in the axial direction with the hand, making control much easier. Increased control will result in a decrease in injury to the surrounding soft tissue. The device also has a lower profile than many of the existing shaver systems allowing access to tight joints without damaging surrounding tissues. The teeth of the device may be positioned such that the cut material will be pulled towards the suction pathway to more efficiently remove debris from the surgical site, thus decreasing the duration of a procedure.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, a standard system of three mutually perpendicular reference planes is employed. A sagittal plane divides a body into right and left portions; a mid-sagittal plane divides a body into bilaterally symmetric right and left portions. A coronal plane divides a body into anterior and posterior portions. A transverse plane divides a body into superior and inferior portions.

Any of the devices described herein may be fabricated from metals, alloys, polymers, plastics, ceramics, glasses, composite materials, or combinations thereof. Different materials may be used within a single part.

Referring to FIG. 1A, rasp system 100 is shown in an isometric view. Rasp system 100 comprises head portion 102, shaft portion 104, and handle portion 106. Head portion 102 comprises rasp head 108, which includes a plurality of teeth 110 or cutting edges which may cut anatomical tissues when drawn along the tissue surface. The teeth may be particularly suited for cutting or removing hard tissues such as bone or cartilage. A suction opening 112 is located on the head portion 102, and may be disposed between the teeth and the shaft portion. The shaft portion 104 comprises inner shaft 114 (not visible in FIG. 1A) which extends proximally from the rasp head 108 and is received in the handle portion 106. The inner shaft 114 extends through an optional outer sleeve 116 which is joined to the handle portion 106. At its proximal end, inner shaft 114 is received within a shaft key 170 (not visible in FIG. 1A).

Handle portion 106 includes an outer housing 118, a driving hub 120, and a spring collet 122 which houses a spring 250 (not visible in FIG. 1). Outer housing 118 comprises a cam surface (not visible in FIG. 1) which is complementarily shaped to a cam follower surface on driving hub 120. When handle portion 106 is engaged in a powered rotary handpiece and power is supplied, hub 120 rotates, and the cam and cam follower surfaces provide a motion conversion mechanism which converts the rotary motion of the hub to axial reciprocal motion of the inner shaft 114 and attached head 108. Rasp system 100 is connectable via spring collet 122 to a powered handpiece, to provide rotary power to the rasp system, and to provide suction. Suitable handpieces include the Linvatec Advantage Shaver (Ref D9824) brand powered rotary handpiece or another similar system known in the art.

Figure 1B:
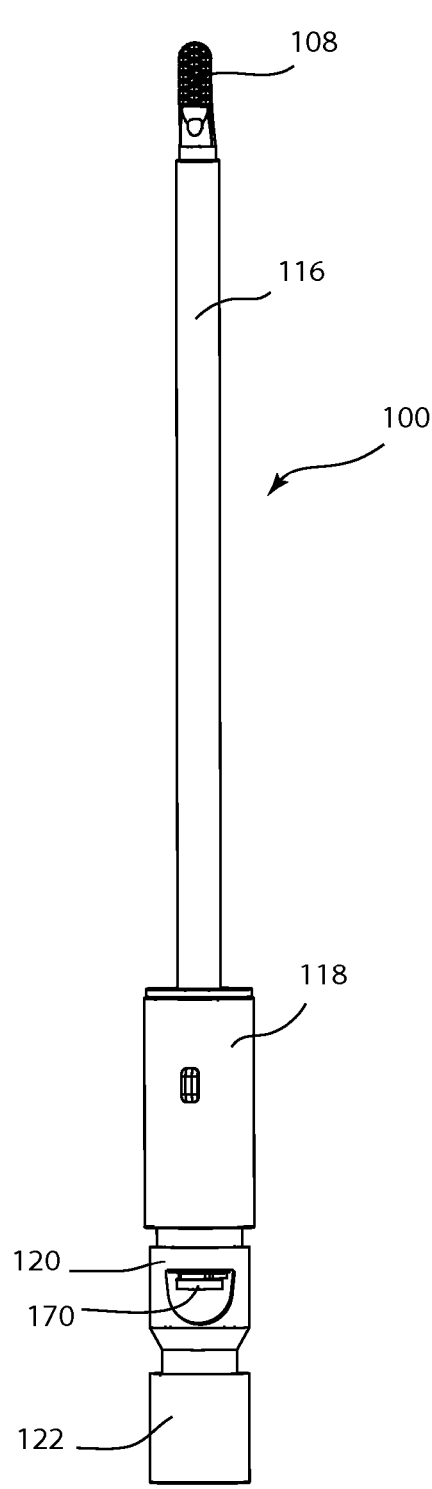
FIG. 1B is a front view of the rasping system of FIG. 1A in a retracted configuration.
Figure 1C:
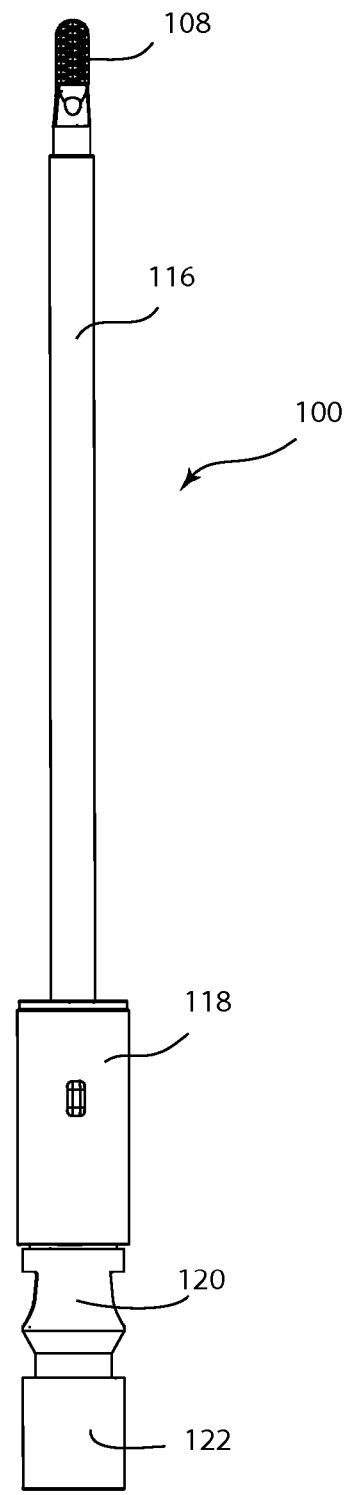
FIG. 1C is a front view of the rasping system of FIG. 1A in an extended configuration.

FIG. 1B illustrates rasp system 100 in a retracted configuration. In this configuration, the shaft key 170, inner shaft 114 (not visible; within outer sleeve 116) and rasp head 108 have been pulled by interaction of the cam and cam follower surfaces to a proximal position. FIG. 1C illustrates rasp system 100 in an extended configuration. In this configuration, driving hub 120 has rotated relative to the outer housing 120; and the shaft key, inner shaft 114 and rasp head 108 have been reciprocally translated to a distal position by the spring bias of spring 250. It is appreciated that an alternate embodiment of the invention may include a curved inner shaft and, optionally, a curved outer sleeve. In the curved embodiment the rasp head may be angled relative to the inner shaft, and the outer sleeve may be sized to allow free reciprocation of the inner shaft.

Figure 2:
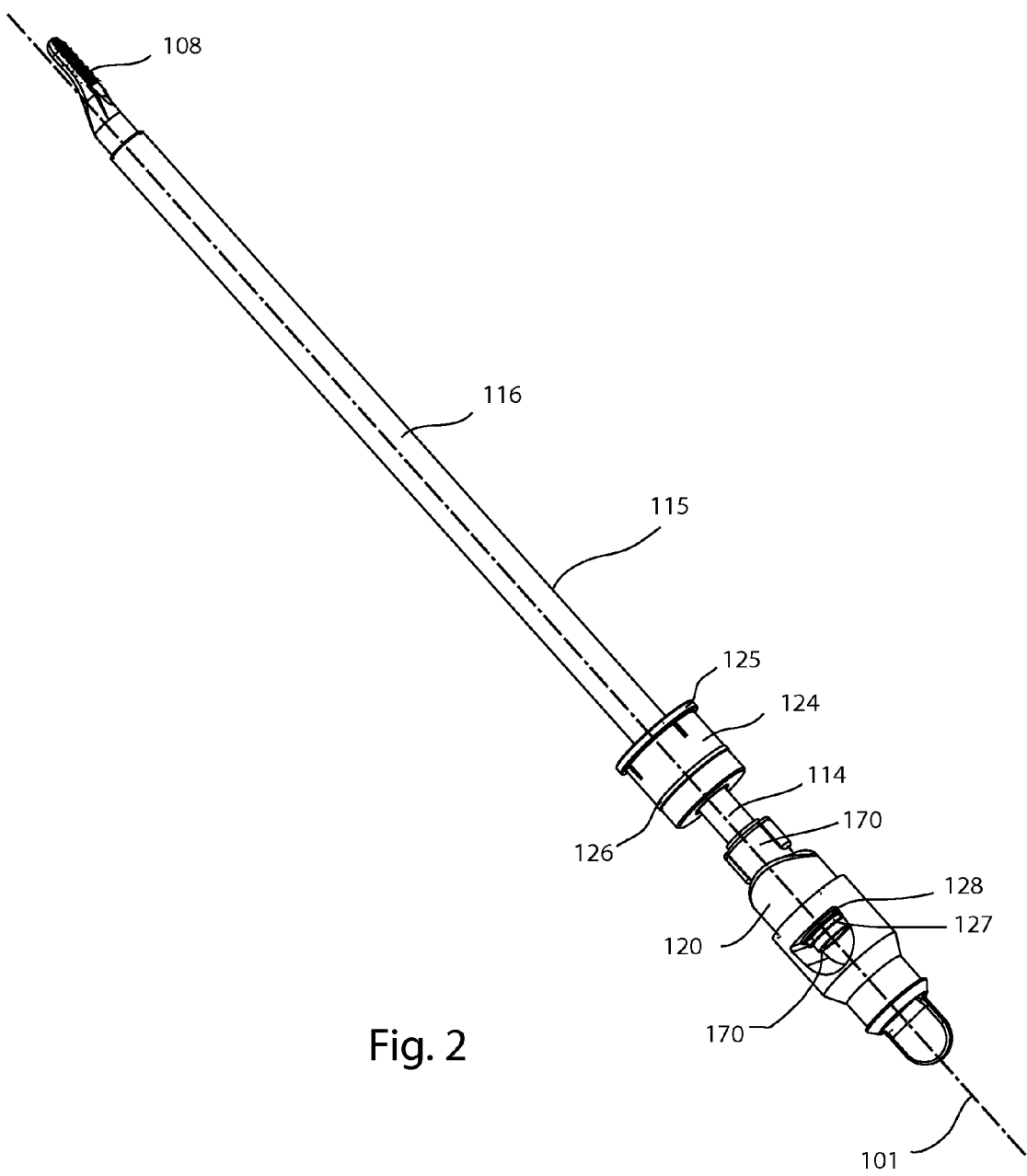
FIG. 2 is an isometric view of the rasping system of FIG. 1A with an outer housing and collet removed, and a longitudinal axis of the rasping system.

FIG. 2 illustrates rasp system 100 minus the outer housing 118 and spring collet 122. Outer sleeve 116 is joined to plug 124. Plug 124 comprises a rim 125 and a protruding ring 126. When received within the outer housing 118 as in FIG. 1, ring 126 may provide a snap connection with a groove feature within outer housing 118, and rim 125 may seat against a distal end of the outer housing. Once joined with the outer housing 118, plug 124 and outer sleeve do not translate or rotate relative to the outer housing. The outer sleeve 116 provides protection to surrounding tissues when rasp system 100 is used; outer sleeve 116 does not rotate or reciprocate, yet allows reciprocal movement of inner shaft 114 within. Space between the inner shaft 114 and the outer sleeve 116 may optionally be lubricated. Together, the rasp head 108, inner shaft 114 and shaft key 170 comprise a tissue removal member 115.

Proximal to the plug 124, the inner shaft 114 is received in the shaft key 170 and is non-movable relative to the shaft key. A portion of shaft key 170 is received within a portion of hub 120, which is rotatable about the shaft key. A snap ring 127 is received in a groove formed at the proximal end of the shaft key, and retains the shaft key 170 within the hub 120 while still allowing the hub 120 to rotate about the shaft key. A washer 128 is positioned around the shaft key 170 between the snap ring 127 and the hub 120. The system 100 comprises a longitudinal axis 101 about which the hub 120 rotates, and along which the tissue removal member 115 is reciprocally translated.

Referring to FIGS. 3A through 3D, several views of rasp head 108 are shown. Rasp head 108 comprises a distal end 130, and a proximal end 132, and further comprises a working portion 134, a head transition portion 144 and a head shaft portion 154. The working portion 134 comprises a first side 136 which may be also be known as a front side, and a second, or back side 138 opposite the first side. A tissue removal surface 140 is disposed on the first side 136, although it is appreciated that in alternate embodiments, the tissue removal surface may be disposed on the back side, or on both the front and back sides. The tissue removal surface 140, may be flat as in FIGS. 3A-3D, or in other embodiments may be concave or convex. The plurality of teeth 110 populates the tissue removal surface, each tooth having a cutting portion 142. The cutting portion 142 may be a point as seen in the teeth depicted in FIGS. 3A-3D, but in other embodiments the cutting portion may be an edge, or a combination of one or more edges and a point. The teeth may be distributed individually; in even ranks or rows; or in alternate ranks or rows. In alternative embodiments of the cutting head, the number, size, and distribution of the teeth may vary to provide a variety of tissue cutting surfaces suitable for different tissue removal procedures. The cutting portions 142 may be uni-directionally oriented as in FIGS. 3A-3D, meaning that all of the teeth point the same direction. Advantageously, the teeth may be pointed toward the suction opening 112, thus facilitating efficient movement of cut debris into the suction opening. Another feature of uni-directional teeth is that the teeth may only cut into tissue when the rasp head is moved in one direction; for example if the teeth are pointed proximally, cutting will occur when the rasp head is translated proximally.

The transition portion 144 extends between the working portion and the head shaft portion, and may be angled relative to the working and/or head shaft portions. Proximal to and spaced apart from the tissue removal surface, the suction opening 112 provides a distal opening to a suction pathway. A fan-like scoop portion 146 adjacent the suction opening 112 may funnel excised tissue toward the suction opening. A head suction bore 148 extends proximally from the suction opening 112, forming a portion of the suction pathway.

The head shaft portion 154 extends from the transition portion 144 to the proximal end 132 of the rasp head 108. At the proximal end 132, a fitting or connection feature 133 allows for joining of the rasp head 108 to the inner shaft 114. The head suction bore 148 terminates at the proximal end 132, but the suction pathway continues through the hollow inner shaft 114. The rasp head 108 may be removably joined to the inner shaft via a press fit or mechanical fit, or may be permanently joined via a weld or other permanent connection.

Figures 4A, 4B:
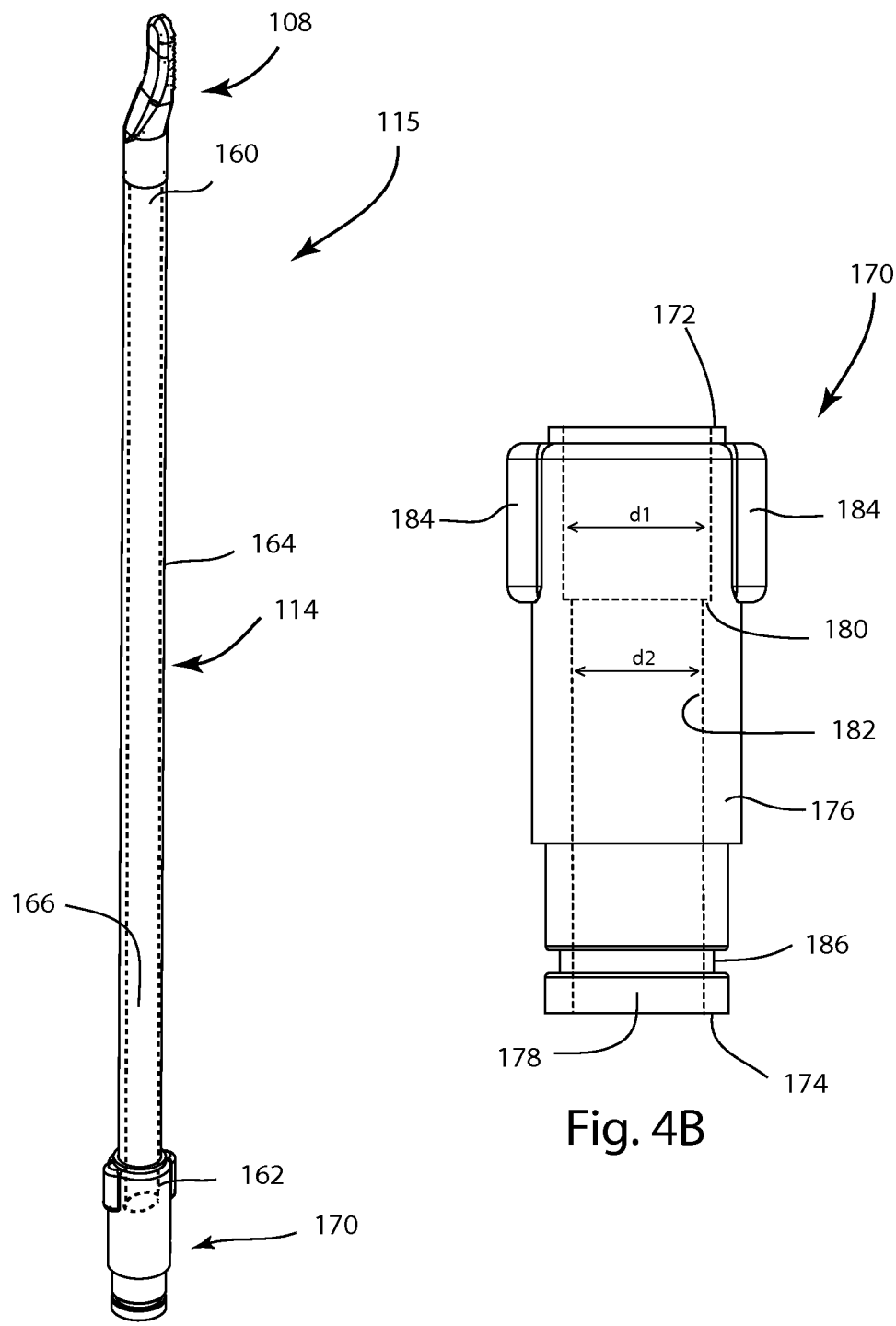
FIG. 4A is a iso-side view of a tissue removal member of the rasping system of FIG. 1A.
FIG. 4B is an enlarged side view of a shaft key of the tissue removal member of FIG. 4A.

FIG. 4A illustrates the rasp head 108, inner shaft 114, and a shaft key 170, which together comprise the tissue removal member 115. The inner shaft 114 comprises a tubular member having a distal end 160, a proximal end 162 and an inner shaft body 164 extending therebetween. The inner shaft body defines an inner shaft bore 166, indicated by dashed lines, extending from the distal end to the proximal end, forming a portion of the suction pathway. The proximal end 162 of the inner shaft is received in the shaft key 170. Inner shaft 114 may be glued, welded, bonded, press fit or otherwise permanently joined to shaft key 170, so that no movement including translation or rotation between inner shaft 114 and shaft key 170 is allowed. Inner shaft 114 may be monolithically formed with shaft key 170.

Referring to FIG. 4B, shaft key 170 comprises a distal end 172, a proximal end 174, and generally cylindrical key body 176 extending therebetween. A key bore 178 (indicated by dashed lines) extends the length of the shaft key, and forms a portion of the suction pathway. At its distal end, the key bore has a first diameter d1 dimensioned to receive the proximal end of the inner shaft 114. Proximal to a shoulder 180 formed in an inner wall 182 of the key body 176, the key bore has a second diameter d2. Two individual wings 184 protrude from the key body 176, opposite from one another near the distal end 172. The wings 184 are shaped to be received in recesses formed within the outer housing, preventing rotation of the tissue removal member when the hub is rotated. It is appreciated that in other embodiments of the invention, the number and placement of the wings 184 may vary, or the wings may be formed on the outer housing, to be received in recesses formed on the shaft key 170. Toward the proximal end 174 of the shaft key 170, an annular groove 186 is formed on the outside of the key body 176. The groove 186 is shaped to receive snap ring 127. The suction pathway comprises the continuous pathway formed by head suction bore 148, inner shaft bore 166 and key bore 178.

Outer housing 118 is illustrated in FIGS. 5A through 5D. The tissue removal member 115 is receivable in the outer housing, while the outer housing is shaped to be received in a powered handpiece. Outer housing 118 is generally cylindrical and comprises a distal end 190, a proximal end 192 and an outer housing body 194 extending therebetween. A tab 196 protrudes exteriorly from the outer housing body, and is shaped to be received in a groove formed in a powered handpiece, to both properly align the rasp system 100 within the handpiece and prohibit rotation of the outer housing 118 relative to the handpiece.

Figure 5A:
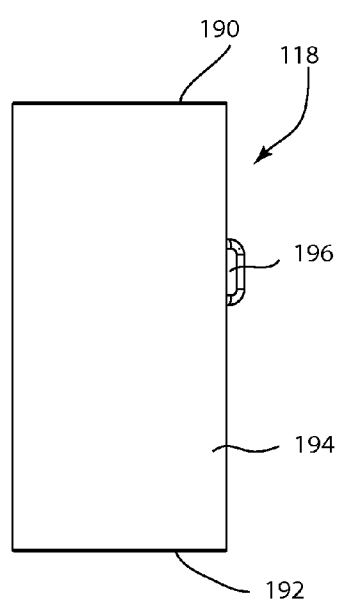
FIG. 5A is a side view of an outer housing of the rasping system of FIG. 1A.
Figure 5B:
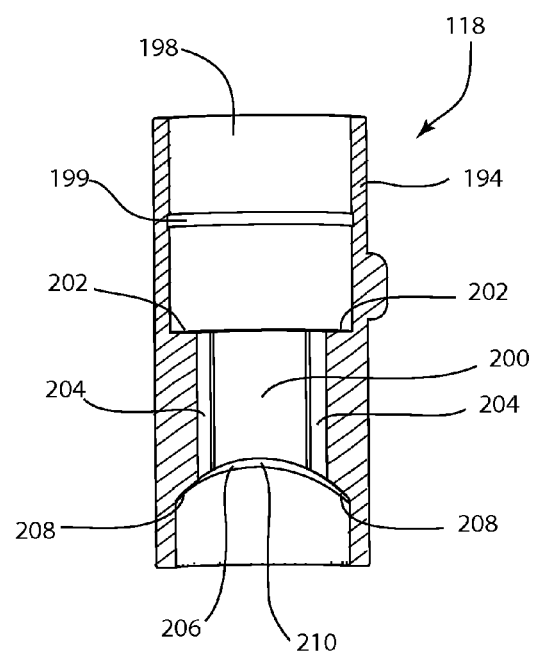
FIG. 5B is cross-sectional view of the outer housing of FIG. 5A, taken along line B-B of FIG. 5C.
Figure 5C:
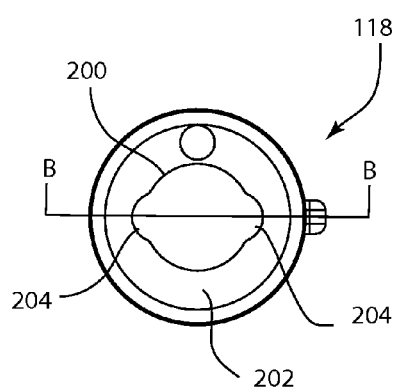
FIG. 5C is a top end view of the outer housing of FIG. 5A.

FIG. 5B is a longitudinal cross-sectional view of the housing, taken along line B in FIG. 5C. Extending longitudinally through the housing is housing bore 198. Toward the distal end of the housing, bore 198 is shaped to receive the generally cylindrical plug 124 (not shown) which in turn receives the outer sleeve 116. An annular inner groove 199 is shaped to fit around the ring 126 on the outer surface of the plug. An annular shoulder 202 is formed in the inner wall of the housing body 194. A keyway, or key portion 200 of the housing bore 198 is constricted, and shaped to receive a portion of the shaft key 170. Two recesses 204 in the key portion 200 are shaped to complementarily fit the wings 184 of the shaft key 170. When the shaft key 170 is received in the key portion 200 of the housing 118, the complementary fit of the wings 184 in the recesses 204 prohibits rotation of the shaft key 170, and thus tissue removal member 115, relative to the outer housing 118, but allows proximal-distal/distal-proximal translation of the shaft key 170 relative to the outer housing.

Figure 5D:
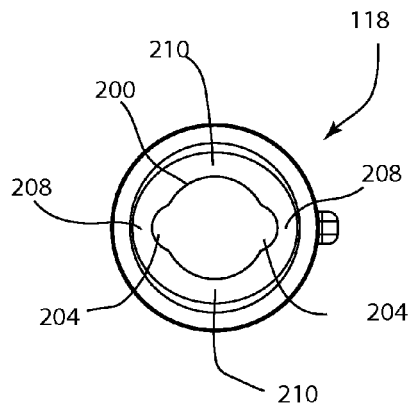
FIG. 5D is a bottom end view of the outer housing of FIG. 5A.

Referring to FIG. 5D, a bottom end view shows an undulating, annular cam surface 206 formed in the inner wall of the housing body 194. The annular cam surface 206 comprises two lobes 208, formed as two portions which protrude proximally, parallel to the longitudinal axis, on opposite sides of the bore 198 from one another. At the lobes 208, cam surface 206 slopes proximally from its outer diameter to its inner diameter. The lobes 208 are evenly interspersed with two hollows 210, such that, when viewed from the side, the annular cam surface 206 undulates evenly between two low points at the lobes 208, and two high points at the hollows 210.

Figure 6A:
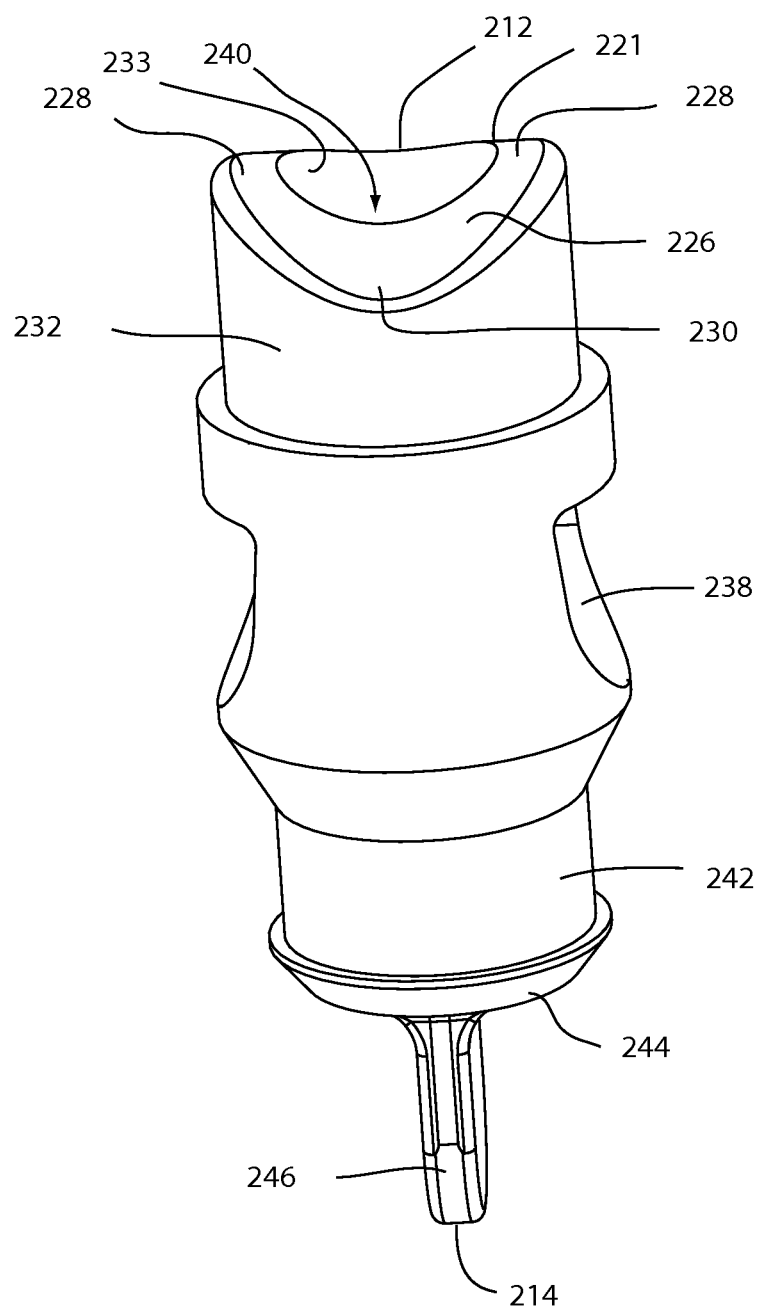
FIG. 6A is an isometric view of a first side of a driving hub of the rasping system of FIG. 1A.
Figure 6B:
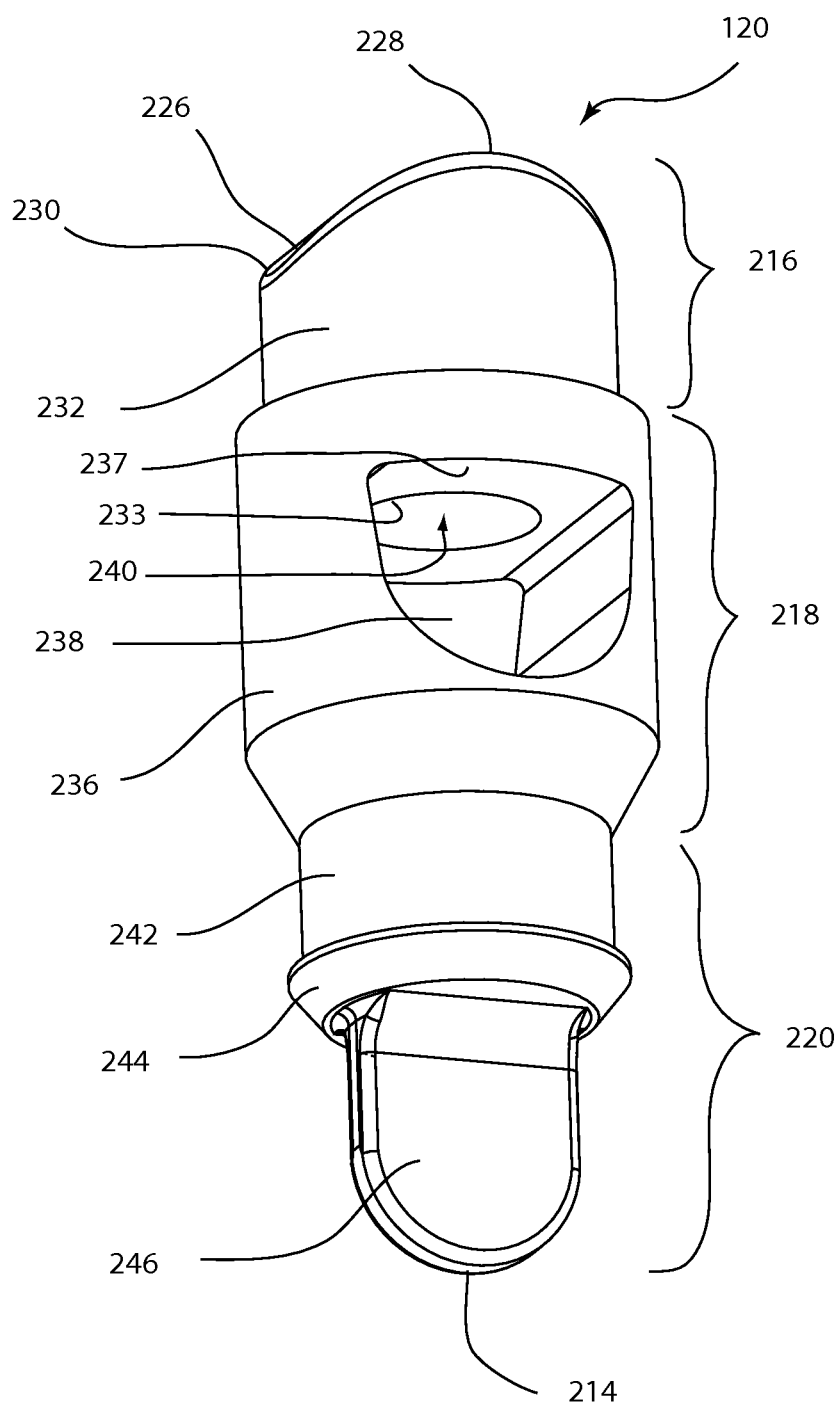
FIG. 6B is an isometric view of a second side of a driving hub of the rasping system of FIG. 1A.

The driving hub 120 is illustrated in FIGS. 6A and 6B. The hub 120 extends longitudinally between a distal end 212 and a proximal end 214. The hub 120 comprises three portions: a distal cam portion 216, an intermediate portion 218, and a proximal driving portion 220. At the distal end 212, the hub terminates in a distal end face 221 having a cam follower surface 226 which is shaped complementarily to the cam surface 206. The cam follower surface comprises two follower lobes 228 interspersed with two follower hollows 230. At the follower hollows 230, cam follower surface 226 slopes proximally from its outer diameter to its inner diameter. The follower lobes 228 are evenly interspersed with the follower hollows 230, such that, when viewed from the side, the cam follower surface 226 undulates evenly between two low points at the hollows 230, and two high points at the lobes 228. The distal cam portion 216 is circumscribed by an annular outer wall 232. A driving hub bore 240, lined by an annular inner wall 233, extends longitudinally through the distal cam portion 216.

The intermediate portion 218 of the hub 120 comprises an intermediate body 236, through which an aperture 238 extends transversely. The driving hub bore 240 continues longitudinally from the distal cam portion 216 and terminates at a proximal hub face 237, in communication with the aperture 238. The driving hub bore 240 forms the proximal portion of the suction pathway, which terminates as it opens into the aperture.

The driving portion 220 of the driving hub 120 provides a connection feature for connection to a powered handpiece. The driving portion 220 comprises a smooth, cylindrical hub body 242 which terminates at an annular flange 244. The flange 244 forms a lip extending exteriorly from the hub body. Proximal to the hub body and flange, a plate-like driving tab 246 projects longitudinally, and transversely across the diameter of the hub body. The driving tab 246 is shaped to be coupled with a driver in the powered handpiece, to provide rotational motion to the driving hub. It is appreciated that in other embodiments of the invention, the connection to the powered handpiece may take other forms, including but not limited to a square, star, cross, X-shape, H-shape, or other form compatible with the handpiece.

Figure 7A:
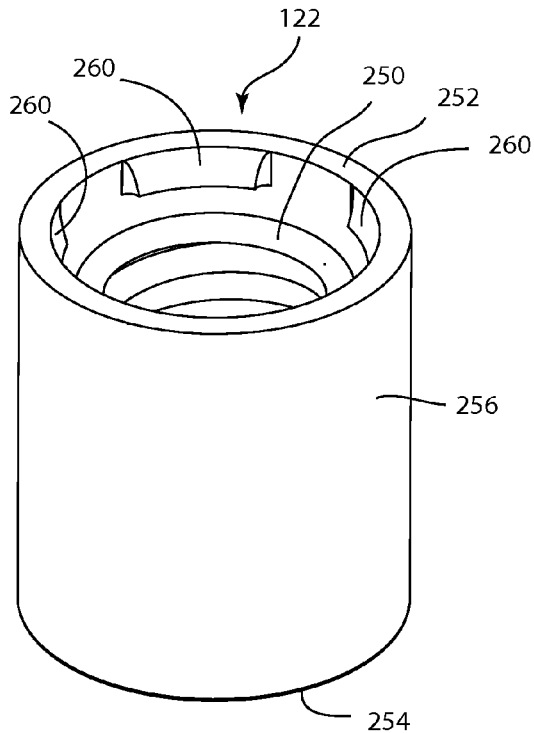
FIG. 7A is an isometric view of a spring collet and spring of the rasping system of FIG. 1A.
Figure 7B:
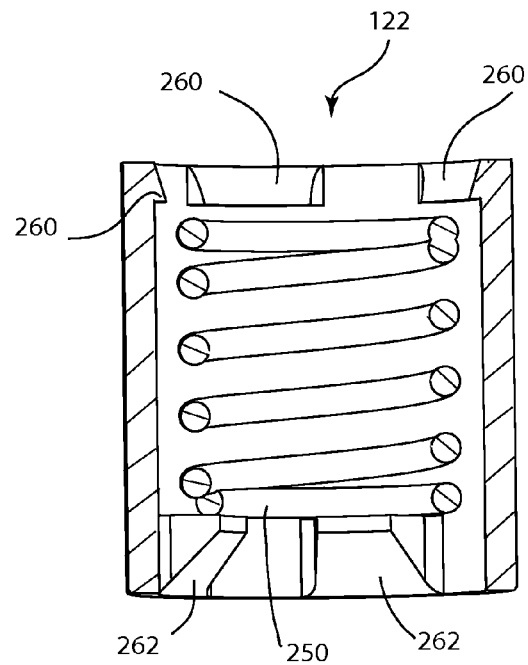
FIG. 7B is cross-sectional view of the spring collet and spring along section line B-B of FIG. 7C.
Figure 7C:
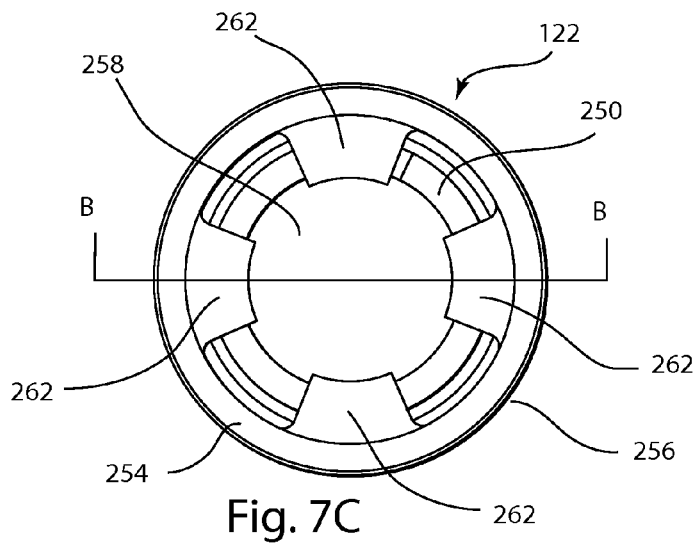
FIG. 7C is a bottom end view of the spring collet and spring of FIG. 7A.

Referring to FIGS. 7A through 7C, the spring collet 122 and a spring 250 are illustrated. Spring collet 122 is generally cylindrical and tubular in form, comprising a distal end 252, a proximal end 254, and a tubular collet body 256 extending therebetween. A collet bore 258 is defined and surrounded by the collet body 256. Adjacent the distal end 252, a plurality of distal stops 260 formed on the collet body 256 protrude inward into the collet bore 258. When the collet 122 is coupled with the driving hub 120, distal stops 260 cooperate with flange 244 to prevent the collet from becoming uncoupled yet allow rotation of the hub relative to the collet. Adjacent the proximal end 254, a plurality of proximal stops 262 formed on the collet body 256 protrude inward into the collet bore 258. As seen in FIG. 7B, the proximal stops may be larger than the distal stops, projecting farther into the collet bore. The proximal stops 262 prevent the spring 250 from escaping proximally out of the spring collet 122 and provide a platform against which the spring may be compressed. When coupled in collet 122 with driving hub 120, spring 250 is biased to push the driving hub 120 distally unless otherwise acted upon.

Figure 8:
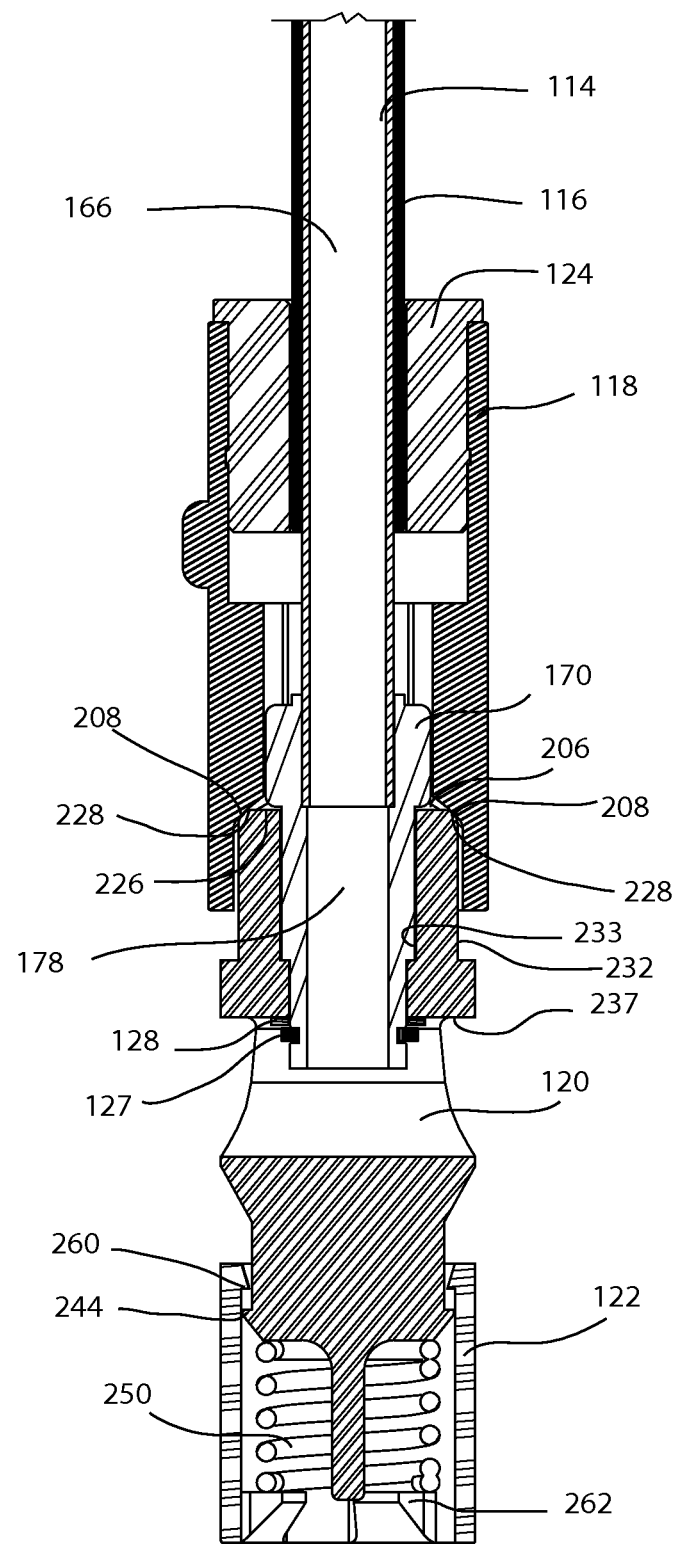
FIG. 8 is a longitudinal cross-sectional view of a handle portion and a segment of a shaft portion of the rasping system of FIG. 1A in the retracted position.
Figure 9:
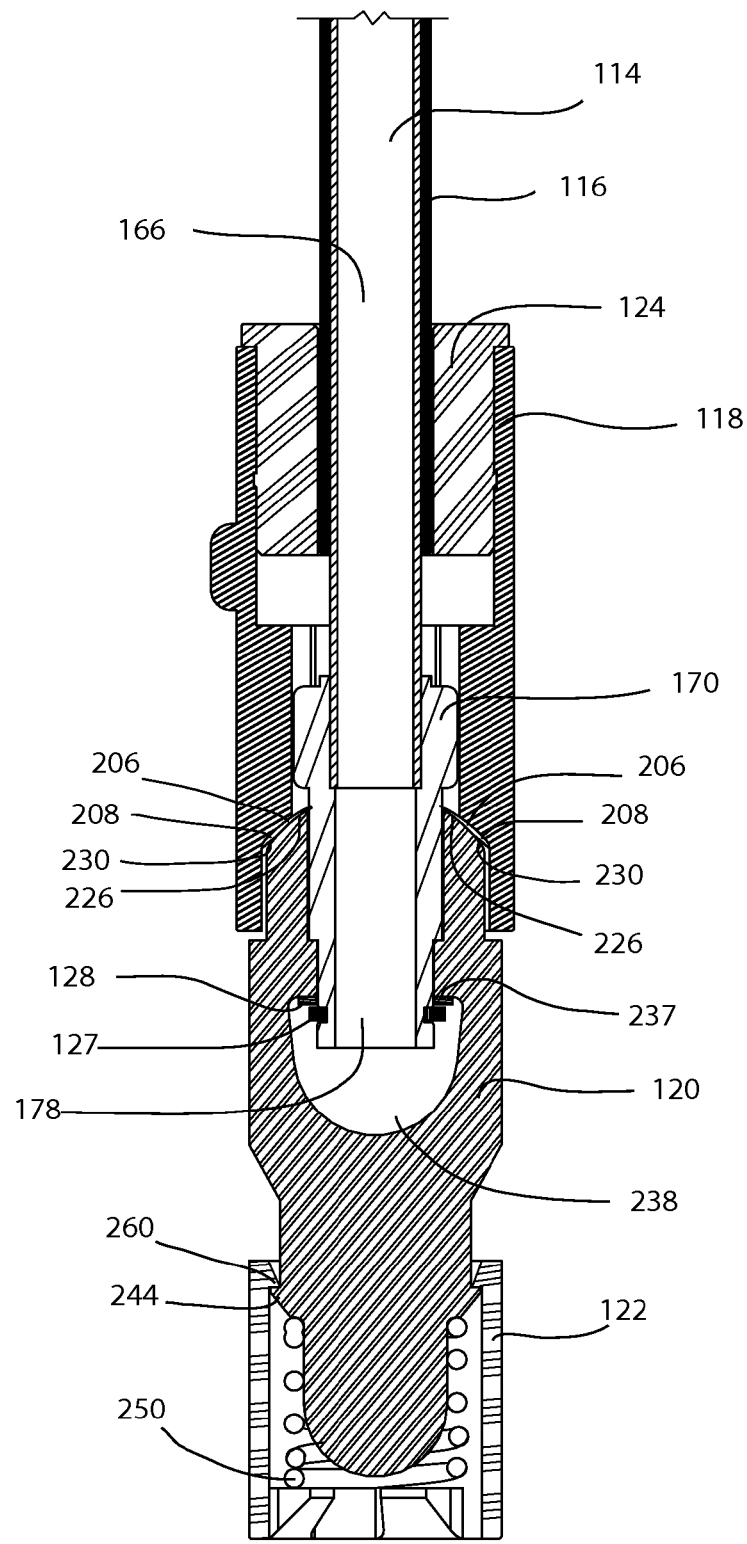
FIG. 9 is a longitudinal cross-sectional view of a handle portion and a segment of a shaft portion of the rasping system of FIG. 1A in the extended position.

FIGS. 8 and 9 provide cross-sectional views of the handle portion and a segment of the shaft portion of rasp system 100. FIG. 8 shows the rasp system 100 in a retracted configuration, in which the tissue removal member 115 comprising shaft key 170, inner shaft 114 and rasp head 108 is in a first position relative to the outer housing 118. FIG. 9 shows the rasp system 100 in an extended configuration, in which the tissue removal member 115 is in a second position relative to the outer housing 118, the second position distal to the first position. When the rasp system 100 is connected to the powered handpiece and power is supplied, hub 120 is rotated, and the interaction of the cam and cam follower surfaces and the bias of the spring convert the rotary motion of the hub to reciprocal motion of the tissue removal member between the extended and retracted configurations.

As set forth previously, inner shaft 114 is joined with shaft key 170; and shaft key 170 is received within housing 118 such that the wings 184 fit in recesses 204, allowing axial translation of shaft key 170 relative to the outer housing 118 but prohibiting rotation of shaft key 170. A proximal portion of shaft key 170 is received within the driving hub bore 240, which is rotatable relative to the shaft key 170 and the outer housing 118. More specifically, the inner wall 233 slidably rotates about the shaft key 170 while the outer wall 232 slidably rotates relative to the housing 118. The cam surface 206 of the outer housing 118 is positioned immediately adjacent the complementary cam follower surface 226 of the driving hub 120. The cam surface 206 of the outer housing 118 is distal to the proximal end of the tissue removal member 115.

A motion conversion mechanism, which may also be called a motion mechanism, is provided by the outer housing including its cam surface and the hub including its cam follower surface. In extended configuration, hub 120 is positioned such that cam follower surface 226 is flush against cam surface 206, with hollows 230 on follower cam surface 226 complementarily fitting against the lobes 208 of cam surface 206. In the retracted configuration, the driving hub 120 is rotated relative to the outer housing 118 such that the lobes 228 on follower cam surface push against the lobes 208 of cam surface 206, thus forcing driving hub 120 proximally, or downward, relative to the outer housing 118. As hub 120 moves proximally, shaft key 170, inner shaft 114 and rasp head 108 are pulled proximally with the hub, but they do not rotate. Proximal hub face 237 rotatably bears against washer 128, which in turn bears against split ring 127, to pull the tissue removal member 115 proximally. As hub 120 continues to rotate, spring 250 pushes distally to axially translate hub 120 back to the extended position, carrying with it shaft key 170, inner shaft 114 and rasp head 108. In the embodiment depicted in FIGS. 8 and 9, cam surface 206 and cam follower surface 226 each have two lobes and two hollows, so that with one full rotation of hub 120, tissue removal member 115 is twice axially reciprocated. In an alternate embodiment, the cam and cam follower surfaces may have more than two lobes and hollows, so that one rotation of the hub may result in multiple reciprocations. In another alternate embodiment, the cam and cam follower surfaces may each have only one lobe and one hollow, resulting in a single reciprocation per revolution. It is appreciated that while the lobes and hollows depicted herein are rounded, however in other embodiments the lobes and/or hollows may be pointed or sharply angular.

As set forth previously, rasp head 108 comprises uni-directionally oriented teeth, which are oriented proximally toward the suction opening 112. Thus, as tissue removal member 115 reciprocates distally and proximally, the teeth cut into any adjacent tissue as the tissue removal member moves proximally. This proximal cutting action may aid in moving cut tissue debris toward the suction opening. Reciprocation of the flat tissue removal surface 115 against the tissue allows for creation or preparation of a flat surface on the tissue.

Figure 10:
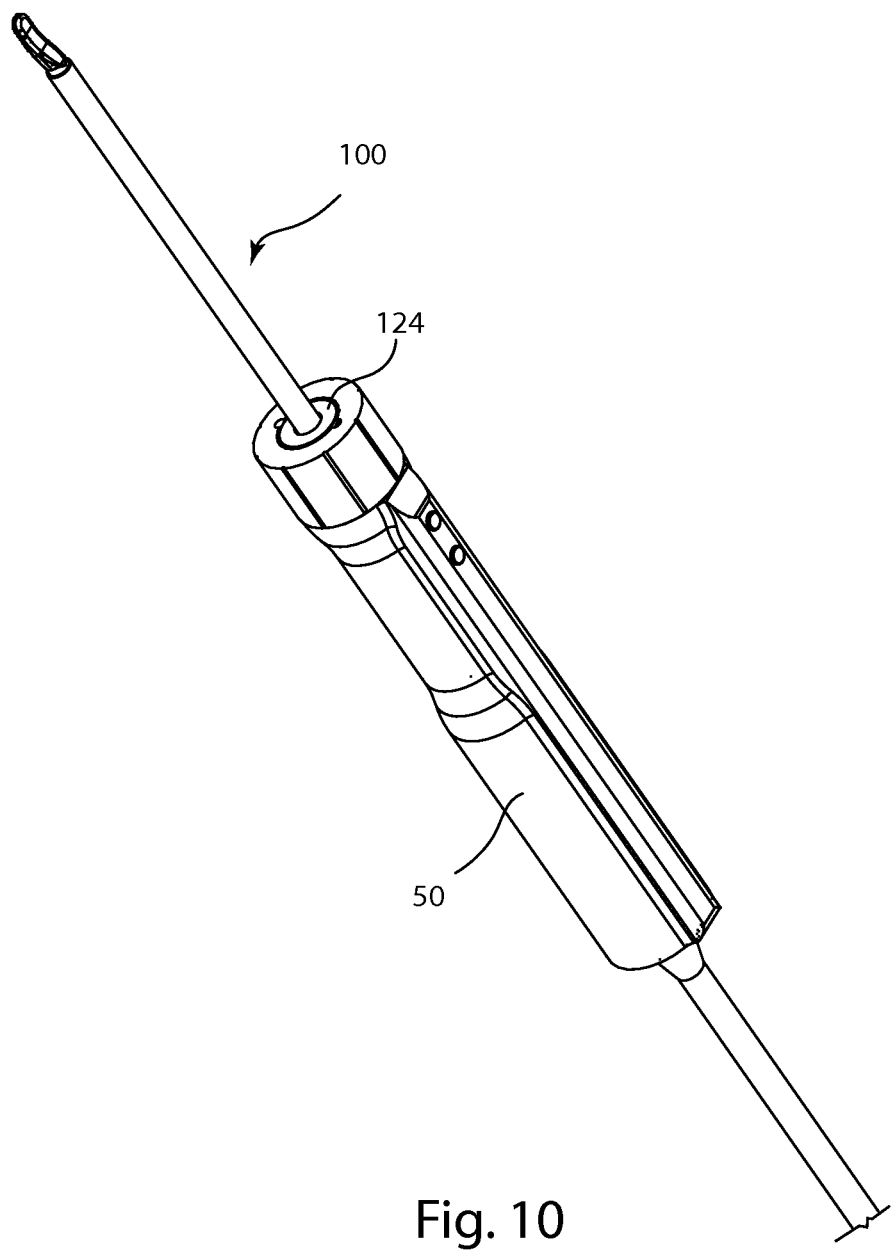
FIG. 10 is an isometric view of the rasping system of FIG. 1A coupled in an exemplary powered handpiece.

FIG. 10 illustrates rasp system 100 engaged in an exemplary powered rotary handpiece 50. Powered rotary handpiece 50 may be a handpiece known in the art, and provides rotary power and suction to rasp system 100. When the rasp system 100 is engaged in the handpiece, the handle portion 106 is surrounded by the handpiece as in FIG. 10, so that no rotating parts are exposed and so that debris pulled through the suction pathway is captured in the handpiece.

FIGS. 11A through 18B set forth alternate embodiments of the rasp head. It is appreciated that alternate embodiments of the rasp system may include any one of the rasp heads disclosed herein, and may include mixed and matched features of the various rasp heads.

Figure 11A:
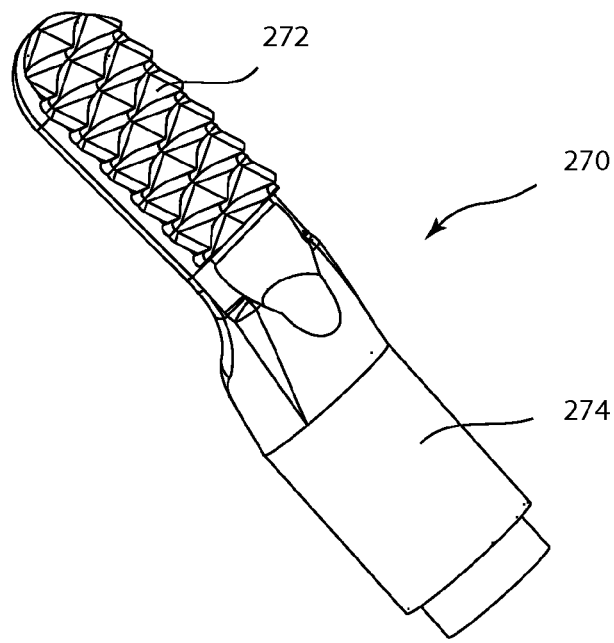
FIG. 11A is an isometric view of an alternate embodiment of a rasp head, a tissue removal portion angled relative to the remainder of the rasp head.
Figure 11B:
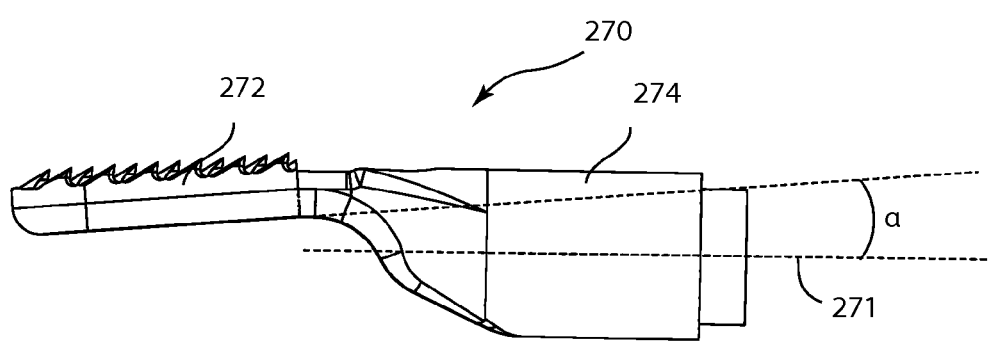
FIG. 11B is a side view of the rasp head of FIG. 11A.

FIGS. 11A and 11B depict a rasp head 270 comprising an angled working portion 272. The working portion 272 is tilted at angle α relative to a longitudinal axis 271 of a head shaft portion 274. Angle α may range from 1 to 10 degrees. More specifically, angle α may range from 3 to 7 degrees. Yet more specifically, angle α may be 5 degrees.

Figure 12A:
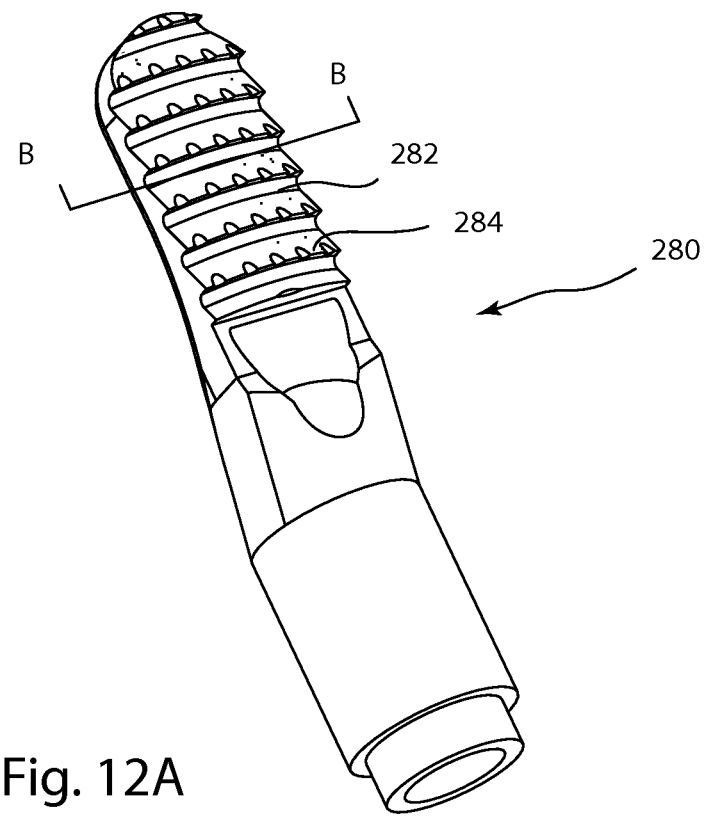
FIG. 12A is an isometric view of an alternate embodiment of a rasp head comprising a convex tissue removal surface.
Figure 12B:
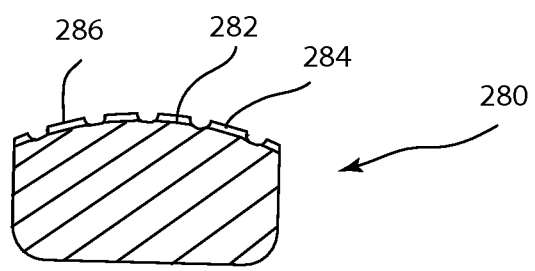
FIG. 12B is a cross-sectional view of the rasp head of FIG. 12A taken along line B-B.

FIGS. 12A and 12B depict a rasp head 280 comprising a convex tissue removal surface 282 from which teeth 284 project. The teeth may comprise straight or curved cutting edges 286; that is the cutting edges 286 may also be convexly curved.

Figure 13A:
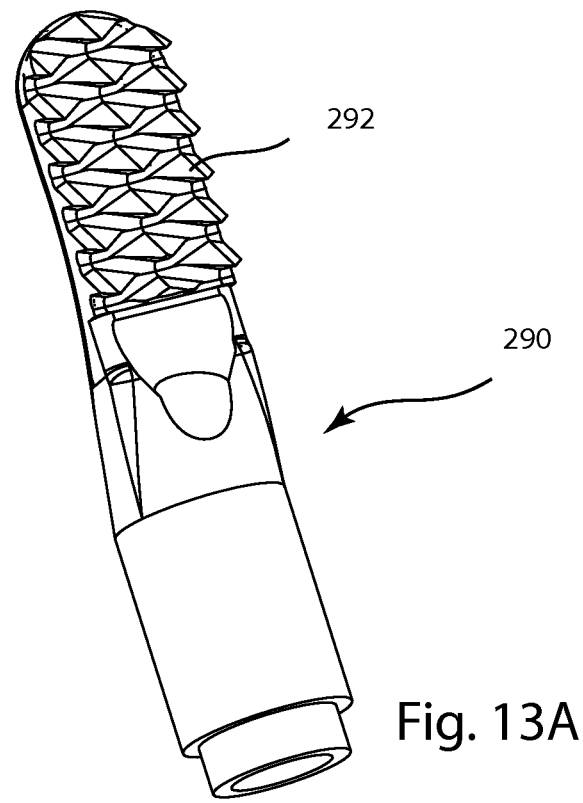
FIG. 13A is an isometric view of an alternate embodiment of a rasp head comprising elongated rasping teeth.
Figure 13B:
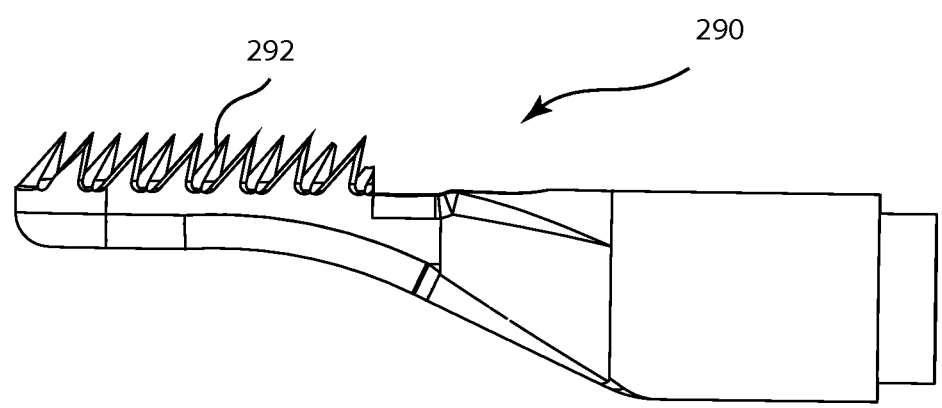
FIG. 13B is a side view of the rasp head of FIG. 13A.

FIGS. 13A and 13B depict a rasp head 290 comprising long teeth 292. The teeth 292 may be longer than teeth in other embodiments and may be advantageous for cutting through relatively softer materials.

Figure 14A:
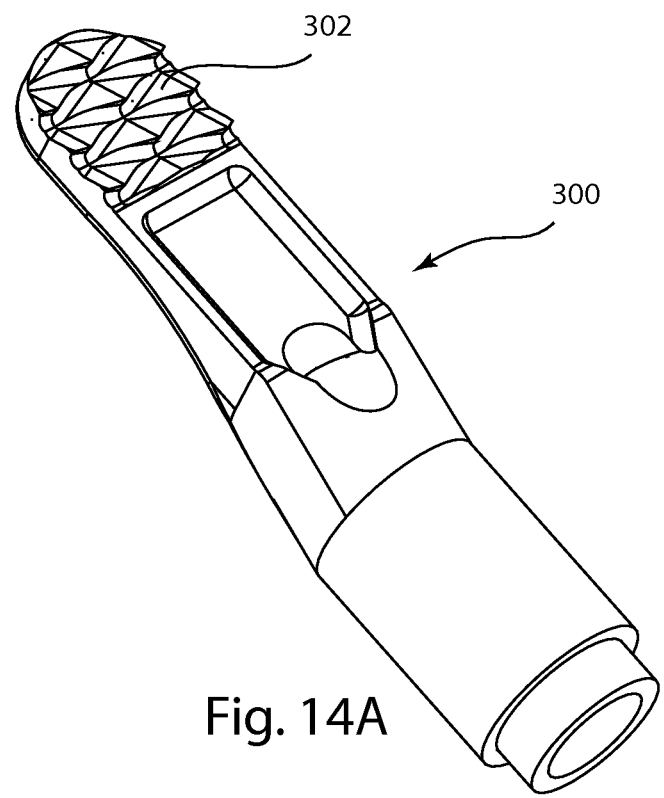
FIG. 14A is an isometric view of an alternate embodiment of a rasp head comprising a reduced tissue removal surface.
Figure 14B:
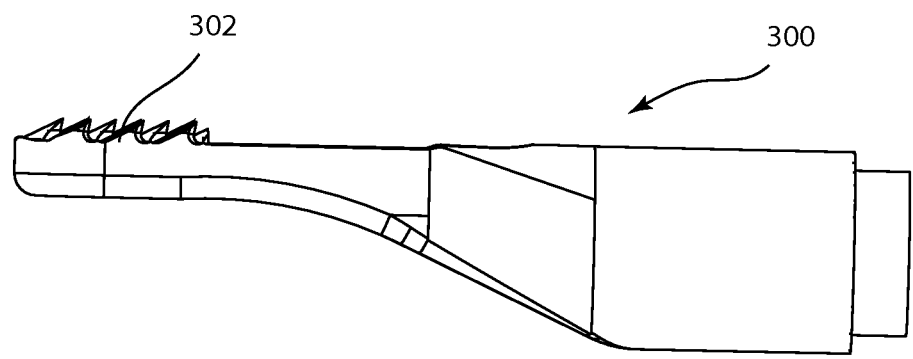
FIG. 14B is a side view of the rasp head of FIG. 14A.

FIGS. 14A and 14B depict a rasp head 300 comprising a relatively smaller tissue removal surface 302. This rasp head may be advantageous for accessing smaller and/or more confined areas such as the wrist joint, and for minimizing contact with tissues adjacent the area targeted for tissue removal. It is appreciated that in alternate embodiments, a smaller tissue removal surface may take the form of a longer but narrower tissue removal surface.

Figure 15A:
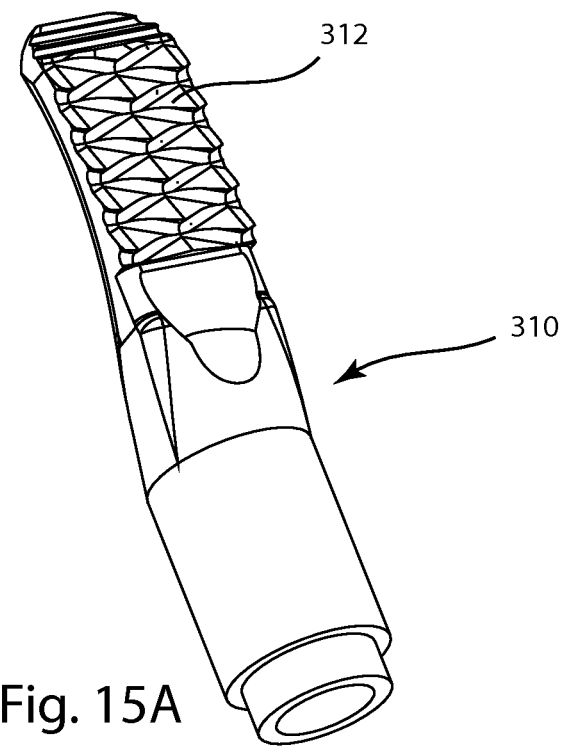
FIG. 15A is an isometric view of an alternate embodiment of a rasp head comprising a crescent-shaped tissue removal surface.
Figure 15B:
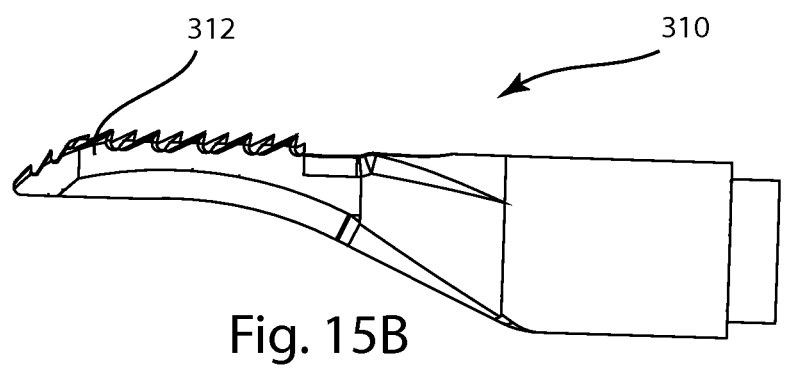
FIG. 15B is a side view of the rasp head of FIG. 15A.

FIGS. 15A and 15B depict a rasp head 310 comprising a curved or crescent-shaped tissue removal surface 312. Tissue removal surface 312 may be convexly curved longitudinally, or both longitudinally and transversely.

Figure 16A:
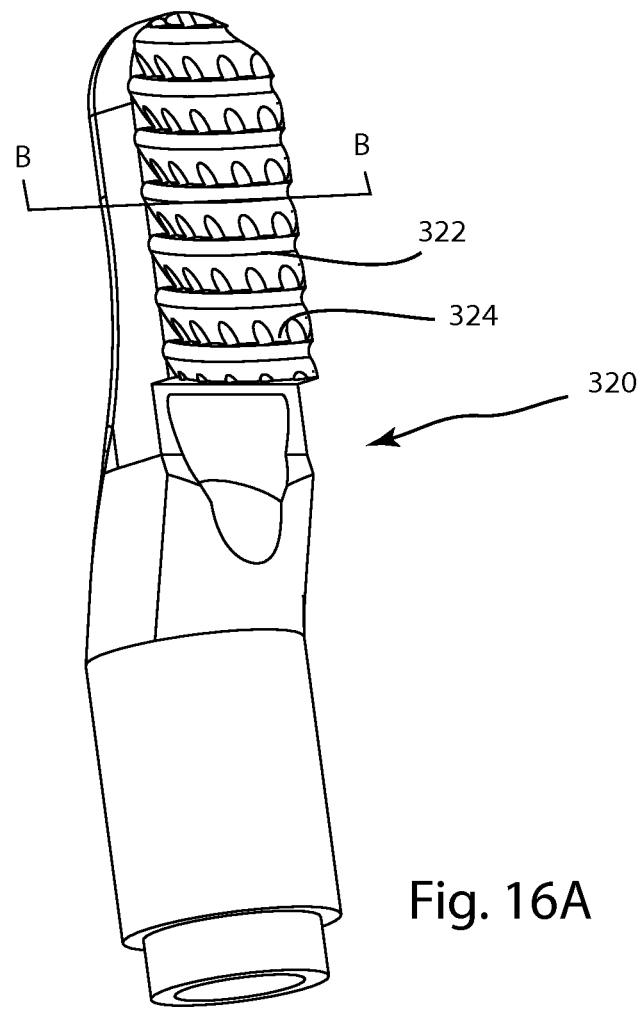
FIG. 16A is an isometric view of an alternate embodiment of a rasp head comprising a concave removal surface.
Figure 16B:
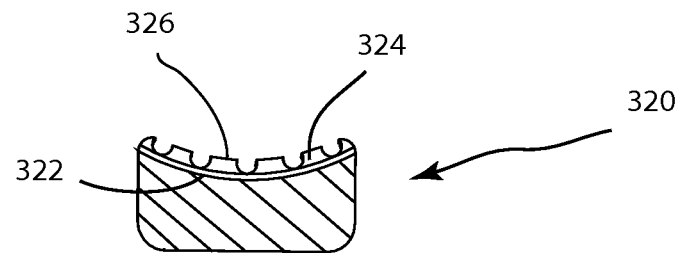
FIG. 16B is a side view of the rasp head of FIG. 16A.

FIGS. 16A and 16B depict a rasp head 320 comprising a concave tissue removal surface 322 from which teeth 324 project. The teeth may comprise straight or curved cutting edges 326; that is the cutting edges 326 may also be concavely curved.

Figure 17A:
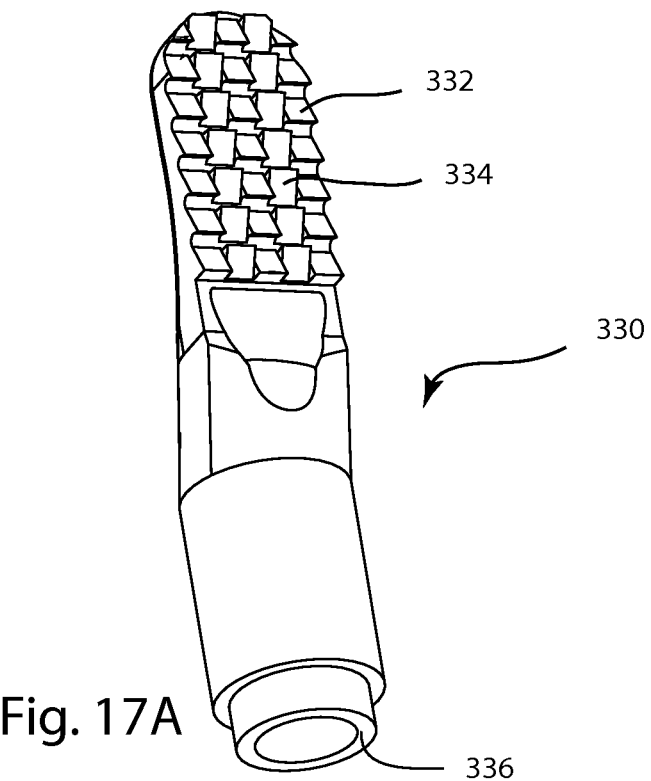
FIG. 17A is an isometric view of an alternate embodiment of a rasp head comprising bi-directional rasping teeth.
Figure 17B:
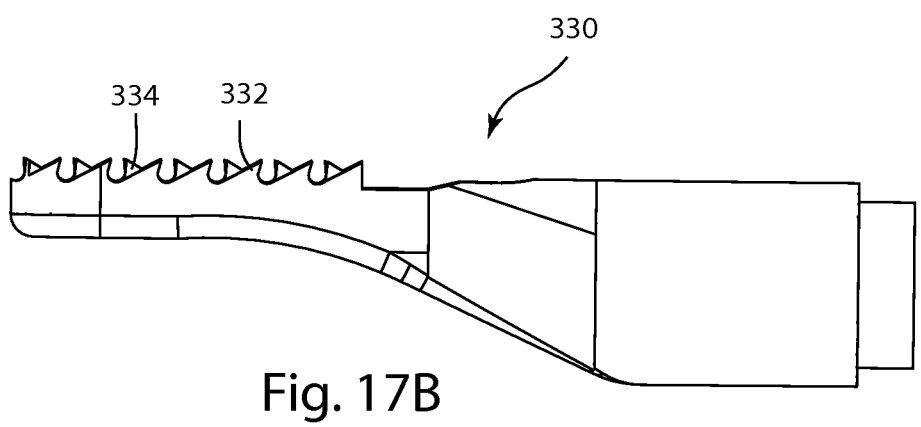
FIG. 17B is a side view of the rasp head of FIG. 17A.

FIGS. 17A and 17B depict a rasp head 340 comprising bi-directional teeth. A plurality of first teeth 332 are oriented proximally, or toward a proximal end 336 of the rasp head, while a plurality of second teeth 334 are oriented distally. When used as part of a reciprocating rasp system such as rasp system 100, tissue cutting may occur in both directions as the rasp head is axially reciprocated.

Figure 18A:
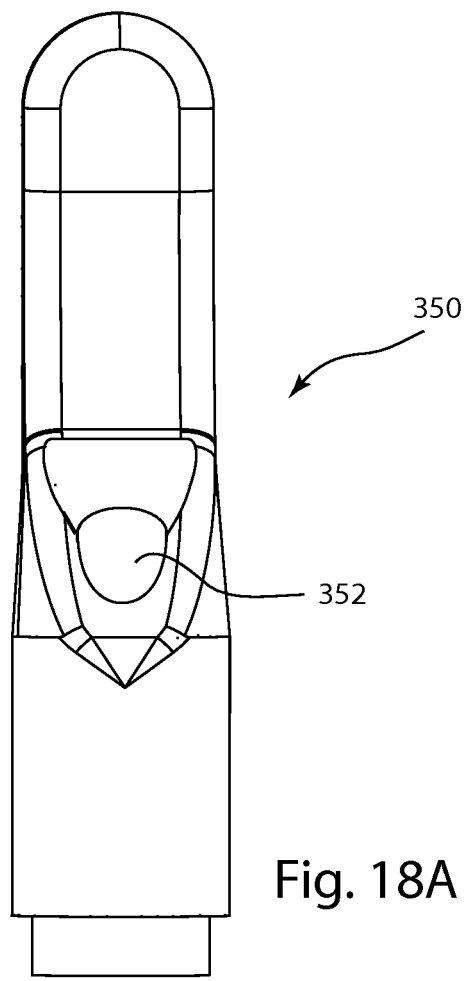
FIG. 18A is an isometric view of an alternate embodiment of a rasp head comprising a suction pathway opening on a back side of the head.
Figure 18B:
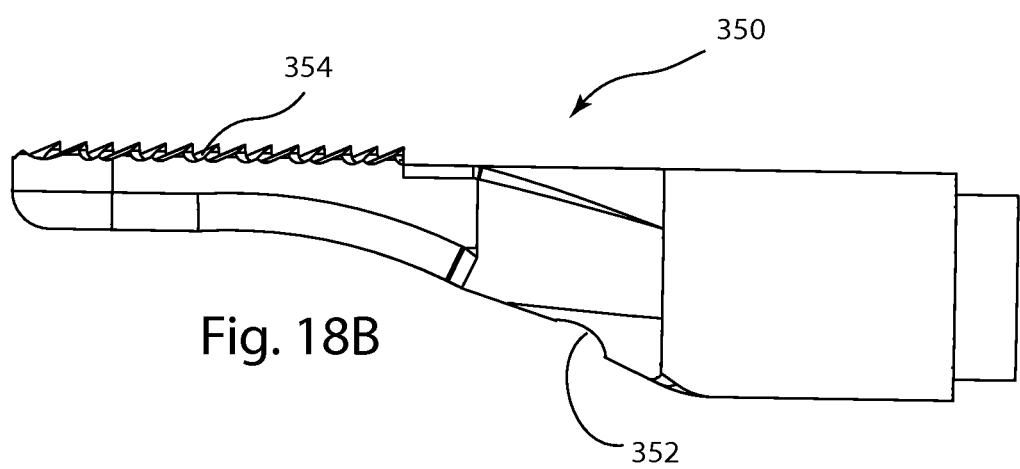
FIG. 18B is a side view of the rasp head of FIG. 18A.
Figures 19A, 19B, 19C:
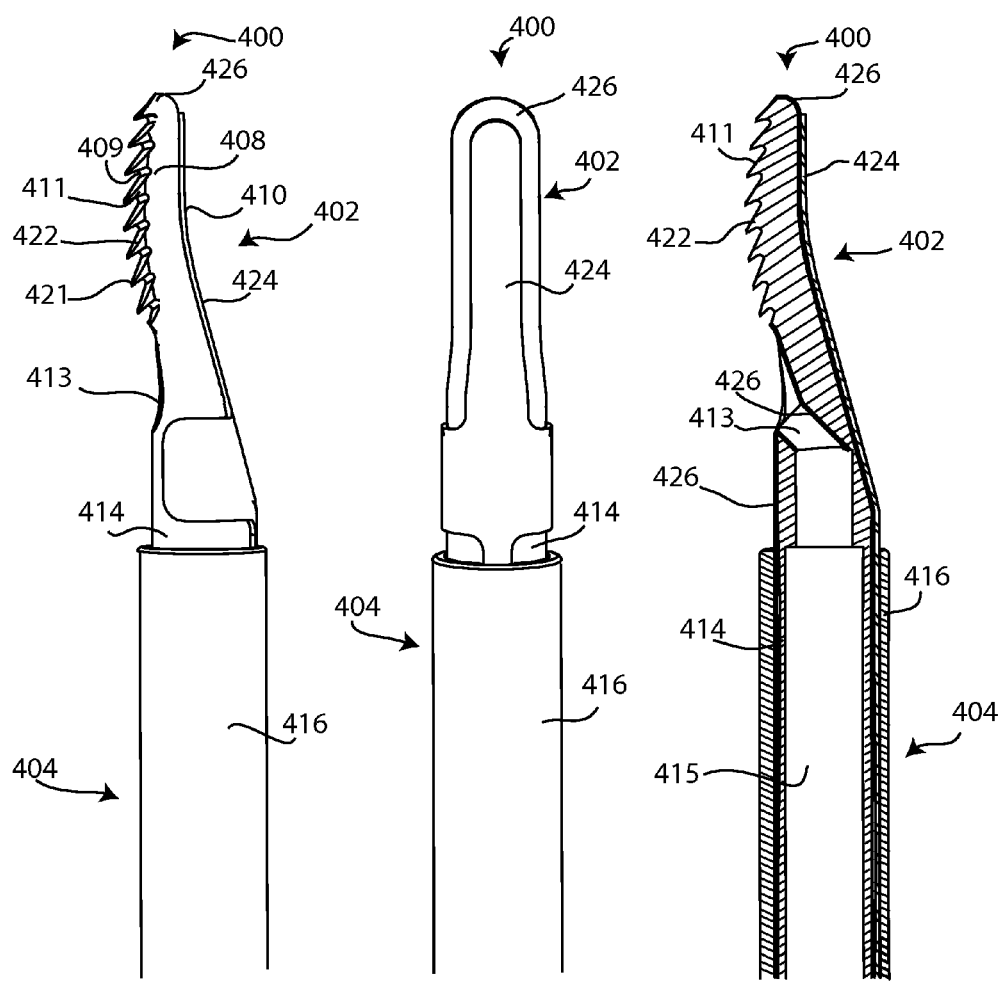
FIG. 19A is a side view of head and shaft portions of an RF/reciprocating rasp device including a rasp tissue removal surface, an ablation electrode integral with the tissue removal member, an insulating layer, and a return electrode.
FIG. 19B is a top view of the device of FIG. 19A.
FIG. 19C is a cross-sectional side view of the device of FIG. 19A.
Figure 20:
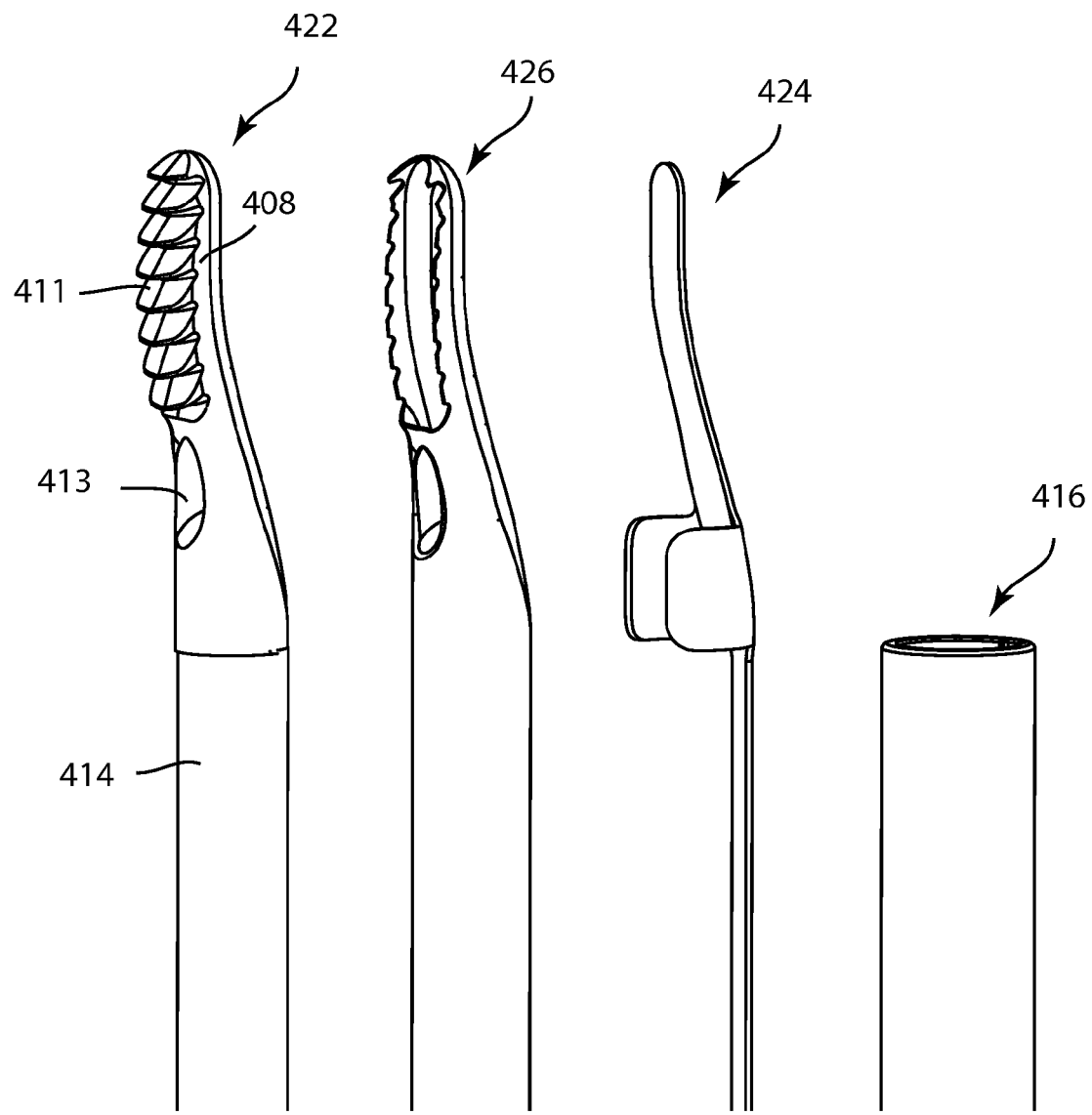
FIG. 20 is an exploded isometric view of the device of FIG. 19A including a tissue removal member which is integral with the ablation electrode, the insulating layer, the return electrode, and an outer sleeve.

FIGS. 18A and 18B depict a rasp head 350 comprising a suction pathway opening 352 located on the back of the rasp head, on the opposite side as a tissue removal surface 354. It is appreciated that any of the rasp head embodiments disclosed herein may include a similarly located suction pathway opening.

In the embodiments disclosed herein, the rasp head and reciprocating inner shaft may comprise stainless steel, titanium, or other metals or metal alloys. The outer sleeve may comprise metal, plastic, or polymer. The outer housing and rotating hub, and cam and cam follower surfaces, may each comprise polymer, plastic, metal, metal alloy, ceramic, polyether ether ketone (PEEK), thermoplastic polyetherimide (PEI) or a combination thereof. The hub may be coated to improve lubricity or contact strength.

Rasp system 100 may be used in a variety of methods for tissue removal and/or resurfacing. In general, rasp system 100 may be used for abrasionplasty, which encompasses both chondroplasty, or removal of cartilaginous material, and osteoplasty, or removal of bone material. Such tissue removal/resurfacing procedures may be carried out on any bone and/or joint. Similarly, rasp system 100 may be used in treatment of osteochondritis dissecans (OCD) on any affected bone to remove bone fragments. In addition to bone material, rasp system 100 may be used for resurfacing or removal of scar tissue, periosteum, fibrocartilage, functioning cartilage, or nucleus pulposus tissues. Rasp system 100 may also be used in resection and/or resurfacing of bone surfaces in preparation for re-attachment of tendons, preparation for joint fusion, or preparation for implantation of joint replacement device components. The rasp head 108 may be modified to produce alternative embodiments wherein: the size of the rasp head is varied in length, width, and/or thickness; the shape and dimensions of the rasping surface are varied; the number and/or rows of teeth are varied; and/or the orientation of the teeth is varied, among other variations. Rasp 100 and alternative embodiments may be used independently or with common surgical cannulas known in the art. Specific uses for the rasp system 100 and alternative embodiments are set forth herein, however it is appreciated that the rasp may be used in other tissue removal procedures within the scope of the invention.

In the joints of the ankle, rasp system 100 may be used to relieve anterior impingement by removing impinging osteophytes on the talus and/or tibia. Use of rasp system 100 may be advantageous over a burr, as a burr may penetrate too deeply into the bone cortex and cause a fracture in the talar neck. The smaller size and gentler action of rasp system 100 may result in a less aggressive approach than that provided with a burr. Rasp system 100 may also be used in the removal of chondrocytes to address chondromalacia of the talar dome and/or the tibial plafond. Medial and/or lateral guttural impingement of the ankle may be relieved by removal of osteophytes with rasp system 100. Depending on the size, shape and/or accessibility of the tissue to be removed, rasp system 100 comprising rasp head 108 which has a generally flat working surface may be used, or alternative embodiments comprising rasp head 310 with a crescent-shaped working surface or rasp head 280 with a convex working surface may be used.

Rasp system 100 may be used in procedures performed on the knee. Rasp system 100 may be used for symptomatic osteophyte removal, especially along the marginal articular edges of the joint. Rasp system 100 may be used for anterior cruciate ligament (ACL) notchplasty. For this procedure, it may be advantageous to use a system comprising rasp head 310 with a crescent-shaped working surface or rasp head 280 with a convex working surface. Also, a system using rasp head 270 with an angle of 3° to 5° may be ideal for notchplasty access. In addition, rasp system 100 or an alternate embodiment may be used in the knee to perform abrasionplasty to address OCD or chondromalacia.

In the hip, rasp system 100 may be used to address impingement by removal of bony prominences and/or osteophytes. Labral repairs may be performed, such as preparation of the acetabular rim for healing of a labral tear, as a non-limiting example. As in the ankle and knee joints, the rasp may used in the hip for removal of osteophytes and/or chondrocytes to address OCD or chondromalacia. In some procedures in the hip, an alternate embodiment of rasp system 100 comprising a curved shaft portion may be advantageous. In this embodiment the optional outer sleeve may not be required.

In the shoulder, rasp system 100 or alternate embodiments may be used to remove bone and/or cartilage material in at least the following procedures: acromial clavicular joint resection (also known as the Mumford procedure or AC resection); subacromial decompression; glenoid rim abrasionplasty; and osteoplasty in preparation for rotator cuff reattachment.

In the spine, rasp system 100 may be used in vertebral endplate abrasionplasty, and in preparation for vertebral fusion or artificial disc implantation. Around the facet joints, rasp system 100 may be used for removal of bone spurs, and preparation of articular surfaces for facet joint fusion or replacement. Especially along the curved surfaces around the facet joints, a rasping system comprising the crescent, convex or concave shaped rasp head may be advantageous. Also, the rasp may be used to remove osteophytes or bony prominences in or around the spinal canal.

For procedures in joints of the wrist, a smaller working head surface such as that in rasp head 300 may be advantageous for reaching into confined areas without disturbing adjacent soft tissues. Rasp system 100 may be used for chondroplasty, osteoplasty and other joint preparation procedures in the wrist.

In the elbow, rasp system 100 or alternate embodiments may be used to remove osteophytes on the edges of the trochlea, to prevent impingement on the ulnar nerve. Marginal osteophytes or bony prominences may be removed at the marginal edges of the articulating surfaces of the elbow. For treatment of arthritis, bone spurs may be removed to aid in restoring motion. As with the wrist, use of a system comprising rasp head 300 with a reduced tissue removal surface may be advantageous, as may use of a system comprising a convex or crescent shaped head.

In the skull, rasp system 100 may be employed for sculpting of bony prominences on the cheek areas, forehead, nose, chin and jaw.

Additional embodiments of a reciprocating surgical instrument include jaw members which cooperate to provide biting or nipping action. The reciprocating motion allows these instruments to move between open and closed positions. In the open position, the jaw members may be spaced apart, and may be distally displaced from the instrument. In the closed position, the jaw members may abut one another, and may be pulled toward the instrument. The open jaw members may be urged around targeted tissue so that when the jaws move to the closed position, they grasp and/or sever the tissue. Suction may be provided to remove the severed tissue. An opening to a suction path may be located between the jaws.

Removal of soft tissues adjacent to articular joints is often necessary to gain access to the joint space. For example, in a hip or shoulder arthroscopy procedure, the ligaments forming the joint capsule may need to be resected or penetrated to clear a pathway for a surgical instrument to reach the joint. Disclosed herein are embodiments of a reciprocating rasp system which includes integral RF ablation capability, allowing a practitioner to use a single instrument for RF ablation or coagulation of soft tissues, and removal of hard or bony tissues. The localized RF current flow provided by the instruments disclosed herein may vaporize soft tissues to which it is applied. Use of the combined rasp/RF instrument may provide advantages including: the need for fewer portal incisions, which may reduce patient pain and/or healing time; reduced complexity of the procedure, since fewer individual instruments are required; reduced tissue trauma, as fewer instruments are moved in and out of the affected area, and reduced cost.

FIGS. 19A-24 illustrate embodiments of reciprocating rasp systems with integrated RF ablation capability. Although not all possible combinations are shown, it is appreciated that an RF/rasp system may include any of the reciprocating rasp variations disclosed herein, with any of the rasp head configurations disclosed herein. Referring to FIGS. 19A-19C and 20, one embodiment of an RF/rasp device 400 includes a head portion 402, shaft portion 404, and handle portion 406 (not shown, but may include the same components as handle portion 106 or other handle portions described herein). The head, shaft and handle portions of system 400 may be the same as other head, shaft and handle portions disclosed herein, with the addition of an RF ablation system 420 integrated into the device. Head portion 402 includes rasp head 408, which has a first side 409 and a second side 410 opposite the first side. A tissue removal surface 411 and suction opening 413 for a suction pathway are located on the rasp head 408. A tissue removal member 412 comprises rasp head 408 and inner shaft 414, and may further include portions of the RF ablation system 420. Shaft portion 404 includes inner shaft 414 and outer sleeve 416, and may further include portions of the RF ablation system 420. A suction pathway 415 comprising distal suction opening 413 and a proximal opening on the hub in the handle portion 406 extends through device 400. Tissue removal surface 411 may comprise a plurality of teeth 421 for cutting and removing hard tissue.

The RF ablation system 420 includes an ablation electrode 422, a return electrode 424, and may include an insulation layer 426 positioned between the ablation and return electrodes. RF system 420 may be described as a bi-polar RF system. In this embodiment of FIGS. 19A-20, the ablation electrode 422 is co-located with the rasp head 408 and inner shaft 414. Insulation layer 426 coats a majority of rasp head 408, except where tissue removal surface 411 protrudes from the insulation, so that when the ablation system is powered or energized, RF energy is transmitted from the tissue removal surface 411, effectively making tissue removal surface 411 the active ablation electrode. The portion of the ablation electrode which protrudes from the insulation may be referred to as the active ablation portion of the ablation electrode. The insulation layer 426 may also coat all or a portion of the length of the inner shaft 414, and may coat a portion of the suction opening 413, as shown. The RF ablation system 420 is connected to a power source and a controller for controlling transmission of RF current through the system. The controller may be a switch, knob, pedal, lever, dial, button or other suitable control member, located on the powered rotary handpiece 50, or on a separate control apparatus. The RF probe may be powered via the controller on to transmit RF current simultaneously with reciprocation of the tissue removal member; alternately, it may be turned on and off independently of tissue removal member reciprocation. The exposed, or uninsulated surface area of the return electrode 424 may be referred to as the active return portion of the return electrode, and is at least three times greater than the exposed surface area, or active ablation portion, of the ablation electrode 422. The ridges of the rasp teeth on the tissue removal surface may enhance arcing of RF current transmitted from the active ablation portion of the ablation probe.

In a method of use, a practitioner may insert head portion 402 into a targeted area, position tissue removal surface 411 adjacent soft tissues to be treated, activate the RF system 420 to ablate or coagulate soft tissue with RF current flow from the ablation electrode 422 to clear a pathway to a joint, turn off the RF system, position the tissue removal surface 411 adjacent hard tissues to be removed, then power the reciprocating motion to use the tissue removal surface 411 to treat adjacent hard tissue. Soft tissues to be removed through ablation or coagulation may comprise muscle, skin, fascia, blood vessels, ligamentous or other relatively soft tissues, while hard tissues may comprise bone, scar tissue, periosteum, fibrocartilage, functioning cartilage, nucleus pulposus tissues, or other relatively hard tissues. The RF current flow may also cauterize blood vessels and/or coagulate blood flow. Alternatively, RF ablation and rasp reciprocation may be powered simultaneously to remove hard and soft tissues at the same time. Suction may be provided as needed, simultaneously with or independently between RF ablation and rasp reciprocation functions. The suction may pick up loose tissue particles or resected pieces of tissue, remove bubbles created by tissue ablation or blood vessel cauterization/coagulation, and/or help maintain visualization of the surgical site. All of these functions may be accomplished without removal of the head portion 402 from the surgical site. Of course, the functions may be accomplished in any desired order and may be repeated as necessary.

The RF current flow may be provided at selected settings, or power levels to produce the desired results, for example, a higher power level may be used to destroy soft tissues while a lower power level is sufficient for cauterization/coagulation of blood vessels. The overall wattage range of the RF system may be 0 to 300 watts. More specifically, a setting or power level for tissue ablation may be three to four times higher than a setting for blood vessel cauterization or blood coagulation. Yet more specifically, a setting for cauterization/coagulation may be 50 watts, and a setting for tissue ablation may be 200 watts.

Figure 21A:
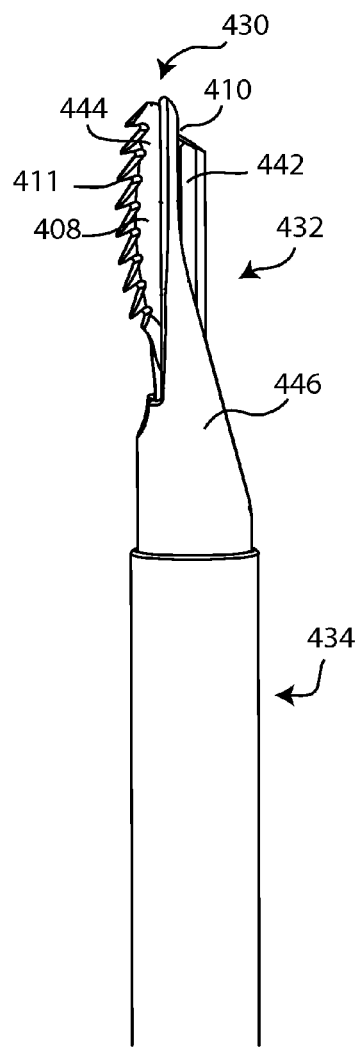
FIG. 21A is a side view of head and shaft portions of an RF/reciprocating rasp device including a tissue removal member comprising a rasp head having a tissue removal surface, an ablation electrode positioned on a back side of the rasp head, an insulating layer, and a return electrode integral with the tissue removal surface, and an outer sleeve.
Figure 21B:
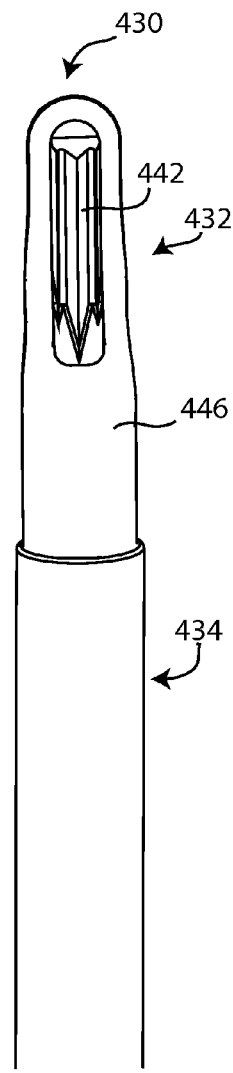
FIG. 21B is a top view of the device of FIG. 21A.
Figure 21C:
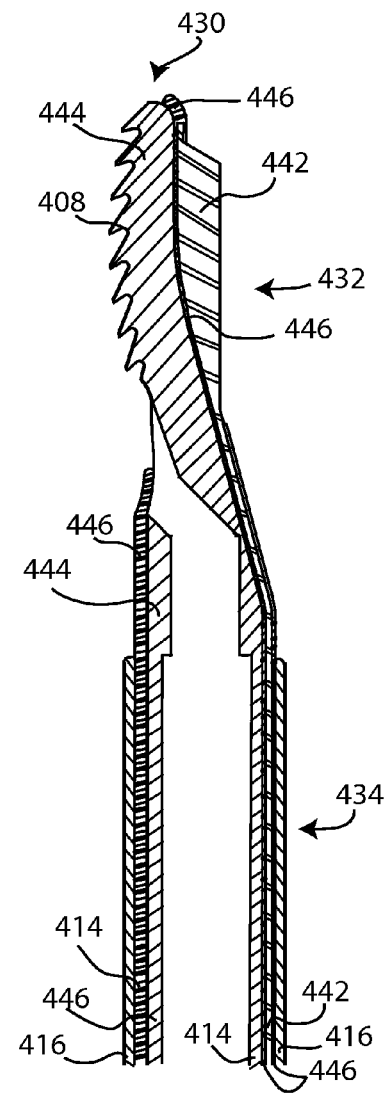
FIG. 21C is a cross-sectional side view of the device of FIG. 21A.
Figure 22:
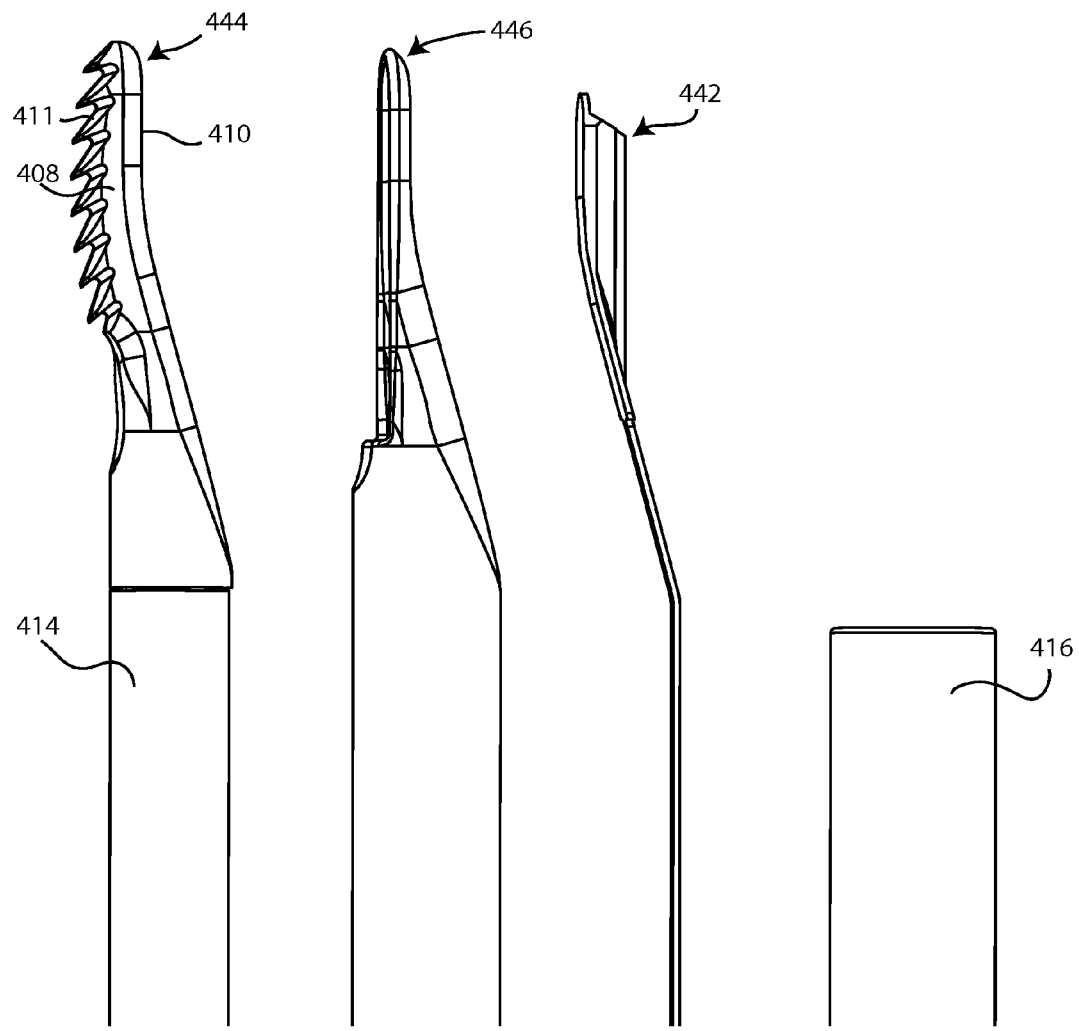
FIG. 22 is an exploded side view of the device of FIG. 21A including the rasp head and inner shaft integral with the return electrode, the insulating layer, the ablation electrode, and the outer sleeve.

Another embodiment of a reciprocating rasp system with an integral RF ablation system is shown in FIGS. 21A-22. The RF/rasp device 430 includes head portion 432, shaft portion 434, and handle portion 436 (not shown, but may include the same components as handle portion 106 or other handle portions described herein). The device further includes RF ablation system 440, which includes an ablation electrode 442, a return electrode 444, and may include an insulation layer 446 positioned between the ablation and return electrodes. Insulation layer 446 may also be between the ablation electrode 442 and the outer sleeve 416, and between the return electrode 444 and the outer sleeve 416, and may extend the length of the shaft portion 434. In this embodiment of FIGS. 21A-22, the ablation electrode 442 is positioned or carried on a second 410, or back side of rasp head 408. Insulation layer 446 coats a majority of rasp head 408, except where return electrode 444 protrudes from the insulation 446, at tissue removal surface 411, effectively making tissue removal surface 411 the active return electrode. The exposed, or uninsulated surface area of the return electrode 444 is at least three times greater than the exposed surface area of the ablation electrode 442. Ridges or other protrusions formed on the ablation electrode 442 may enhance arcing of electrical energy transmitted from the ablation electrode. The device 430 may further include a suction pathway and suction capabilities as described for other embodiments. Methods of use may be the same as those described for previous embodiments.

Figure 23A:
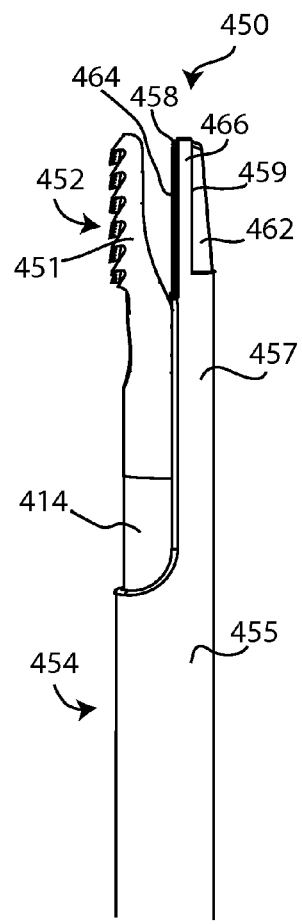
FIG. 23A is a side view of head and shaft portions of an RF/reciprocating rasp device including a tissue removal member comprising a rasp head having a tissue removal surface, an outer sleeve having an extension, an ablation electrode positioned on a first side of the sleeve extension, a return electrode integral positioned on a second side of the sleeve extension, and an insulating layer.
Figure 23B:
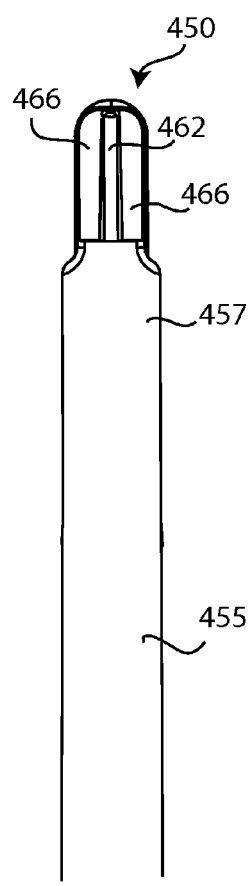
FIG. 23B is a top view of the device of FIG. 23A.
Figure 23C:
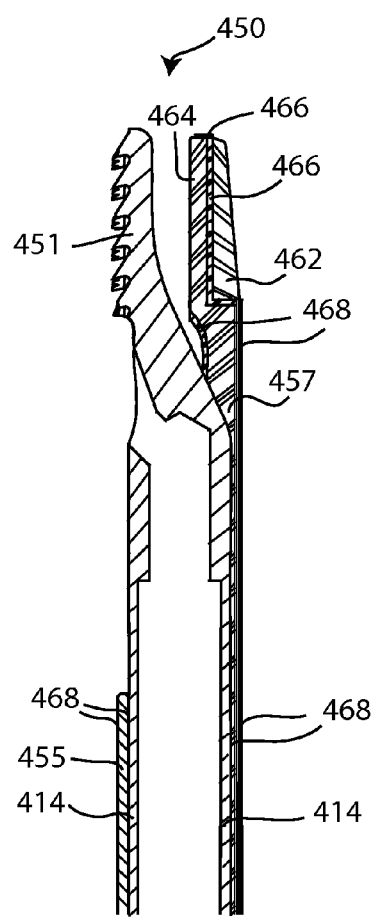
FIG. 23C is a cross-sectional side view of the device of FIG. 23A.
Figure 24:
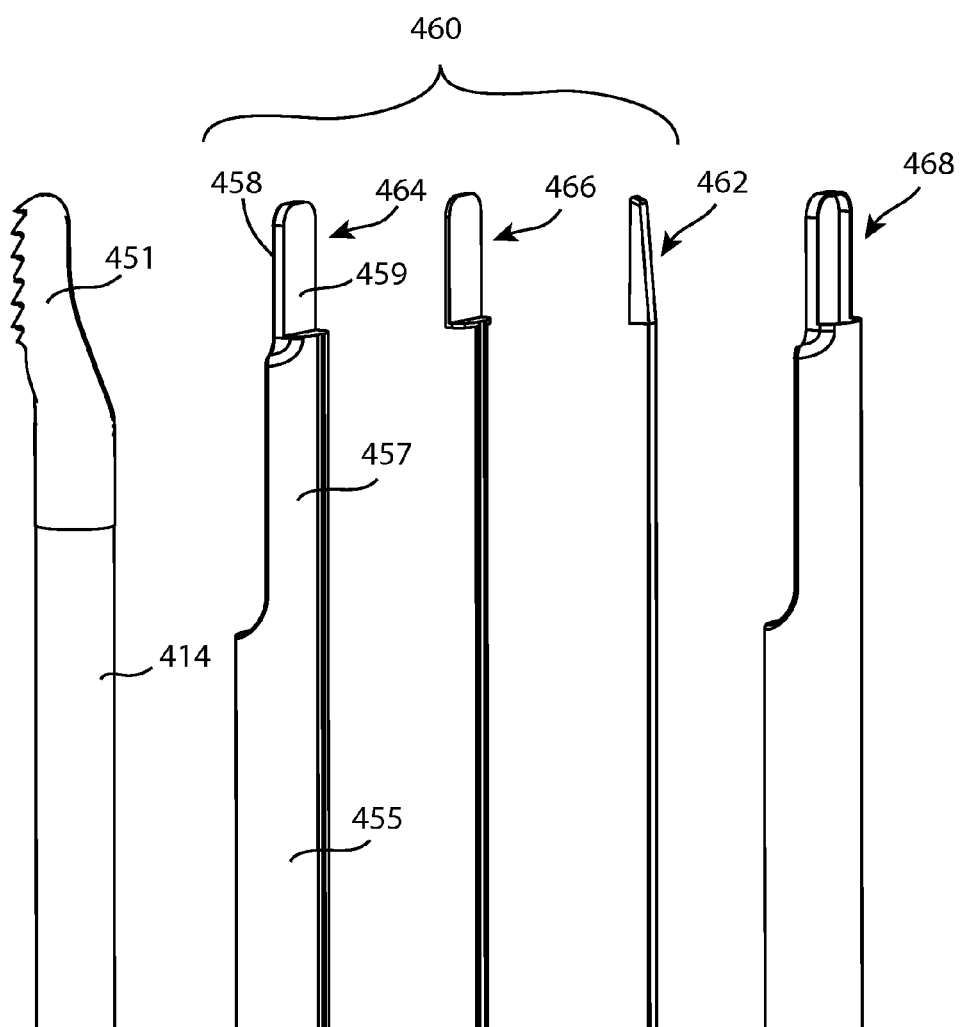
FIG. 24 is an exploded side view of the device of FIG. 23A.

Yet another embodiment of a reciprocating rasp system with an integral RF ablation system is shown in FIGS. 23A-24, in which the ablation and return electrodes are carried on the rasp system stationary outer sleeve. The RF/rasp device 450 includes head portion 452, shaft portion 454, and handle portion 456 (not shown, but may include the same components as handle portion 106 or other handle portions described herein). A reciprocating rasp portion includes rasp head 451 and inner shaft 414. It is appreciated that rasp head 451 may comprise any of the rasp heads disclosed herein and may include features including, but not limited to, teeth or other tissue removal surface, suction opening(s), and a suction pathway. An outer sleeve 455 includes a sleeve extension 457 which projects distally from the tubular portion of the sleeve, and has an inner or first side 458 and an outer or second side 459. The device further includes RF ablation system 460, which includes an ablation electrode 462, a return electrode 464, and an insulation layer 466 positioned between the ablation and return electrodes. In this embodiment of FIGS. 23A-24, the RF system is positioned or carried on the extension 457 of outer sleeve 455. Ablation electrode 462 is carried on the second side 459 of the sleeve extension 457, and may be fin-shaped. Return electrode 464 is integral with sleeve extension 457, and is exposed from the insulation on the first side 458 of the sleeve extension. Insulation layer 466 is sandwiched between the ablation and return electrodes. In this embodiment, sleeve 455 may be coated by a second insulation layer 468 on both the inside and the outside of the sleeve, to isolate it from inner shaft 414. The second insulation layer 468 may also fall outside of the ablation electrode 462, at least along shaft portion 454. Along the shaft portion 454, the ablation electrode 462 is sandwiched between insulation layers 466, 468. The exposed, or uninsulated surface area of the return electrode 464 is at least three times greater than the exposed surface area of the ablation electrode 462. Fins, ridges or other protrusions formed on the ablation electrode 462 may enhance arcing of electrical energy transmitted from the ablation electrode. The device 450 may further include a suction pathway and suction capabilities as described for other embodiments. Methods of use may be the same as those described for previous embodiments.

Suitable materials for the ablation and return electrodes of the RF systems disclosed herein include but are not limited to stainless steel, tungsten, and other conductive materials, metals or metal alloys. Suitable materials for the insulation layers include but are not limited to polytetrafluoroethylene (PTFE), polyolefins, acrylic, polycarbonate, acrylonitrile butadiene styrene (ABS), plastics, and other insulating materials.

Other embodiments of reciprocating rasp system may include imaging, navigation, and/or infusion capabilities. Referring to FIGS. 25A-25C, rasp system 470 includes imaging and/or navigation capabilities. System 470 comprises head portion 472, shaft portion 474, and handle portion 476. Head portion 472 includes a reciprocating rasp head 478, which may comprise any of the rasp heads disclosed herein, including rasp heads with RF ablation capability. Adjacent head portion 472 is auxiliary device 480. Auxiliary device 480 may be received in a housing 482. Auxiliary device 480 may include an imaging instrument, which may be a camera, ultrasound transmitter, light transmitter, or other imaging transmitter or scanner. In another embodiment, auxiliary device 480 may include a computer-aided navigation reference marker, which may be used in conjunction with a fluoroscopic C-arm and anatomic reference markers to provide intraoperative fluoroscopic images. Auxiliary device 480 may be fixed in housing 482, or may be mobile, able to extend out of housing 482 at any angle. Auxiliary device 480 may be rotatable and sufficiently mobile to capture a 360° view of the environment surrounding the rasp head. For example, auxiliary device 480 may be coupled to a flexible shaft 484, allowing the device 480 to extend and retract in and out of housing 482, and bend around head 478. In the embodiment shown, housing 482 is formed on outer sleeve 116; it is appreciated that the housing may be located at any position relative to head 478, whether laterally adjacent, inferior, or superior to the head. In another embodiment, housing 482 may be integrally formed or co-located with head 478. An auxiliary sleeve portion 486 may be formed on outer sleeve 116 and include an auxiliary bore 488. Wiring and controls for auxiliary device 480 may pass through bore 488.

An infusion system may be integrated into any of the rasp systems disclosed herein. FIGS. 26A-26C illustrate one embodiment of such a system. Rasp system 490 includes an RF ablation system 420, auxiliary device 480, and infusion port 492. Infusion port 492 may be positioned adjacent the rasp head 408, providing an opening through which saline or other fluids may be pumped to infuse a targeted site. An infusion bore 494 may open into auxiliary bore 488 as shown or may remain separate. Flexible or rigid tubing may extend through infusion bore 494 to infusion port 492, providing a path for the fluid from a fluid source to the port. By way of non-limiting example, the infusion system may introduce saline, pain relief medication, bone morphogenic protein, bone growth stimulator, anesthetic agents, analgesic agents, anti-inflammatory agents, anti-rejection agents, growth factors, antibiotics, anti-adhesion factors, saline, glycosaminoglycan varieties, collagen varieties, bio-nutrients, gene-delivery vehicles, stem cells, and/or any other therapeutic substance that is desirable to be dispensed to the surgical site. Infusion may be used in conjunction with the suction capabilities of the rasp system, or separately.

Figure 27:
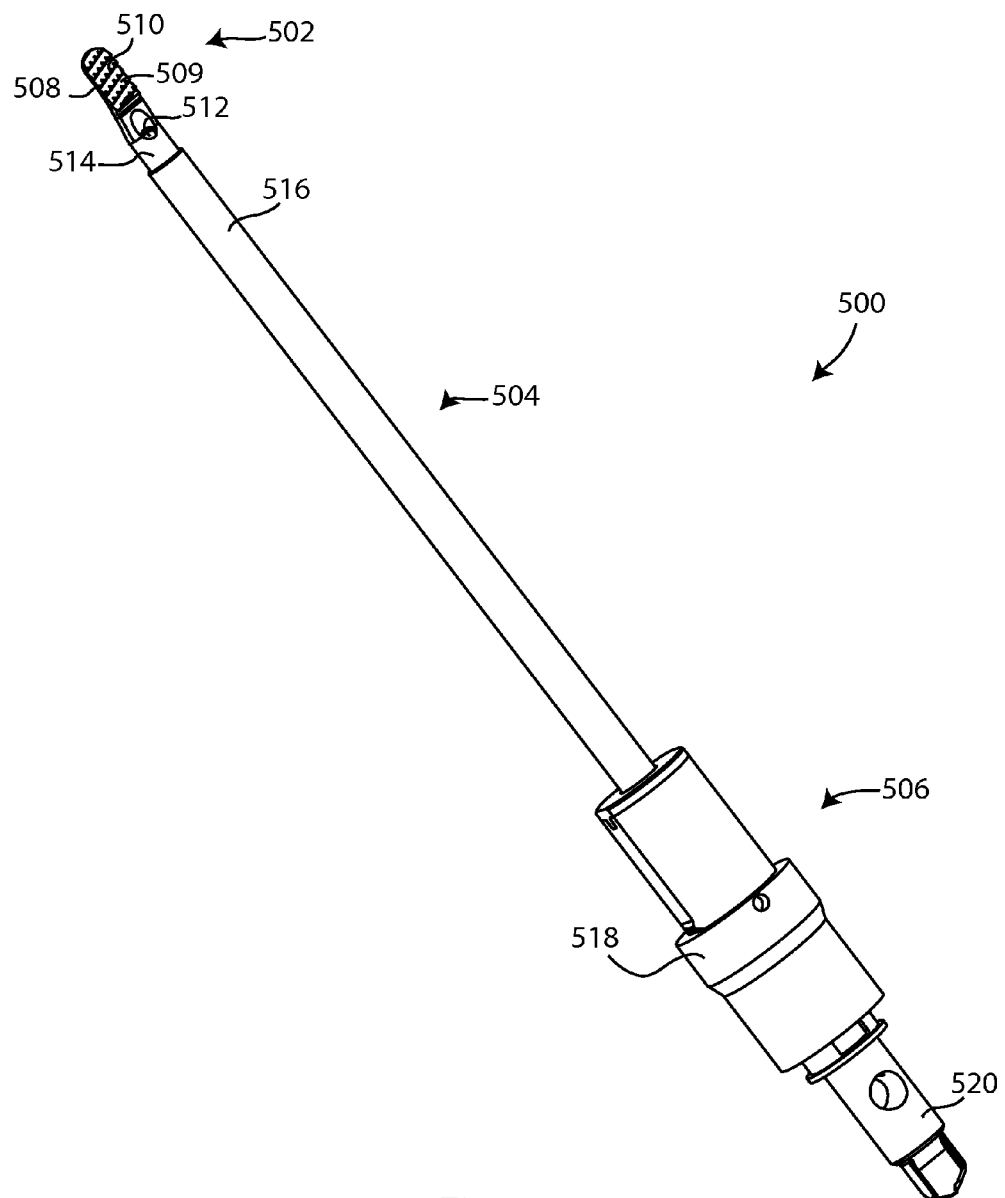
FIG. 27 is an isometric view of an alternate embodiment of a reciprocating rasping rasping system including a head portion, a shaft portion, and a handle portion.

FIGS. 27-33 illustrate an embodiment of a reciprocating rasp system which includes an alternate embodiment of a motion conversion mechanism for converting rotary to reciprocating motion. Referring to FIG. 27, rasp system 500 is shown in an isometric view. Rasp system 500 comprises head portion 502, shaft portion 504, and handle portion 506. Head portion 502 comprises rasp head 508, which includes a tissue removal surface 509 having a plurality of teeth 510 or cutting edges which may cut anatomical tissues when drawn along the tissue surface. A suction opening 512 is located on the head portion 502, and may be disposed between the teeth and the shaft portion. The shaft portion 504 comprises inner shaft 514 which extends proximally from the rasp head 508 and is received in the handle portion 506. Inner shaft 514 is hollow, having a bore 515 (not visible in FIG. 27, seen in FIG. 29) extending from suction opening 512 to a proximal end of the inner shaft, the bore 515 forming a portion of a suction pathway. The inner shaft 514 extends through an optional outer sleeve 516 which is joined to the handle portion 506. Handle portion 506 includes a outer housing 518 which encloses a cam 524 and a fixed cam (within housing 518; not visible in FIG. 27) and partially houses a rotatable hub 520 which is coupled to the cam. When handle portion 506 is engaged in a powered rotary handpiece and power is supplied, hub 520 rotates and consequently cam 524 also rotates, and the cam and fixed cam provide a motion conversion mechanism which converts the rotary motion of the hub to axial reciprocal motion of the inner shaft 514 and attached head 508. Hub 520 may also be referred to as a sluff chamber.

Figure 28A:
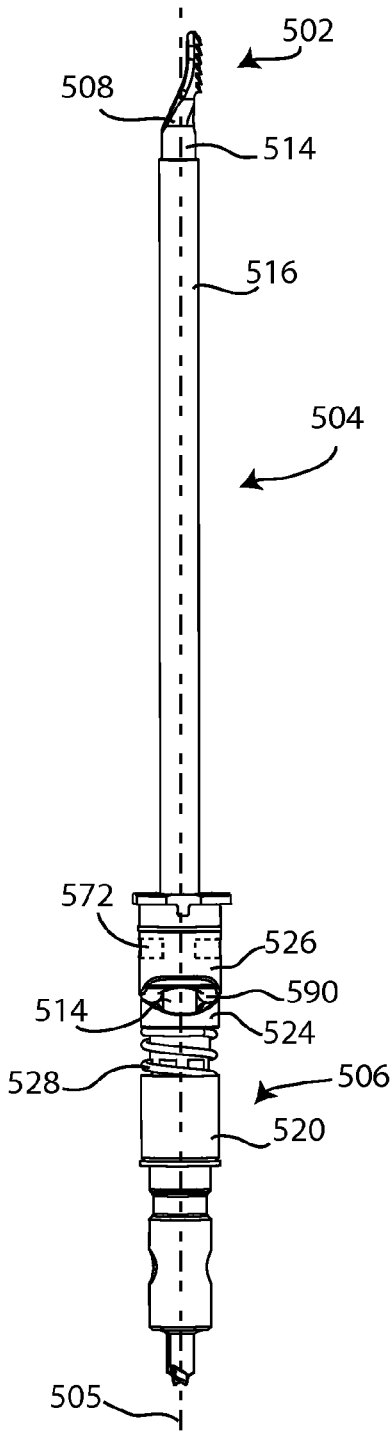
FIG. 28A is a side view of the rasping system of FIG. 27, with an outer housing removed.
Figure 28B:
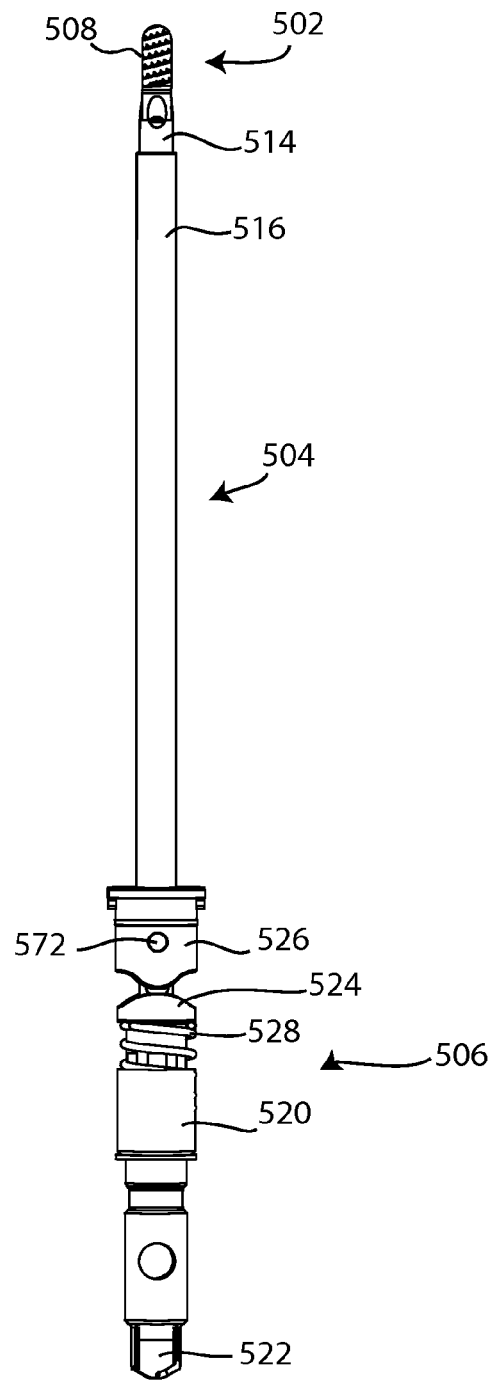
FIG. 28B is a bottom view of the rasping system of FIG. 24A.
Figure 29:
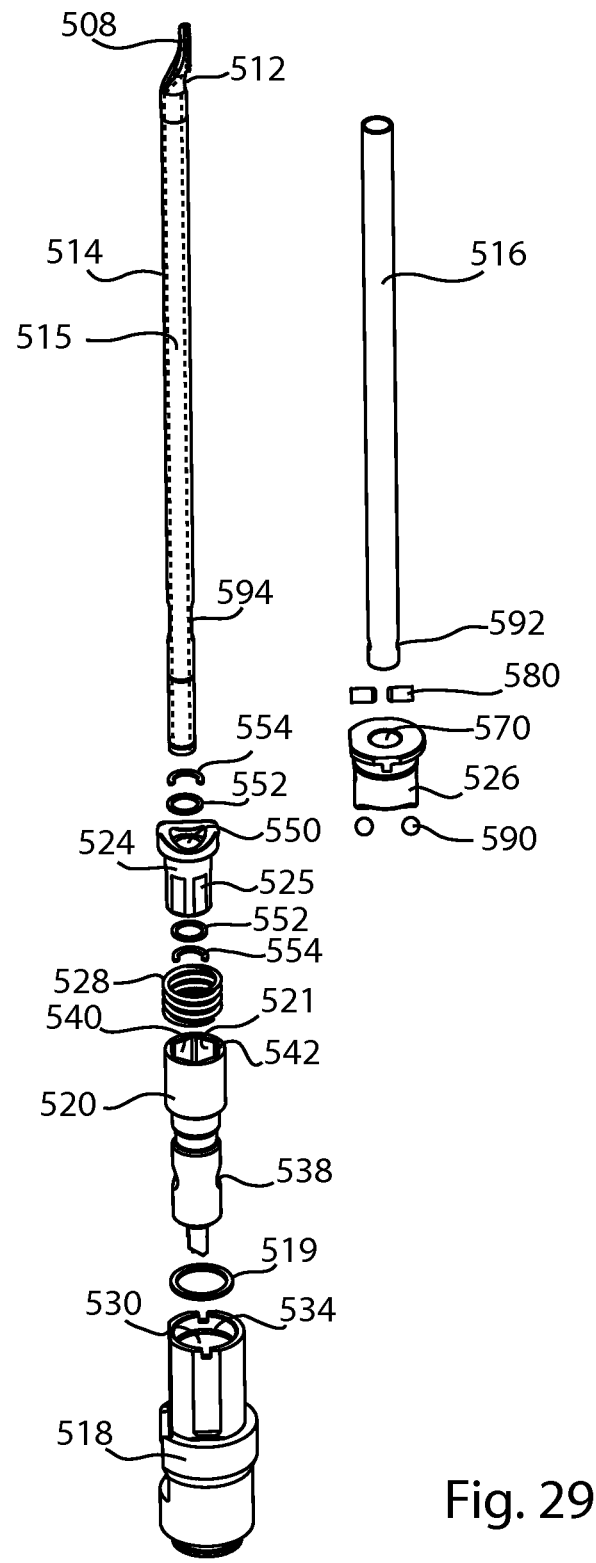
FIG. 29 is an exploded view of the rasping system of FIG. 27.

FIGS. 28A and 28B show side and bottom views of rasp system 500, respectively. The outer housing 518 is not shown so that the juxtaposition of the component parts may be seen, relative to longitudinal system axis 505. FIG. 29 is an exploded isometric view of the system. With reference to these drawings, system 500 will be described in a generally proximal to distal sequence. At the proximal end of the assembled system, hub 520 includes a driver connection 522, which may be a tab shaped to be coupled with a driver in a powered handpiece, as described earlier with reference to system 100. When hub 520 is received in housing 518 as in FIG. 27, a coupler washer 519 located between hub 520 and housing 518 promotes free rotation of the hub relative to the housing, thus reducing friction and potentially preventing melting of the two components. Hub 520 further includes a connection feature 521 shaped to receive the cam 524 in a sliding connection, wherein cam 524 is partially captured in hub 520 so that it is rotatably carried with the rotation of hub 520 about longitudinal axis 505, but can also reciprocate along axis 505. The connection feature 521 may be a hex feature, and cam 524 has a corresponding connection feature 525. Inner shaft 514 extends proximally through cam 524, and is slidably engaged with cam 524 so that it does not rotate with cam 524, but is reciprocatively carried with cam 524 between a proximal, or retracted, and a distal, or extended, position. Distal to cam 524, a fixed cam 526 may be connected to outer sleeve 516, and may be rigidly connected to housing 518. Fixed cam 526 may be referred to as a first cam member, and cam 524 may be referred to as a second cam member. As cam 524 rotates, cam and cam follower surfaces on cam 524 and fixed cam 526 cooperate to convert the rotary motion of the hub 520 and cam 524 to reciprocating movement of the cam 524 and inner shaft 514. At least one ball bearing 590 may be positioned between the cam and cam follower surfaces, and may reduce friction between the surfaces. A spring 528 is positioned between hub 520 and cam 524, and the spring bias of spring 528 returns the cam 524, inner shaft 514 and rasp head 508 to the distal position. It is appreciated that in other embodiments, the relative sequence of the system components may vary to accomplish the same objectives. For example, in another embodiment the relative positions of the cam 524 and fixed cam 526 may be reversed, or the location of the spring 528 may differ.

Figure 30:
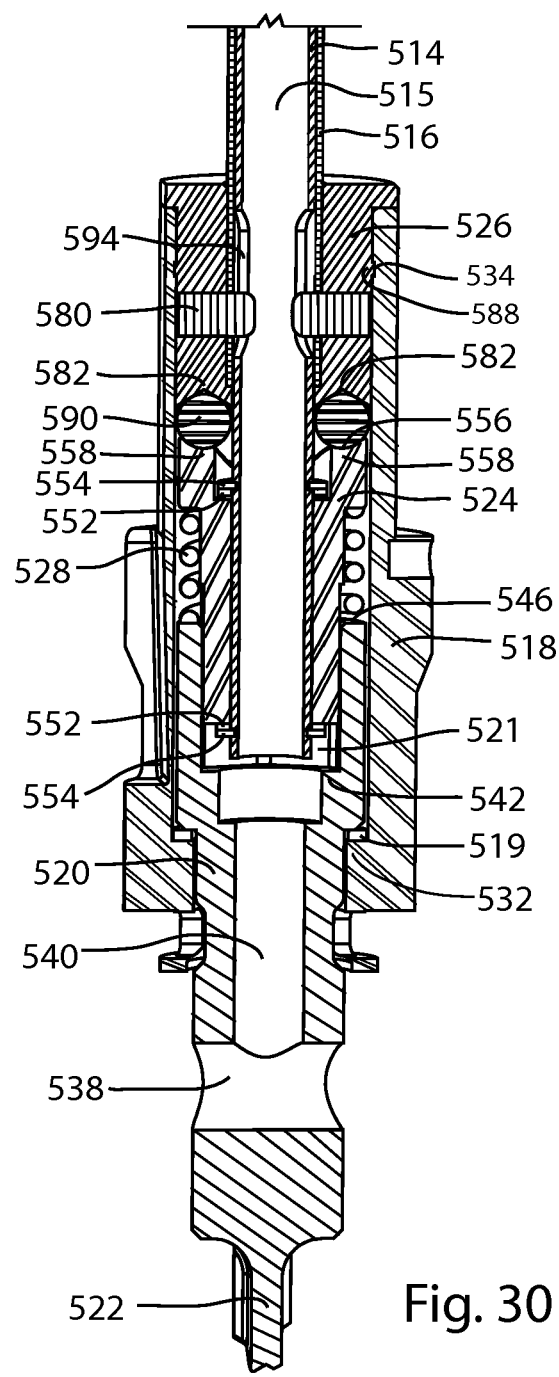
FIG. 30 is a cross-sectional view of the handle and shaft portions of the reciprocating rasping system of FIG. 27 with a tissue removal member in an retracted position.
Figure 31:
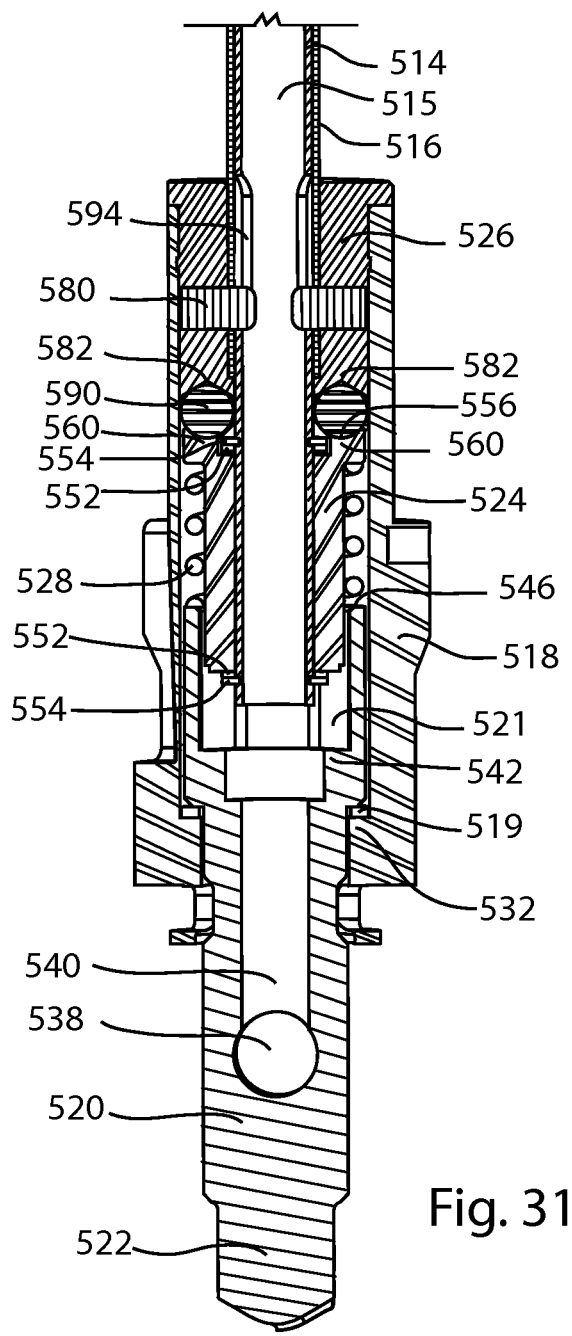
FIG. 31 is a cross-sectional view of the handle and shaft portions of the reciprocating rasping system of FIG. 27 with a tissue removal member in an extended position.

Referring to FIGS. 30 and 31, longitudinal cross-sectional views show the handle portion 506 of system 500 in the retracted and extended positions, respectively. With reference to FIGS. 29-31, system 500 is described in more detail. Housing 518 has a generally elongated tubular shape, and may include external engagement features such as slots, grooves, tabs or faces shaped for engagement with a specific powered handpiece. Housing 518 may be referred to as an adapter body. A housing bore 530 formed in housing 518 is smooth sided to allow free rotation of hub 520 and cam 524 within the bore, and free reciprocation of cam 524. A housing shoulder 532, formed as a step in bore 530, provides a seat for coupler washer 519, and retains hub 520 partially within the housing. Near the distal end of housing 518, a housing groove 534 may be formed in bore 530 for retention of fixed cam 526.

Hub 520 has a generally elongated, and partially tubular form. A transverse bore 538 is formed toward a proximal end of the hub, and a longitudinal bore 540 is formed from a distal end of the hub, extending longitudinally into a portion of the hub and opening into the transverse bore 538. The longitudinal 540 and transverse 538 bores form a segment of the suction pathway. The inside diameter of the longitudinal bore 540 is stepped, and in other embodiments may be tapered.

One step forms a first hub shoulder 542, which may provide a proximal stop for reciprocation of cam 524. Another step forms a second hub shoulder 544, which may provide a proximal stop for reciprocation of inner shaft 514. A distal portion of longitudinal bore 540 is connection feature 521, which may be a hex as previously set forth. A distal end 546 of the hub 520 provides a platform or seat for spring 528.

Cam 524 has a generally elongated tubular body 548, and is sized so that a proximal portion is received in longitudinal bore 540 of hub 520. When assembled, the cam 524 may be entirely enclosed in housing 518. A cam bore 550 extends longitudinally through the length of the cam body 548, and is sized to receive inner shaft 514. When inner shaft 514 is positioned in cam bore 550, a washer 552 and snap ring 554 are placed around inner shaft 514 at each end of cam 524, the snap rings 554 fitting into grooves formed in the inner shaft 514 to retain cam 524 in a fixed longitudinal position relative to inner shaft 514, while simultaneously allowing free rotation of cam 524 relative to shaft 514. Further detail of cam 524 is seen in FIGS. 32A-C. A portion of the outer surface of cam 524 forms connection feature 525, which is shaped to complementarily engage connection feature 521 on hub 520. Although hex shaped connection features are shown in the figures, it is appreciated that in other embodiments the connection features could comprise other complementary shapes. Toward the distal end of cam 524, cam surface 556 is formed on cam 524. Cam surface 556 is generally annular or circular and undulating, forming two protruding lobes, or high points 558 alternating with two low points 560. The high and low points are evenly distributed; the high points at 180° from each other and the low points at 180° from each other, and the low points 90° from each high point. It is appreciated that in other embodiments of the invention, the cam surface 556 could have one high and one low point; or multiple high and low points. The cam surface 556 may be recessed, forming a grooved track 557, which may be hemispherically grooved. The annular cam surface 556 may also be radially sloped such than the inner diameter of the annulus is lower than the outer diameter at any radial cross-section of the cam surface, as seen in FIG. 32B.

FIGS. 33A-C show further detail of fixed cam 526. Fixed cam 526 has a generally tubular body 568, and includes a fixed cam bore 570 which extends longitudinally through the length of the fixed cam. The bore 570 is sized to receive outer sleeve 516 in a press fit engagement. At least one slot 572 extends through body 568, and is shaped to receive a pin or screw for fixing the position of outer sleeve 516 relative to the fixed cam 526. Toward the distal end of the fixed cam 526, a rim 574 projects from the cam body 568. At the proximal end of the fixed cam 526 is formed a fixed cam surface 580. Fixed cam surface 580 is generally circular and undulating, forming two protruding lobes, or high points 582 alternating with two low points 584. The high and low points are evenly distributed; the high points at 180° from each other and the low points at 180° from each other, and the low points 90° from each high point. It is appreciated that in other embodiments of the invention, the fixed cam surface 580 could have one high and one low point; or multiple high and low points, and that the high and/or low points may be unevenly distributed. At each of the two high points 582, a recessed dimple 586 is formed. The dimples 586 are shaped to partially receive bearings 590.

With reference to FIGS. 27-31, when assembled in system 500, fixed cam 526 is at least partially enclosed by housing 518, and is displaced from hub 520. A rib 588 may be formed on the fixed cam body 568, shaped to fit into housing groove 534. Pins 580 extend through slots 572, through openings 592 in outer sleeve 516, and into elongated slots 594 in inner shaft 514. The pins and slots form a keyway system which fixes the positions of fixed cam 526 and outer sleeve 516 relative to one another, and forms a sliding connection to inner shaft 514. The elongated slots 594 allow inner shaft 514 to reciprocate relative to outer sleeve 516, constrained by pins 580.

In one method of use, handle portion 506 is fitted into a powered handpiece, with driver connection 522 engaging with a rotating driver in the handpiece. When powered on, hub 520 rotates, and cam 524 rotates with hub 520. As cam 524 rotates, cam surface 556 rotates, bearing against bearings 590 retained in dimples 586 of fixed cam 526. During rotation, when the cam high points 558 are aligned with fixed cam high points 582, inner shaft 514 and rasp head 508 are pulled proximally to a retracted position by cam 524, as seen in FIG. 30. Spring 528 is compressed between cam 524 and hub distal end 546. As rotation continues, cam low points 560 become aligned with fixed cam high points 582, and inner shaft 514 and rasp head 508 are pushed distally to an extended position by the spring bias of spring 528, as seen in FIG. 31. In this embodiment, two such retraction-extension cycles are completed with each full rotation of the hub 520. During the cycles, bearings 590 are rotated within dimples 586 as cam surface 556 spins against the bearings. The hemispherical shapes of the cam surface 556 and fixed cam surface 580, and the complementary spherical shape of bearings 590 may provide continual surface contact between the bearings and the opposing cam surfaces.

The reciprocating instrument systems disclosed herein can incorporate a variety of working ends, or cutting heads located at an end of the tissue removal member. Several examples include the rasp heads disclosed in FIGS. 3A-3D, and 11A-26C. FIGS. 34A-49B disclose additional cutting heads which include various means for rasping, cutting, severing, or otherwise modifying tissue. Any of the working ends disclosed herein may be incorporated into any of the reciprocating instrument systems disclosed herein, including systems 100 and 500, and/or a system with radiofrequency ablation capabilities such as system 400. In FIGS. 34A-49B, only the working end, or cutting head is shown, plus a portion of an outer sleeve and an inner shaft. Although referenced as outer sleeve 516 and inner shaft 514, it is understood that the outer sleeve may be outer sleeve 116 and inner shaft may be inner shaft 114 or any of the other outer sleeves, inner shafts and their equivalents disclosed herein. Correspondingly, the inner shaft of these embodiments may reciprocate along rotation axis 505 or 101, depending upon which reciprocating instrument system is used to provide the rotary to reciprocal mechanism.

Figure 34A:
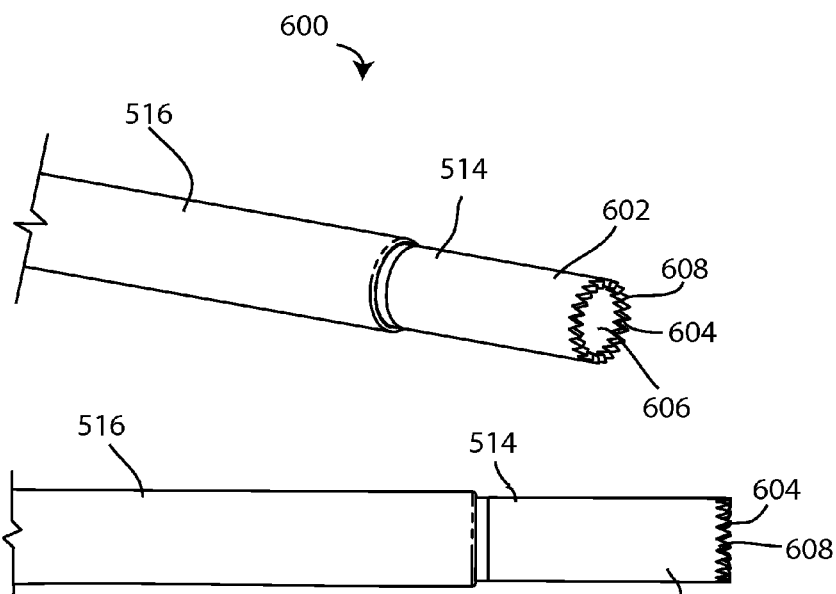
FIG. 34A is an isometric view of a distal end of a tissue removal member having a cutting head with a punch-type cutting edge.
Figure 34B:
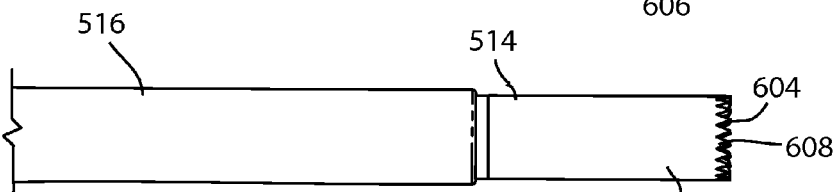
FIG. 34B is a side view of the cutting head of FIG. 34A.

FIGS. 34A-34B illustrate a working end having a distally oriented cutting feature which may be operated as a punch to sever or punch out tissue. Cutting head 600 includes a distal portion 602 of inner shaft 514. The distal end of distal portion 602 is formed into a serrated cutting edge 604. Cutting edge 604 is generally circular and forms an outer boundary of suction opening 606. Cutting edge 604 includes a series of teeth 608.

In operation of cutting head 600, inner shaft 514 reciprocates relative to outer sleeve 516, as indicated by direction arrow 610. In this and following embodiments, direction arrow 610 is shown parallel to the axis along which inner shaft 514 reciprocates. If cutting edge 604 is placed orthogonally against a portion of tissue, the reciprocating action may punch out a generally circular plug of tissue, or punch a generally circular hole into the tissue. If cutting edge 604 is placed tangentially, or at an angle to a portion of tissue, the edge may operate to gouge out a curved surface, or a groove, on the tissue. When in the first or retracted position, cutting edge 604 may be withdrawn entirely within the distal end of outer sleeve 516; alternatively, it may be positioned distal to the distal end of sleeve 516.

In other embodiments, the shape of cutting edge 604 may vary from the circular shape illustrated. In addition, the number, size, arrangement and/or shape of the teeth 608 may vary.

Figure 35A:
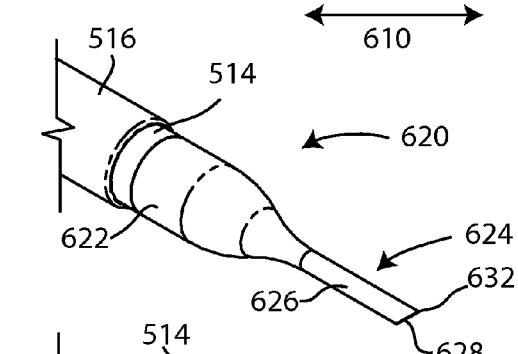
FIG. 35A is an isometric view of a distal end of a tissue removal member having a cutting head with an angled punch-type cutting edge.
Figure 35B:
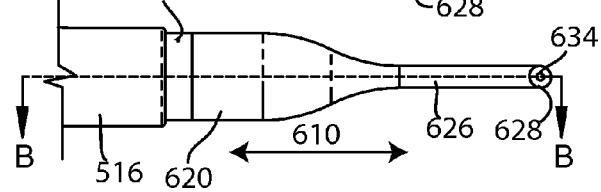
FIG. 35B is a side view of the cutting head of FIG. 35A.
Figure 35C:
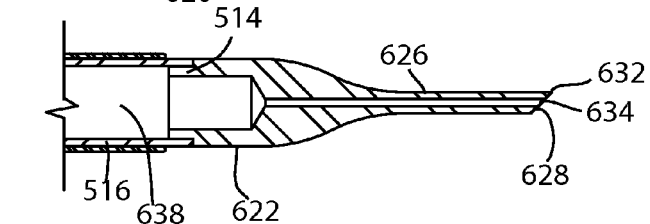
FIG. 35C is a cross-sectional view of the cutting head of FIG. 35B taken along line B-B.

FIGS. 35A-35C illustrate a working end comprising a shaft and a cutting feature, which may be used in a jack-hammer like fashion to create a tunnel in tissue. Tissue removal member 620 may comprise a proximal shaft portion 622, and an elongated rod-like cutting head 624. The proximal shaft 622 may be cannulated. Cutting head 624 may include a rod portion 626, which may also be cannulated, and an aciculated cutting edge 628. Cutting edge 628 may be tapered so that one portion of the cutting edge 628 lies farther away from the handle than another portion to form a pointed tip 632. The cutting edge 628 may include a suction opening 634. The suction opening 634 may extend proximally through the elongated rod portion 626 to connect to cannulated proximal shaft 622 and may further connect to a cannulated portion of inner shaft 514 to form a suction pathway 638.

In operation of tissue removal member 620, inner shaft 514 reciprocates relative to outer sleeve 516, as indicated by direction arrow 610. If cutting edge 628 is placed so that cutting head 624 extends orthogonally from the tissue, the reciprocating action may create a "jack-hammer" like motion to carve a tunnel like opening in the tissue. If cutting edge 628 is placed at an angle to a portion of the tissue, tissue removal member 620 may operate to shave off a desired portion of the tissue or create a groove on the tissue. Any excised tissue fragments, fluid or other materials may be drawn away from the working end through suction opening 634.

In other embodiments, one or more openings may be located slightly proximal to the tip portion to facilitate increased suction capability. The cutting head 624 may also be solid to provide greater force on impact than a hollowed tip portion. The shape and degree of the tapered cutting edge 628 may also vary. For example, the taper may be conical or irregular. The cutting edge 628 may also be blunt, and include alternative cutting features such as teeth or grating.

Figure 36A:
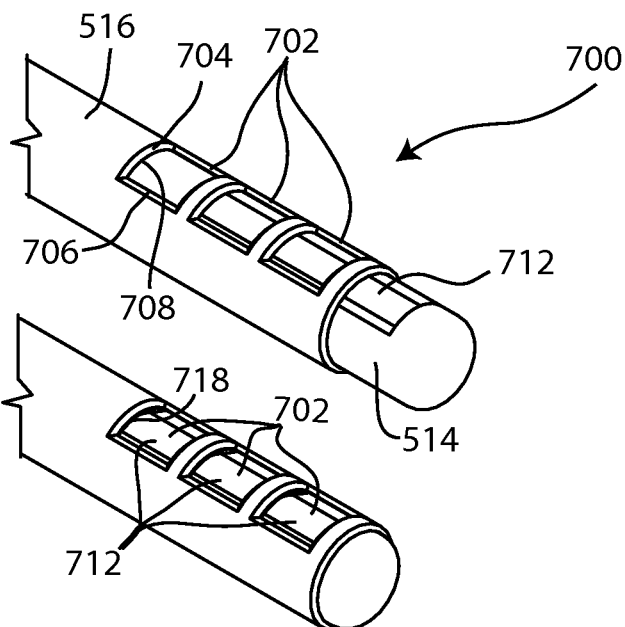
FIG. 36A is an isometric view of a distal end of a tissue removal member having a cutting head with overlapping windows, the cutting head in an extended position.
Figure 36B:
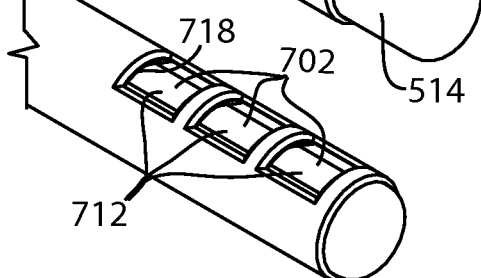
FIG. 36B is an isometric view of the cutting head of FIG. 36A, the cutting head in a retracted position.
Figure 36C:
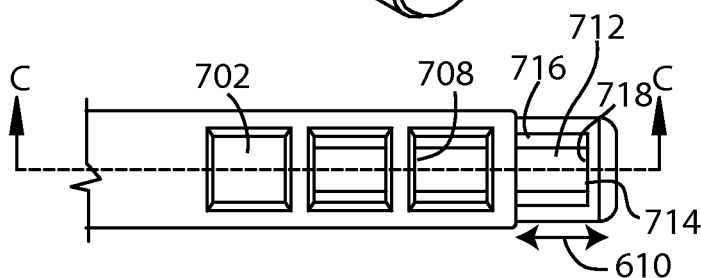
FIG. 36C is a side view of the cutting head of FIG. 36A.
Figure 36D:
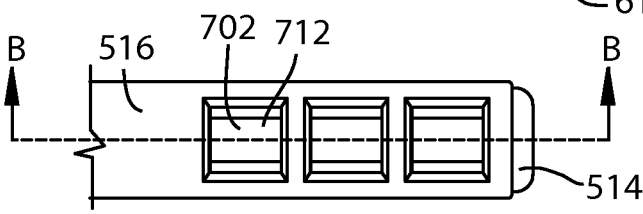
FIG. 36D is a side view of the cutting head of FIG. 36B.
Figure 36E:
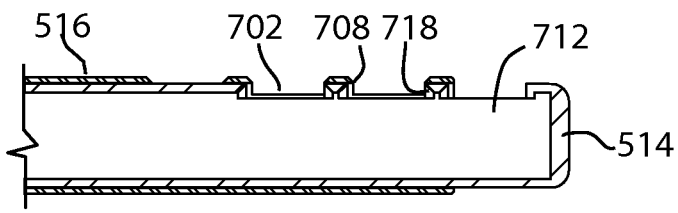
FIG. 36E is a side cross-sectional view of the cutting head of FIG. 36C taken along line C-C.
Figure 36F:
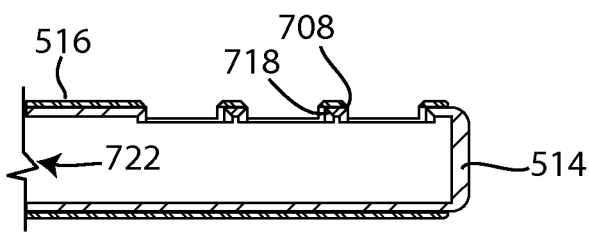
FIG. 36F is a side cross-sectional view of the cutting head of FIG. 36D taken along line B-B.

FIGS. 36A-36F illustrate a cutting head comprising one or more window-like openings having cutting features which may cooperate to sever or shave tissue. Cutting head 700 includes the distal portions of outer sleeve 516 and inner shaft 514. In the example shown, a plurality of outer windows 702 are formed toward the distal end of outer sleeve 516, each window being an opening extending through the sleeve from the outer surface to the inner surface of the sleeve. A frame 704 forms the outer boundary of each window, and each frame 704 includes at least one frame segment 706. Each frame segment 706 may be beveled to form a sharpened edge 708 along each individual frame segment. Inner shaft 514 is at least partially cannulated to form a portion of a pathway 722 for suction of excised tissue. A plurality of inner windows 712 are formed toward the distal end of inner shaft 514, and may be positioned to line up with the inner windows 702, as best seen in FIGS. 36C and 36D. Each inner window 712 is bounded by a frame 714 having at least one frame segment 716. Each frame segments 716 may be beveled and/or sharpened to form a cutting edge 718. The edges 718 may be undercut, or beveled in the opposite orientation as edges 708.

In operation, inner shaft 514 reciprocates relative to outer sleeve 516 as described previously, and as illustrated by direction arrow 610. When cutting head 700 is in the first, or retracted position as in FIGS. 36B, 36D, and 36F, each inner window 712 is substantially completely aligned with an outer window 702. Tissue may be partially suctioned through the aligned windows 712, 702, the windows forming a suction opening. When inner shaft 514 moves to the second, or extended position shown in FIGS. 36A, 36C, and 36E, edges 718 pass by edges 708, and may cooperate to sever any tissue falling between the edges 708, 718. The severed tissue may be suctioned along the suction pathway 722. Cutting of tissue may occur during both extension and retraction of inner sleeve 514.

The number, size and/or shapes of windows 702 and 712 may vary. For example, relatively larger windows may promote efficient resection of larger portions of tissue when it is desirous to modify a large quantity of tissue, while smaller windows may promote more precise resection of smaller portions of tissue, for more intricate shaping of tissue surfaces. Windows 702, 712 may be formed along one linear pathway as seen in FIGS. 36A-F, or along multiple pathways on the same instrument. Windows may be rectangular as shown, or in other embodiments may be circular, oval, triangular, or any other regular or irregular shape.

FIGS. 37A-37C depict a working end comprising a head portion with a distally oriented leading cutting edge that may sever or shave tissue fragments. Tissue removal member 740 may include a proximally located cannulated shaft portion 742, a suction opening 744 and a distally located cutting head 746. The proximal shaft 742 may include a distal portion of inner shaft 514. The cutting head 746 may include a proximal tapered top surface portion 748 and a distal top leading cutting edge 750. Leading cutting edge 750 may be tapered at a steeper angle than the surface portion 748 to provide a sharpened chisel-like point 752 at the distal edge of cutting head 740. Tissue removal member 740 may also include a flat bottom surface 754 that extends from the inner shaft 514 to the chisel-like pointed edge 752. The suction opening 744 may be located distal to the shaft portion 742 and proximal to the tapered cutting head 746, and may be generally rounded. The suction opening 744 may intersect the surface of the tapered cutting head 746 such that the opening may be continuous with the plane of the tapered surface 748. The suction opening 744 may connect to the cannulated shaft portion 742 and further to a cannulated portion of inner shaft 514 to form a suction pathway.

In operation of tissue removal member 740, inner shaft 514 reciprocates relative to outer sleeve 516, as indicated by direction arrow 610. When the leading cutting edge 750 is placed against tissue, the reciprocating motion of the edge may act to cut tissue, dissect tissue planes, and/or tease tissue away from bone. Excised tissue, fluids and other materials may be drawn away from the working area through suction opening 744.

In another embodiment, the length of the tapered portion 748, as well as the degree of taper may be varied. Additionally the width and shape of leading cutting edge 750 may vary. For example, leading cutting edge 750 may be straight in one embodiment and curved in another.

FIGS. 38A-38C illustrate a working end that includes a saw-like distal cutting head. Tissue removal member 760 comprises a proximal cannulated shaft 762, a neck portion 764 and a saw-like cutting head 766. The neck portion may include a suction opening 768 that connects to the cannulated shaft 762 and further connects to the cannulated portion of inner shaft 514 to form a suction pathway. The cutting head 766 may be relatively flat and paddle-like, and may significantly thinner than the cannulated shaft 762 and neck portion 764. Cutting head 766 may include a bladed cutting edge 770 that extends between the neck portion 764 and a tapered end portion 772. As best seen in FIG. 38C, the bladed cutting edge 768 may have a plurality of teeth 774 or serrations. The cutting head 766 may also include a flat surface 776 opposite the bladed surface 768, extending between the neck portion 764 and the tapered end portion 772.

In operation of tissue removal member 760, inner shaft 514 reciprocates relative to outer sleeve 516, as indicated by direction arrow 610, such that the bladed cutting edge 768 provides a sawing action to separate tissue from bone or to bisect tissue material. The excised tissue, fluid and other materials may be removed from the working area through the suction opening 768 in the neck portion 764.

In another embodiment, the cutting edge 768 of tissue removal member 760 may contain no teeth-like extensions, and may instead comprise a smooth surface and act as a reciprocating scalpel during use. Alternatively, the number, size and positioning of teeth on the cutting edge may vary; for example teeth 774 may be provided along a single row as seen in FIG. 38B, or in multiple rows. Teeth 774 may be unidirectionally oriented, such that cutting occurs only as the blade moves proximally toward the sleeve or only as the blade moves distally from the sleeve. Alternatively, teeth 774 may be bi- or multi-directionally oriented, providing cutting action as the blade moves both proximally and distally between the retracted and extended positions. Also, teeth may occur on alternative surfaces of cutting head 760. For example, the tapered end 772 and/or the flat surface 776 may contain plurality of cutting features including teeth, blades, fins, knurling, or roughening that extend outward from the cutting head 766 to provide additional sawing capability during use.

Figure 39A:
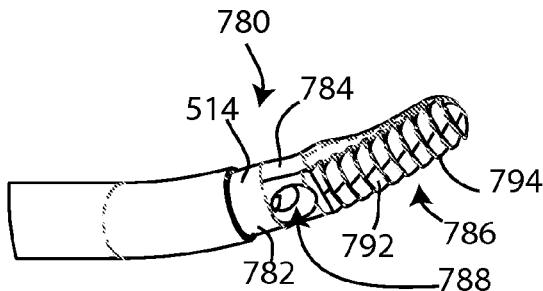
FIG. 39A is an isometric view of a distal end of a tissue removal member having a curved cutting head.
Figure 39B:
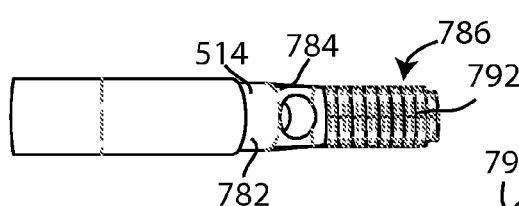
FIG. 39B is a top view of the cutting head of FIG. 39A.
Figure 39C:
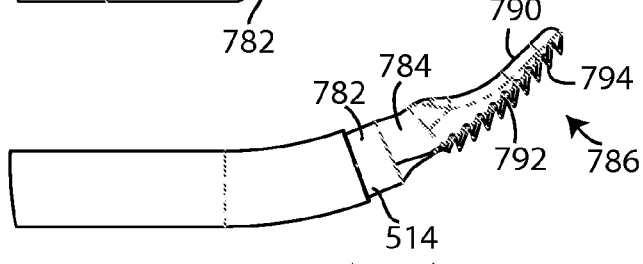
FIG. 39C is a side view of the cutting head of FIG. 39A.

FIGS. 39A-39C illustrate a working end with a curved cutting end that allows the instrument to produce a radiused end motion to sever or slice tissue in an irregularly shaped surgical environment. For example, the radiused rasping surface may be advantageous during a notchplasty procedure or during treatment of the trochlear groove. Tissue removal member 780 comprises a curved proximal cannulated shaft 782, a middle portion 784 and a curved distal cutting head 786. The proximal cannulated shaft 782 includes the distal portion of inner shaft 514 and may be flexible to allow the tissue removal member 780 to bend. The middle portion 784 of tissue removal member 780 includes a suction opening 788, which connects to the cannulated shaft 782 and further connects to the cannulated portion of the inner shaft 514 to form a suction pathway. The middle portion 784 may also be flexible to allow for further bending. The distal cutting head 786 may have a curved shape and include a smooth top surface 790 and a cutting edge 792 opposite the top surface. As shown in FIGS. 39A-39C, the cutting edge may comprise a plurality of teeth 794 or other cutting features including points, threading, ridges, blades, grooves, surface roughening, grit or filing features that extend outward from the cutting head 786.

In operation of tissue removal member 780, inner shaft 514 reciprocates relative to outer sleeve 516 as indicated by direction arrow 610. The tissue removal member 780 may be inserted into a joint or other cavity in a surgical environment, particularly a space for which linear access is problematic or impossible. The cutting edge 792 may be placed so that it contacts a portion of the cavity. The flexibility of the cannulated shaft 782 and middle portion 784, as well as the curvature of the cutting head 786 may allow the instrument to conform to the shape of the cavity. The reciprocating action of the tissue removal member 780 may serve to shave or slice material to help shape the cavity.

In an alternative embodiment, the curvature or angulation of cutting edge 792 and/or the angle of teeth 794 can vary to provide differently angled cutting surfaces. For example, the teeth 794 may be unidirectionally oriented, such that the cutting occurs only as the blade moves distally from the sleeve 516 or only as the blade moves proximally into the sleeve 516. Alternatively, teeth 794 may be bi- or multi-directionally oriented, providing cutting action as the blade moves both proximally and distally. The teeth 794 may also be distributed on one or more sides of cutting head 786. In addition, the inner shaft 514 and cannulated shaft 782, as well as the middle portion 784 may be fixed in a curved position, rather than flexible. Alternatively, the inner shaft 514, cannulated shaft 782 and middle portion 784 may be fixed in a straight position, while the cutting head 786 may have a fixed or flexible curved orientation.

Figure 40A:
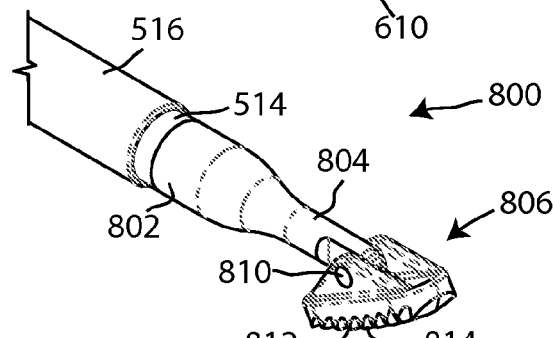
FIG. 40A is an isometric view of a distal end of a tissue removal member having a hinged cutting head.
Figure 40B:
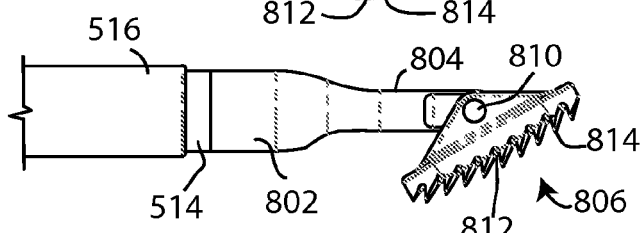
FIG. 40B is a side view of the cutting head of FIG. 40A.
Figure 40C:
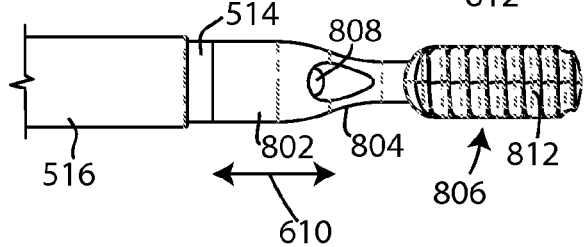
FIG. 40C is a top view of the cutting head of FIG. 40A.

FIGS. 40A-40C illustrate a working end comprising a hinged cutting end that may sever or shave tissue that may be disposed on an uneven surface. Tissue removal member 800 comprises a cannulated proximal shaft 802, a neck portion 804 and a hinged distal cutting head 806. The proximal cannulated shaft 802 includes the distal portion of inner shaft 514 and extends distally to the neck portion 804. Neck portion 804 may extend between the cannulated shaft 802 and the hinged cutting head 806, and may include a suction opening 808 to remove any severed tissue or fluid from the working area. The cutting head 806 may be attached to the distal portion of the neck 804 by a hinge feature 810 such as a rod, screw, shaft or axle so that it is rotatably attached. The hinge feature may extends through an aperture in the neck portion so that the hinge feature 810 may be unconstrained, allowing cutting head 806 to freely pivot relative to the shaft around at least one axis. The hinge feature 810 may also include a spring mechanism to bias the head 806 to a default position in the head's range of motion. Cutting head 806 may include a cutting edge 812 comprising a plurality of teeth 814 or other cutting features such as fins, prongs or blades.

Like previous embodiments, in operation of tissue removal member 800, inner shaft 514 reciprocates relative to outer sleeve 516 as illustrated by direction arrow 610. The cutting edge 812 may be placed against a portion of tissue and the reciprocating motion may act to sever or slice tissue along an uneven surface, allowing cutting head 806 to undulate with the contours of the tissue surface. The severed tissue, fluid or other material fragments may be removed from the working area through the suction opening 808.

Free rotation of cutting head 806 may be advantageous for use on contoured surfaces, as the pivoting of the cutting head 806 may allow the cutting edge 812 to move freely along the uneven surfaces. Alternatively, the hinge feature 810 may further include a locking mechanism so that cutting head 806 may be lockably adjusted during use to a desired angle. Also, cutting edge 812 may be generally flat as depicted in FIGS. 40A-40C, however, the cutting edge 812 may also be curved or rounded.

Figure 41A:
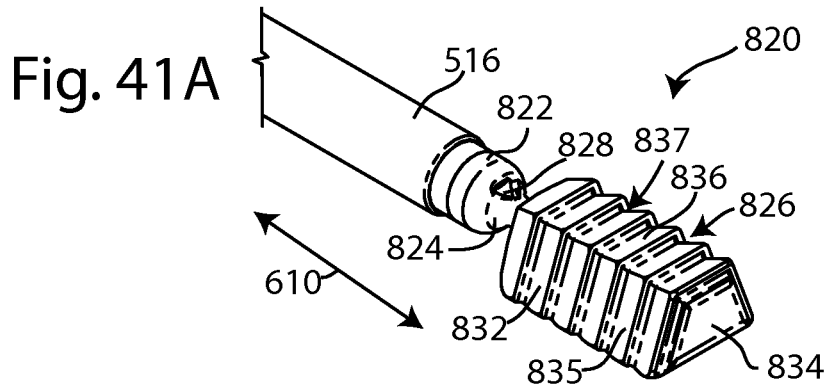
FIG. 41A is an isometric view of a distal end of a tissue removal member having a trapezoidal cutting head.
Figure 41B:
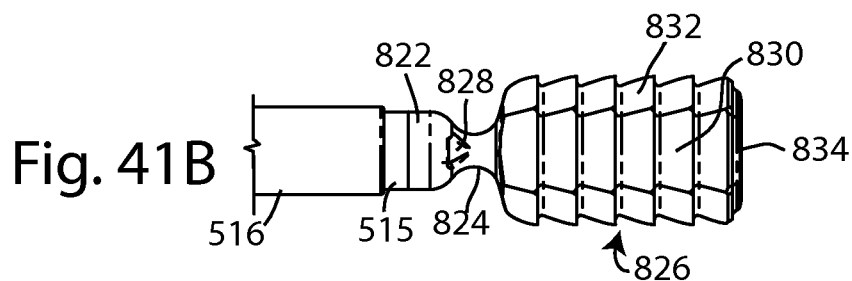
FIG. 41B is a top view of the cutting head of FIG. 41A.
Figure 41C:
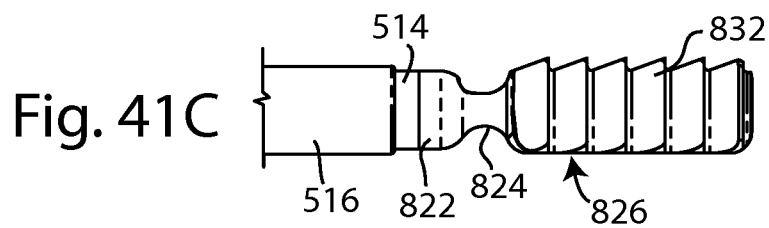
FIG. 41C is a side view of the cutting head of FIG. 41A.

FIGS. 41A-41C illustrate a working end comprising a distally oriented three-dimensional cutting feature, which may be operated as a punch, rasp, or broach to sever tissue or to create a tunnel-like opening in tissue. Tissue removal member 820 includes a proximal cannulated shaft 822, a neck portion 824 and a distally oriented trapezoidal shaped cutting head 826. Cannulated shaft 822 includes a distal portion of inner shaft 514 and extends distally to connect to neck portion 824, which is narrower than shaft 822. Neck portion 824 may include a suction opening 828 that may serve to extract tissue material from the working area. As seen best in FIG. 41A, cutting head 826 is located distal to the neck portion 824. Cutting head 826 is substantially trapezoidal, although cutting head 826 may alternatively be a variety of polygonal shapes such as triangular, square or rectangular. Cutting head 826 may also be irregularly shaped. Cutting head 826 may include at least one cutting edge that may contain a plurality of cutting features 832 such as teeth, blades, ridges, sharp edges or grooves. In the example shown in FIGS. 41A-41C, cutting head 826 includes teeth 832, disposed in rows, on three cutting edges 835, 836, 837. The number of teeth may vary, and the teeth may be distributed and oriented in a variety of positions. Cutting head 826 may also include a flat distal surface 834.

In operation, the trapezoidal shape of tissue removal member 820 is substantially three-dimensional, and may be advantageous for preparing surfaces in resectioning procedures, particularly during subacromial decompression and resection of the distal clavicle, as well as during ACL joint resection. During use, the cutting head 822 may be positioned orthogonal to the tissue surface such that when the inner shaft 514 reciprocates relative to outer sleeve 516, cutting head 822 may puncture the tissue to form a tunnel-like structure.

In another embodiment, the plurality of teeth 832 may be included on all or fewer sides of the trapezoidal cutting head 826. Alternatively, the sides of the cutting head 826 may be smooth and contain no teeth, to be used to puncture or indent bone or other material. The cutting head 826 may also be tapered, and in some embodiments, may comprise a leading cutting edge.

Figure 42A:
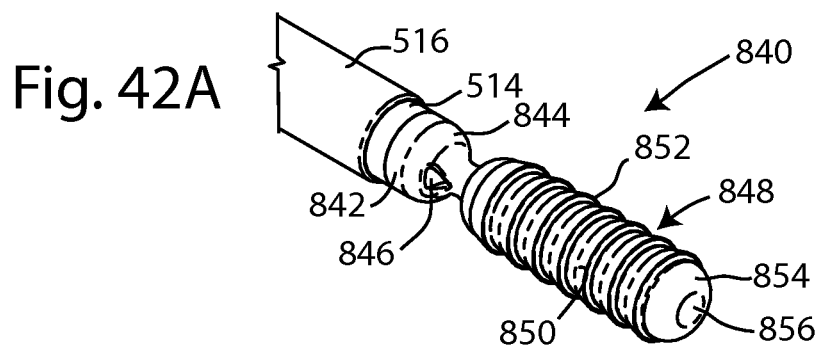
FIG. 42A is an isometric view of a distal end of a tissue removal member having a cylindrical cutting head.
Figure 42B:
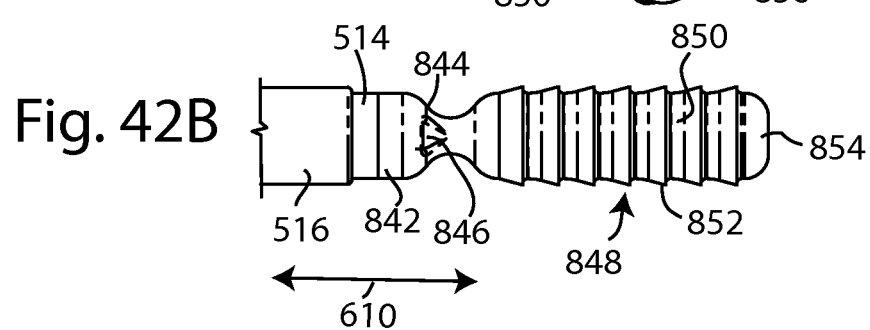
FIG. 42B is a top view of the cutting head of FIG. 42A.

FIGS. 42A and 42B illustrate a working end comprising a distally oriented cylindrical cutting head that may be used to create a hollowed bore-like structure in tissue material. Tissue removal member 840 may include a proximally located cannulated shaft portion 842, a neck portion 844 and a distally located cylindrical cutting head 848. The proximal shaft portion 842 may contain a distal portion of inner shaft 514, and may extend from the distal portion of inner shaft 514 to the neck portion 844. The neck portion 844 may contain a suction opening 846, and extends between the proximal shaft portion 842 and the distal cylindrical cutting head 848. The neck portion 844 may be thinner than the shaft portion 842 and thinner than the cutting head 848. The cutting head 848 may be an elongated barrel shape, and contains an annular working surface 850 that contains a plurality of cutting features 852. The cutting features 852 may be contained in rows that extend circumferentially around the cutting head 848, and may be comprised of teeth, points, threading, ridges, sharp edges, grooves, knurling, surface roughening, grit or other cutting features. The distal surface 854 of cutting head 848 may be smooth and contain a depression 856.

In operation of tissue removal member 840, inner shaft 514 reciprocates relative to outer sleeve 516, as indicated by direction arrow 610. If tissue removal member 840 is placed against the tissue such that cylindrical cutting head 848 extends orthogonally from the tissue, the reciprocating action may act to create a hollowed, tunnel-like structure in the tissue or to widen notches in tissue material. The suction opening 846 may be used to remove tissue material and fluid from the working area. Specifically, the cylindrical rasping surface may be advantageous for widening an anterior portion and to recess the roof of the intercondylar notch during a notchplasty procedure.

In another embodiment of tissue removal member 840, the annular working surface 850 may contain differing number, size and positioning of cutting features 852. For example, teeth 852 may be provided along a single row, or in multiple rows. Teeth 852 may be unidirectionally oriented, as best seen in FIG. 26B, such that cutting occurs only as the blade moves distally away from the sleeve or as the blade moves proximally toward the sleeve. Alternatively, teeth 852 may be bi- or multi-directionally oriented, providing cutting action as the blade moves both proximally and distally between the retracted and extended positions. The annular working surface 850 may contain no cutting features and instead comprise a smooth surface. Alternatively, cutting head 848 may also contain additional cutting features or a leading cutting edge on the distal surface 854.

Figure 43A:
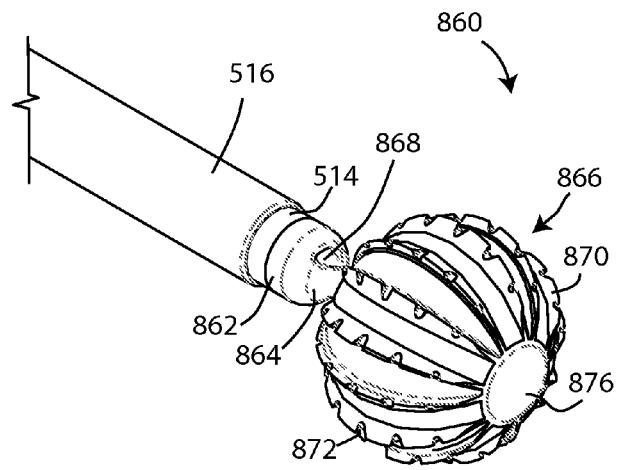
FIG. 43A is an isometric view of a distal end of a tissue removal member having a spherical cutting head.
Figure 43B:
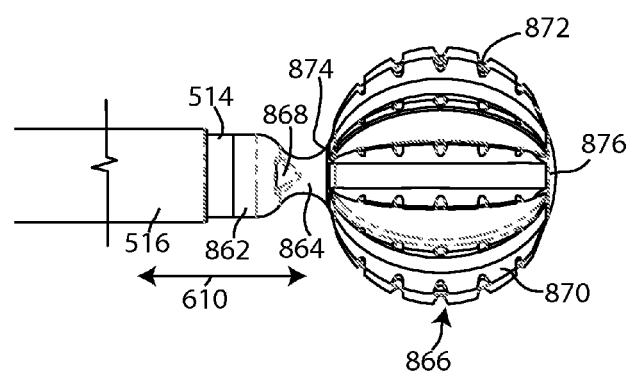
FIG. 43B is a top view of the cutting head of FIG. 43A.

FIGS. 43A and 43B illustrate an embodiment of a working end comprising a bulbous cutting head that may be used to punch out or shave a portion of tissue. Tissue removal member 860 includes a proximal shaft portion 862, a neck portion 864 and a spherical cutting head 866. The proximal shaft portion 862 may be cannulated and may include a distal portion of the inner shaft 514. The neck portion 864 extends between the proximal shaft 862 and a base 874 of spherical cutting head 866. The neck 864 may be thinner than the shaft 862 and the cutting head 866 in at least one plane and may include a suction opening 868 that is connected to the cannulated portion of the shaft 862, which further connects to the cannulated portion of the inner shaft 514 to form a suction pathway. The spherical cutting head 866 may include a plurality of cutting features 870 such as teeth, points, knurling, surface roughening or other cutting features. As shown in FIGS. 43A and 43B, the cutting features 870 may be blades that contain cutting grooves 872, and may be disposed in rows that extend distally from the base 874 of cutting head 866, where the cutting head 866 connects to the neck portion 864. Cutting head 864 may also include a distal surface 876 that may be smooth and relatively flat.

In operation of tissue removal member 860, inner shaft 514 reciprocates relative to outer sleeve 516, as indicated by direction arrow 610 such that the bladed cutting head 866 can sever tissue along a contoured surface or can puncture tissue along a flat tissue surface. The excised tissue, fluid and other materials may be removed from the working area through the suction opening 868 in the neck portion 864 and passed through the suction pathway.

In an alternative embodiment of tissue removal member 860, the size of cutting head 866 may vary relative to the diameter of the neck portion 864. The plurality of cutting features 870 may be unilaterally distributed on the cutting head 866, or they may be bi- or multilaterally distributed.

Figure 44A:
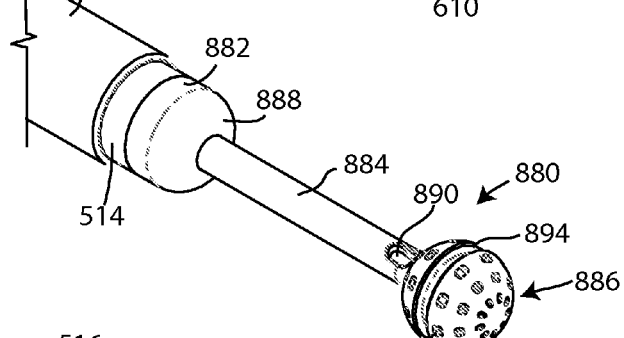
FIG. 44A is an isometric view of a distal end of a tissue removal member having a spherical cutting head.
Figure 44B:
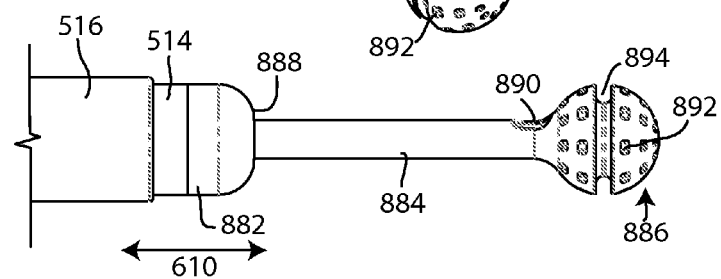
FIG. 44B is a top view of the cutting head of FIG. 44A.
Figure 45A:
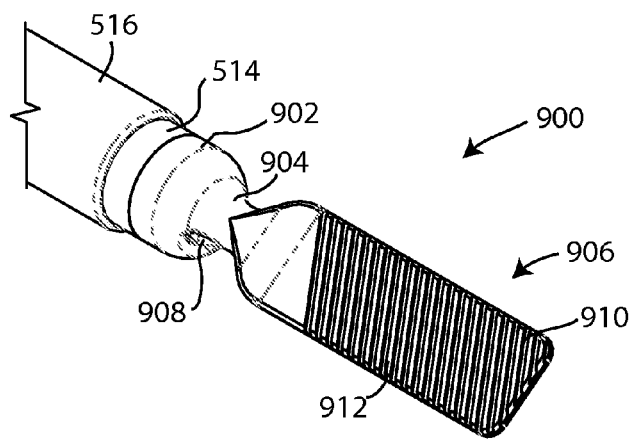
FIG. 45A is an isometric view of a distal end of a tissue removal member having a file-type cutting head.
Figure 45B:
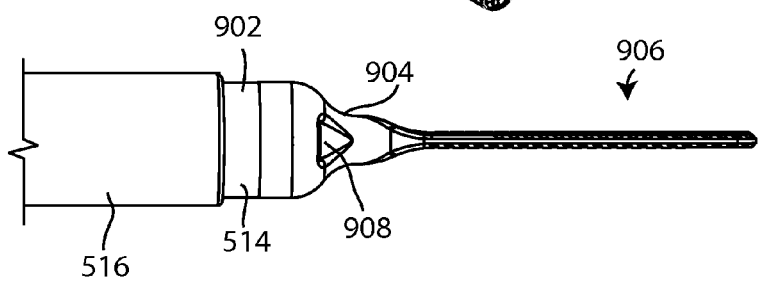
FIG. 45B is a top view of the cutting head of FIG. 45A.
Figure 45C:
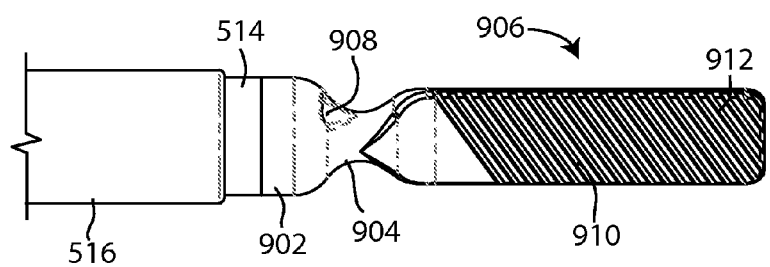
FIG. 45C is a side view of the cutting head of FIG. 45A.
Figure 45D:
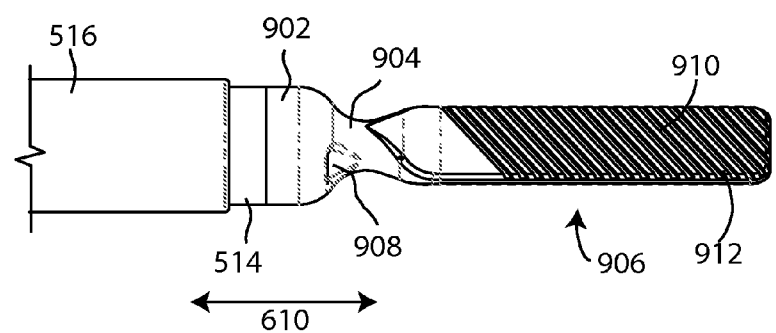
FIG. 45D is an angled side view of the cutting head of FIG. 45A.

FIGS. 44A through 44B illustrate a working end that includes a spherical cutting end that can be used as a drill or boring tool, or used to smooth an already created bore. Tissue removal member 880 includes a proximal cannulated shaft portion 882, a medial elongated rod portion or neck 884, and a distal spherical cutting head 886. The proximal cannulated shaft 882 may include a distal portion of inner shaft 514 and may have a rounded shoulder 888 that connects to the medial elongated rod 884. The elongated rod 884 may also be cannulated and may contain a distal suction opening 890. The distal spherical cutting head 886 includes a plurality of cutting features 892, which may comprise teeth, blades, knurling, or fins. The cutting features 892 may be distributed in ordered patterns, or may be randomly distributed along the spherical surface of cutting head 886. The spherical cutting head 886 may also comprise a central circumferential groove 894.

In operation of tissue removal member 880, like previous embodiments, inner shaft 514 reciprocates relative to outer sleeve 516, as indicated by direction arrow 610. The spherical cutting head 886 may be placed against tissue such that the tool acts to shave tissue or smooth a contoured tissue surface.

In an alternative embodiment, tissue removal member 880 may not include a central groove, but may instead be entirely spherical. The plurality of cutting features 892 may also comprise small, window-like openings having an edge that may be beveled to form a cutting edge, so that in operation, the surface of cutting head 886 would shave tissue like a cheese-grater. The cutting 892 features may be arrayed in regular rows, as shown best FIG. 44B, or they may be distributed randomly across the curved surface of cutting head 886.

FIGS. 45A-45D illustrate a working end comprising a flat, file-like cutting head that may be advantageous for preparing a flat tissue surface, for example, during shoulder procedures. Tissue removal member 900 comprises a proximal shaft portion 902, a neck portion 904 and a distal cutting head 906. Shaft portion 902 may be cannulated and may include a distal portion of inner shaft 514. Neck portion 904 may extend between the shaft portion 902 and the distal cutting head 906. Neck portion 904 may be thinner than shaft portion 902, and may be tapered such that the portion closest to the shaft 902 is broader than the distal portion in at least one plane. Neck portion 904 may contain a suction opening 908. Suction opening 908 may connect to the cannulated portion of shaft 902, which may further connect to the cannulated portion of inner shaft 514 to form a suction pathway. The distal portion of neck 904 may be thinner than the proximal portion in at least one plane, and may connect to cutting head 906. Cutting head 906 may be significantly thinner than neck portion 904, and may contain at least one cutting edge 910, which may comprise a plurality of filing features 912. Filing features 912 may include teeth, points, threading, ridges, sharp edges, grooves, knurling, surface roughening, grit or other filing features. The filing features 912 may be arrayed in regular rows, as shown best in FIGS. 45A and 45C.

In operation of tissue removal member 900, inner shaft 514 reciprocates relative to outer sleeve 516, as indicated by direction arrow 610. Cutting head 906 can be placed against tissue such that the reciprocating motion of the cutting edge 912 of tissue removal member 900 acts to file or tease tissue material away from a bone or joint cavity. Filing features 912 may be oriented such that as the tissue is teased away from the bone, it is encouraged towards the suction opening 908. Excised tissue, fluid and other materials may be removed from the working area through suction opening 908 and passed through the suction pathway.

In an alternative embodiment, filing features 912 may be arrayed in overlapping or intersecting patterns, or may be distributed randomly or evenly across the surface of cutting edge 910. Filing features 912 may be located on one or both sides of cutting head 906. The filing features 910 may be oriented differently on each side of the cutting head 906. Alternatively, cutting head 906 may contain no filing features and instead comprise two smooth surfaces. Cutting head 906 may also have a degree of curvature to file tissue along contoured edges.

FIGS. 46A and 46B illustrate a working end comprising a distal toothed and tapered cutting edge that may be used in procedures to separate or tease tissue away from bone. Tissue removal member 920 includes a proximal shaft portion 922, a neck portion 924 and a cutting head 926. Shaft portion 922 may include a distal portion of inner shaft 514 and may be cannulated. Neck portion 924 may extend between the proximal shaft portion 922 and distal cutting head 926, and may include a suction opening 928. Suction opening 928 may connect to the cannulated portion of shaft 922, and may further connect to the cannulated portion of inner shaft 514 to form a suction passageway. Distal cutting head 926 may comprise a 3-dimensional elongated block like structure including a plurality of smooth surfaces 930 and a distal cutting edge 932 that is tapered and contains a plurality of cutting features 934 such as teeth, ridges, blades, grooves, roughening or other features. In the example shown in FIGS. 46A-46C, the cutting features 934 are rows of teeth that extend laterally across the cutting edge 932.

In operation of tissue removal member 920, inner shaft 514 reciprocates relative to outer sleeve 516, as indicated by direction arrow 610. Cutting head 926 may be placed against tissue such that the toothed, tapered distal cutting edge 932 acts similar to a chisel-feature to sever tissue. The cutting features 934 may be oriented on the cutting edge 932 such that they may pull tissue away from bone or other anchor material towards the suction opening 928. The excised material may be removed via the suction opening 928 from the working area.

In an alternative embodiment, the length and degree of taper of the tapered cutting edge 932 may vary, as may the size and direction of the teeth 934 or other cutting features. The orientation of the cutting features 934 may also vary, and extend vertically to create a saw-like motion. Cutting features 934 may also be located on additional surfaces of cutting head 926. Alternatively, no surfaces of cutting head 926 may include any cutting features to create a blunt distal tapered surface for recessing or reshaping tissue.

FIGS. 47A and 47B depict a working end comprising a rectangular cutting head having cutting teeth on two opposite sides to cut grooves, slots or rectangular-shaped openings into tissues. Tissue removal member 940 includes a proximal shaft portion 942, a neck portion 944 and a rectangular distal cutting head 946. Proximal shaft portion may include a distal portion of inner shaft 514. The neck portion 944 may be thinner than the shaft portion 942 and distal cutting head 946. Neck portion 944 may extend between the proximal shaft portion 942 and the distal cutting head 946, and may include at least one suction opening 948. Distal cutting head 946 may include at least one cutting edge. In the example shown in FIGS. 47A and 47B, cutting head 946 includes two cutting edges 950, 952, located on opposing sides of cutting head 946. Cutting edges 950 and 952 include a plurality of teeth-like cutting features 953 that extend outward from the cutting edge. Cutting features 953 may be positioned such that they pull tissue proximally toward the suction opening 948 during operation. Cutting head 946 also includes a smooth top surface 954, a smooth bottom surface 956 and a blunt distal face 958.

In operation of tissue removal member 940, inner shaft 514 reciprocates relative to outer sleeve 516, as indicated by direction arrow 610. Cutting head 946 may be positioned against tissue to carve or tease tissue away from bone, or to create a groove or rectangular-shaped opening in tissue. The excised tissue may be removed through suction opening 948.

In an alternative embodiment, fewer or more surfaces of cutting head 946 may contain a plurality of cutting-features 953, including teeth, blades, barbs, fins, knurling, roughing or grooves. The cutting features 953 may alternatively be positioned randomly or in intersecting patterns, and may be bi- or multi-directionally oriented such that tissue is severed as the cutting head 946 reciprocates both proximally and distally. The length and width of cutting head 946 may also vary.

Figure 48A:
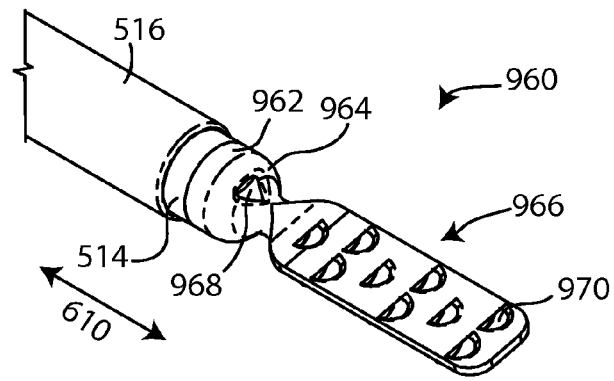
FIG. 48A is an isometric view of a distal end of a tissue removal member having a grating cutting head.
Figure 48B:
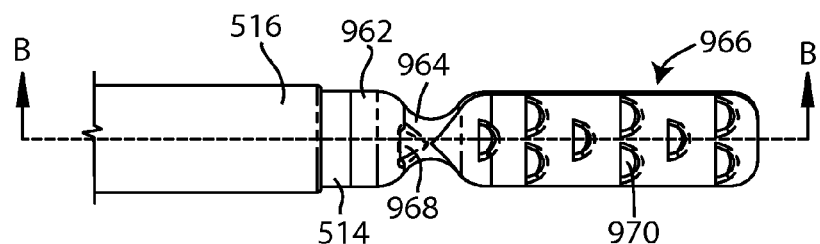
FIG. 48B is a top view of the cutting head of FIG. 48A.
Figure 48C:
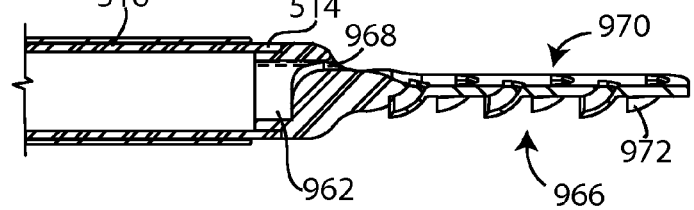
FIG. 48C is a side cross-sectional view of the cutting head of FIG. 48B, taken along line B-B.

FIGS. 48A-48C illustrate a working end comprising a cutting head that includes a grating cutting surface that may act to scrape or tease tissue away from bone, and may also be advantageous for preparing flat tissue surfaces. Tissue removal member 960 includes a proximal shaft portion 962, a medial neck portion 964 and a distal cutting head 966. Shaft portion 962 may include a distal portion of inner shaft 514, and may be cannulated. Neck portion 964 may be thinner than both the shaft portion 962 and the cutting head 966, and may extend between the two. Neck portion 964 may also include a suction opening 968, which may connect to the cannulated portion of shaft 962, which further connects to the cannulated portion of inner shaft 514 to create a suction pathway. Distal cutting head 966 may be flat and paddle-like, and comprise a plurality of apertures 970. In FIG. 48B, it can be seen that the apertures may be distributed symmetrically about a center axis B that extends the length of the cutting head 966. The apertures may contain cutting edges 972 such as curved blades like those found on a cheese-grater that may protrude beyond one or both surfaces at an acute angle to the plane of the cutting head 966 such that any excised tissue material is encouraged towards the suction opening 968.

In operation of tissue removal member 960, inner shaft 514 reciprocates relative to outer sleeve 516, as indicated by direction arrow 610. Cutting head 966 may be placed against a flat tissue surface such that when tissue removal member 960 reciprocates, tissue material may be shaved by the cutting edges 972 and passed through the apertures 970 towards suction opening 968.

In an alternative embodiment, neck portion 964 may contain additional suction openings 968 to pull excised tissue away from the surfaces of cutting head 966. The apertures 970 may be distributed in an alternative patterned, ordered fashion, or they may be randomly distributed along the face of cutting head 966. The cutting blades may extend at a uniform angle from the surface of cutting head 966, or may extend in a bi- or multi-angular fashion from the surface of cutting head 966 so that tissue may be sliced as tissue removal member 960 moves both proximally and distally. The length and width of cutting head 966 may also vary.

Figure 49A:
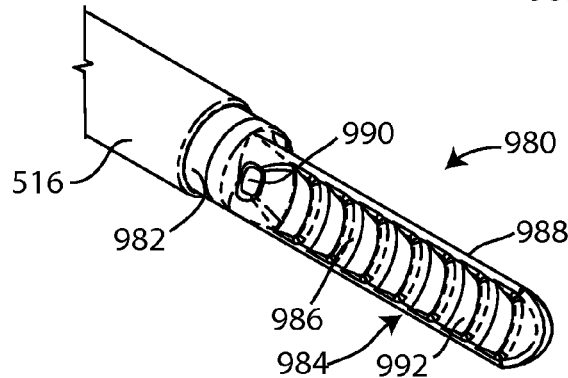
FIG. 49A is an isometric view of a distal end of a tissue removal member having a concave cutting head.
Figure 49B:
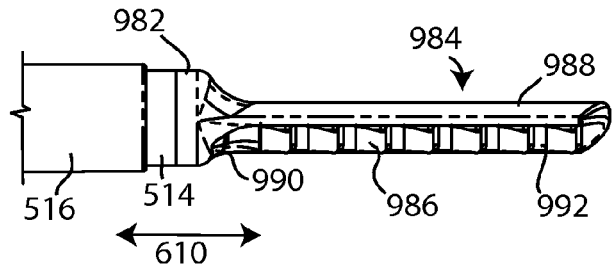
FIG. 49B is a side view of the cutting head of FIG. 49A.

FIGS. 49A and 49B illustrate a working end comprising a cutting head having a concave working surface which may be advantageous during a notchplasty procedure and for treatment of the trochlear groove. Tissue removal member 980 includes a proximal shaft portion 982 and a cutting head 984. Shaft portion 982 may include a distal portion of inner shaft 514 and may contain a cannulated portion. Cutting head 984 may include a concave cutting edge 986 and a smooth outer surface 988. Cutting head 984 may also include a suction opening 990 located proximal to the concave cutting edge 986. The suction opening 990 may be connected to the cannulated portion of shaft portion 982, which may further be connected to the cannulated portion of inner shaft 514 to create a suction pathway. Cutting edge 986 may comprise a plurality of cutting features 992 that are distributed in rows along the cutting edge 986. Cutting features 992 may include teeth, blades, barbs, fins, knurling, grooves or roughening to grasp and/or sever tissue along the curved cutting edge 986. The cutting features 992 may be oriented such that as tissue is excised, it is encouraged towards the suction opening 990.

In operation of tissue removal member 980, inner shaft 514 reciprocates relative to outer sleeve 516, as indicated by direction arrow 610. The radius of cutting head 984 may be selected to match the radius of a desired tissue surface. The reciprocating motion of cutting head 984 along a curved tissue surface may act to sever tissue material and pull the tissue proximally towards suction opening 990.

In an alternative embodiment, the smooth outer surface 988 may also contain a plurality of cutting features. The degree of curvature and length of cutting head 984 may vary. The cutting features 992 may be oriented at different angles and may be distributed differently on the cutting edge 986.

Figure 50:
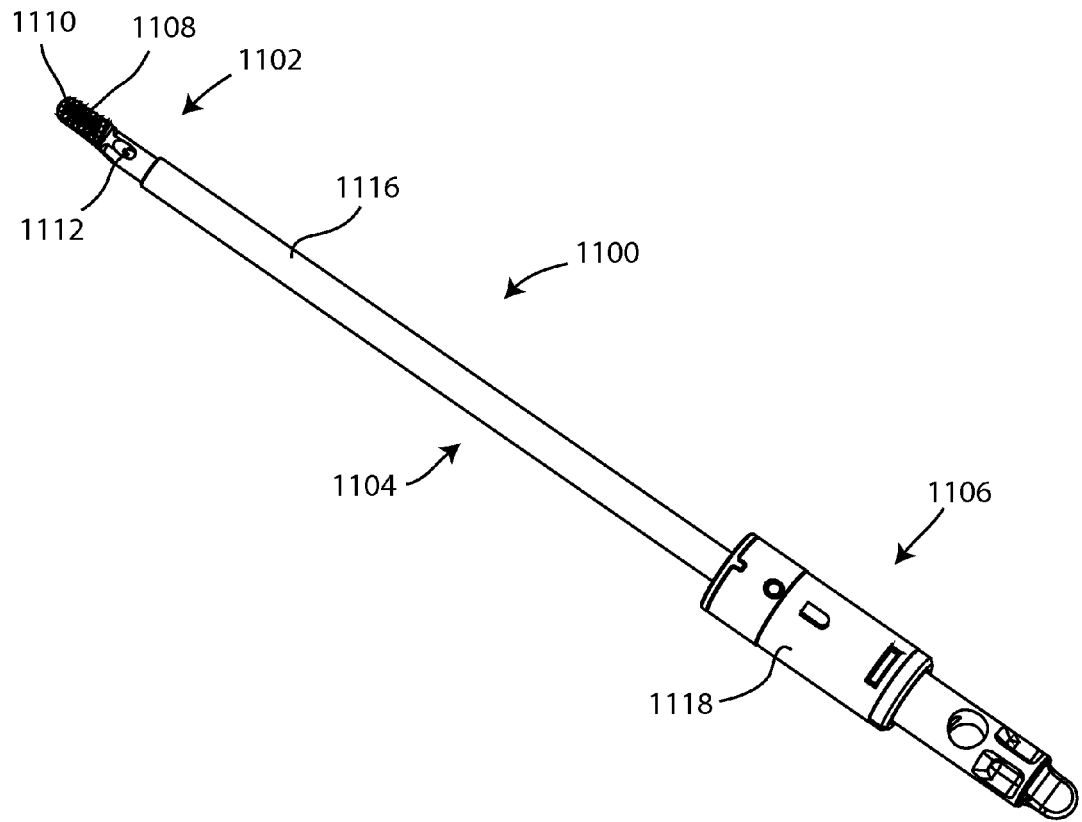
FIG. 50 is an isometric view of a reciprocating surgical instrument.

Referring to FIG. 50, a reciprocating surgical instrument 1100 according to one example of the present disclosure is shown in an isometric view. Reciprocating surgical instrument 1100 comprises working member or head portion 1102, shaft portion 1104, and handle portion 1106. Head portion 1102 comprises a working member or head 1108. In this example, the head 1108 is a rasp, which includes a plurality of teeth 1110 or cutting edges which may cut anatomical tissues when drawn along the tissue surface. The teeth may be particularly suited for cutting or removing hard tissues such as bone or cartilage. A suction opening 1112 can be located on the head portion 1102, disposed between the teeth and the shaft portion. The shaft portion 1104 may comprise a translation member, such as an inner shaft 1114 (FIG. 52), which extends proximally from the rasp head 1108 and is received in the handle portion 1106. The inner shaft 1114 may extend through an optional outer sleeve 1116 which can be joined to the handle portion 1106. Inner shaft 1114 can be hollow, having a bore 1115 (not visible in FIG. 50, but seen in FIGS. 53 and 54) extending from suction opening 1112 to a proximal end of the inner shaft 1114, the bore 1115 forming a portion of a suction pathway. Handle portion 1106 can include an outer housing 1118 which at least partially encloses a rotatable cam 1124, a fixed cam 1126 (FIG. 52), and a rotatable or rotary hub 1120 translationally coupled to the rotatable cam 1124. When the handle portion 1106 is engaged in a powered rotary hand piece (not shown) and power is supplied, hub 1120 will rotate causing the rotatable cam 1124 to rotate. The rotatable cam 1124 and fixed cam 1126 provide a motion conversion mechanism which converts the rotary motion of the hub 1120 to an axial reciprocal motion causing the inner shaft 1114 and attached head 1108 to translationally reciprocate back and forth in the proximal and distal directions. Hub 1120 may also be referred to as a sluff chamber.

Figure 51A:
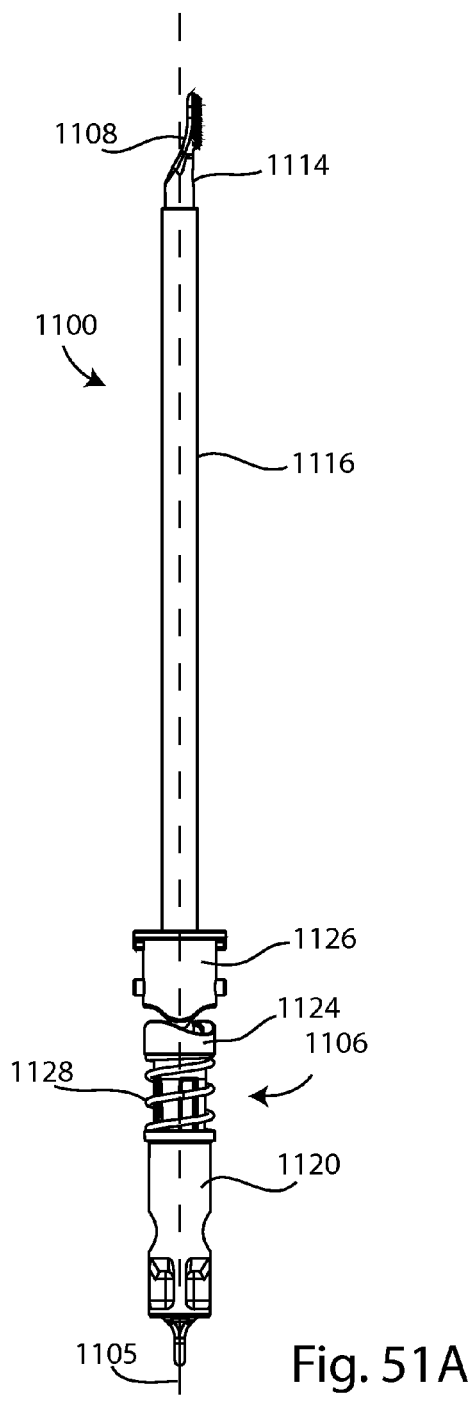
FIG. 51A is a side view of the reciprocating surgical instrument of FIG. 50 with an outer housing removed.
Figure 51B:
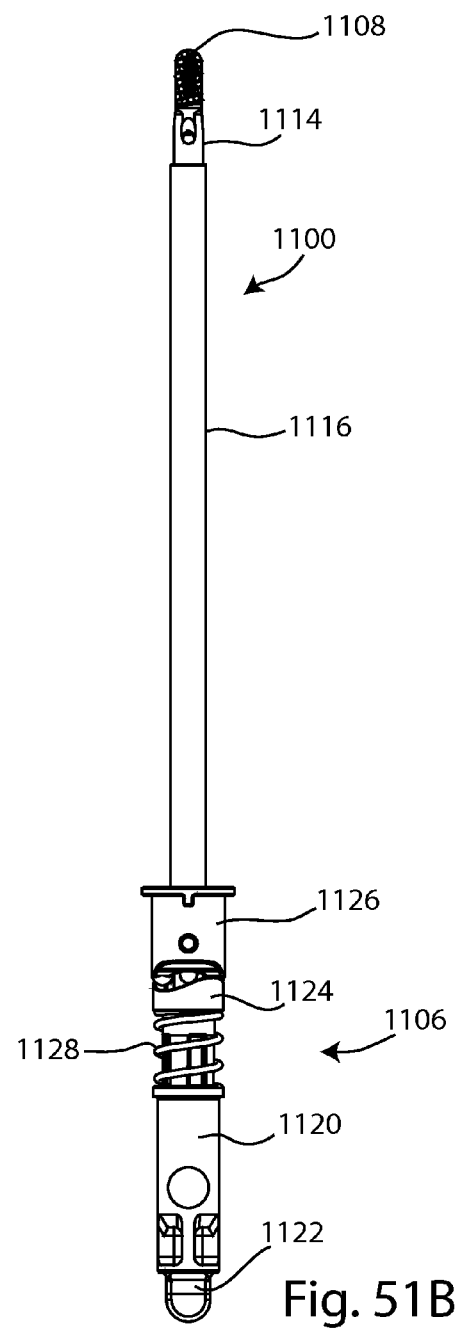
FIG. 51B is a bottom view of the reciprocating surgical instrument of FIG. 50 with the outer housing removed.

FIGS. 51A and 51B show side and bottom views of reciprocating surgical instrument 1100, respectively. The outer housing 1118 has been removed to reveal the juxtaposition of the rotatable cam 1124 relative to the fixed cam 1126 and the longitudinal axis 1105.

With reference to FIGS. 51A-52, the reciprocating surgical instrument 1100 will be described in the generally proximal to distal direction. At the proximal end of the assembled system, hub 1120 includes a driver connection 1122, which may be a tab shaped to be coupled with a complimentarily shaped driver in a powered hand piece (not shown), as described earlier. When hub 1120 is received in housing 1118 (as shown in FIG. 50), an outer housing end piece 1141 can be coupled to the outer housing 1118 to retain the hub 1120 within the outer housing 1118. In one example, the outer housing end piece 1141 can be shaped and configured to couple to the outer housing 1118 via a snap-fit mechanism. A coupler washer 1119 (not shown) may also be located between the hub 1120 and the outer housing end piece 1121 to help promote free rotation of the hub 1120 relative to the outer housing 1118, thus reducing friction and potentially preventing overheating or melting of the two components.

In one example, hub 1120 can further include a connection feature 1121 shaped to interact with the rotatable cam 1124 in a sliding fashion. In this example, the rotatable cam 1124 is at least partially captured within the connection feature 1121 of the hub 1120 such that the rotatable cam 1124 is rotated with the hub 1120 about longitudinal axis 1105. The rotatable cam 1124 can also reciprocate translationally with respect to the hub 1120 along the longitudinal axis 1105 as the hub 1120 and the rotating cam 1124 rotate about the longitudinal axis 1105.

In another example, the hub (not shown) is at least partially captured within a connection feature formed within the rotating cam (not shown) such that the rotating cam is rotatably carried with the hub about the longitudinal axis 1105. The rotatable cam can also reciprocate translationally with respect to the hub along the longitudinal axis 1105 as the hub and the rotating cam rotate about the longitudinal axis 1105.

In a particular example, the hub connection feature 1121 may be a hex feature (not shown), and the cam 1124 has a correspondingly shaped connection feature 1125 (not shown).

Figure 59:
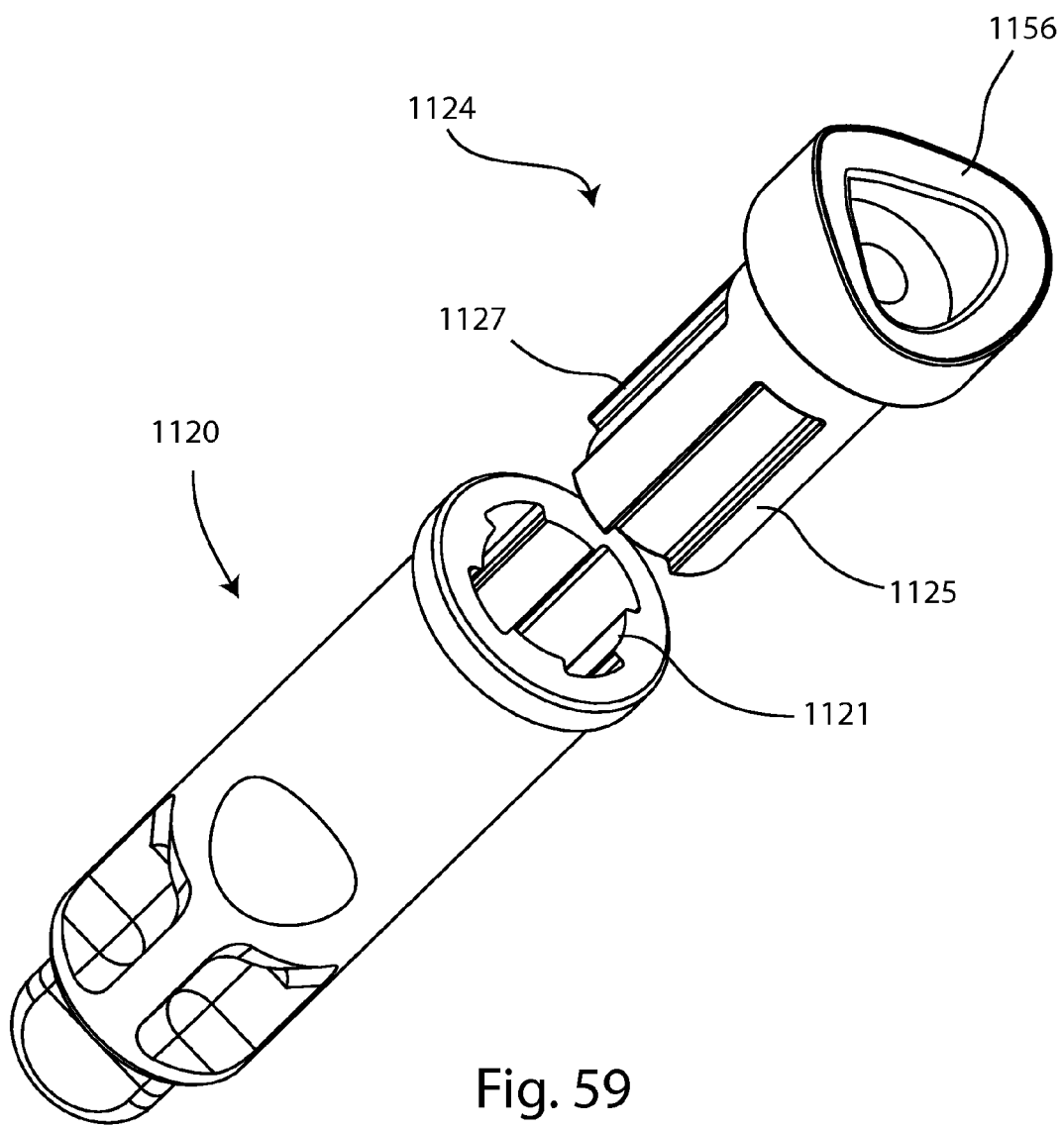
FIG. 59 is an isometric view of the rotatable cam of FIG. 56A and the rotatable hub of FIG. 58A prior to assembly.
Figure 60A:
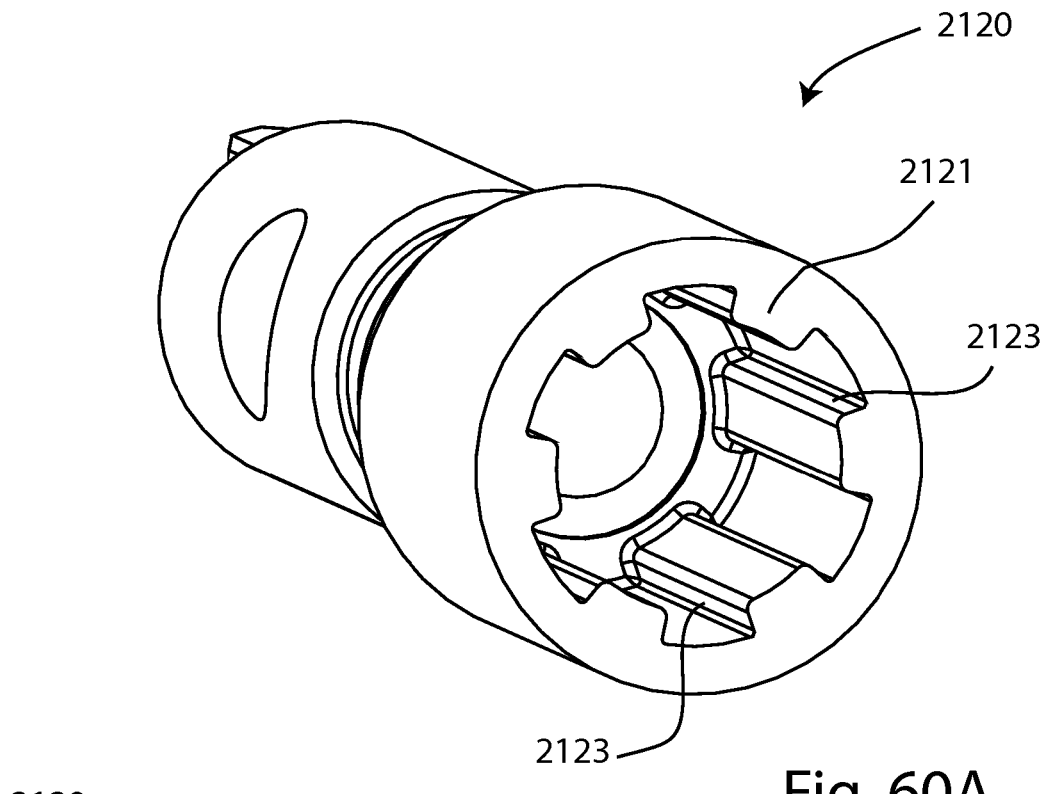
FIG. 60A is an isometric view of another rotatable hub in accordance with another example of the present disclosure.
Figure 60B:
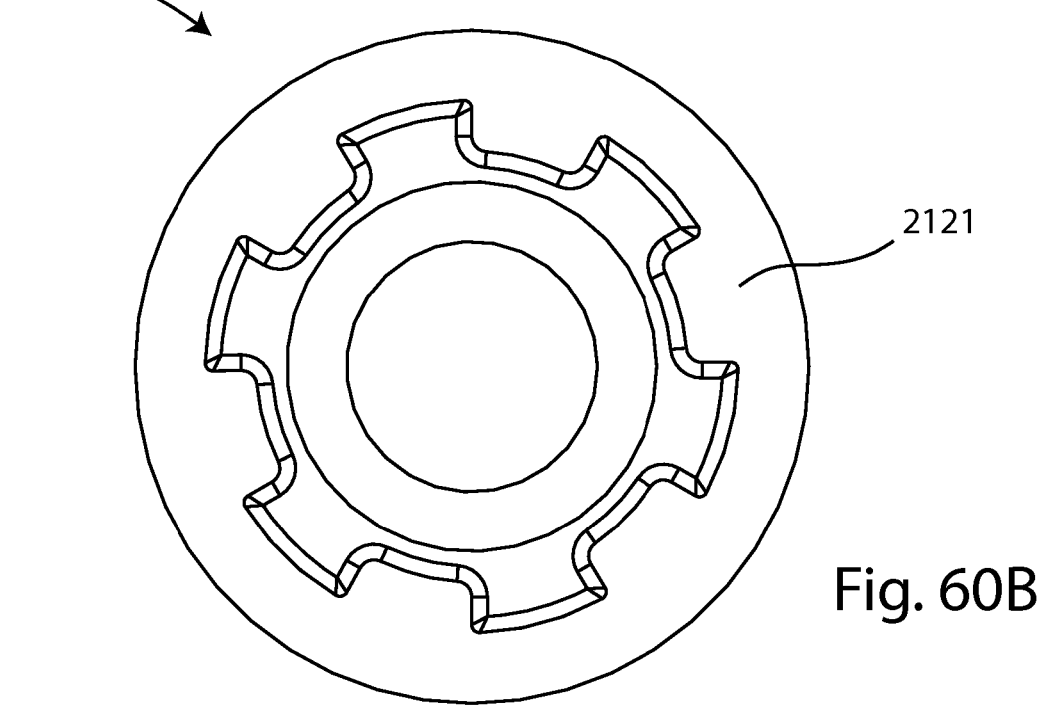
FIG. 60B is a top view of the distal end of the rotatable hub of FIG. 60A.
Figure 61A:
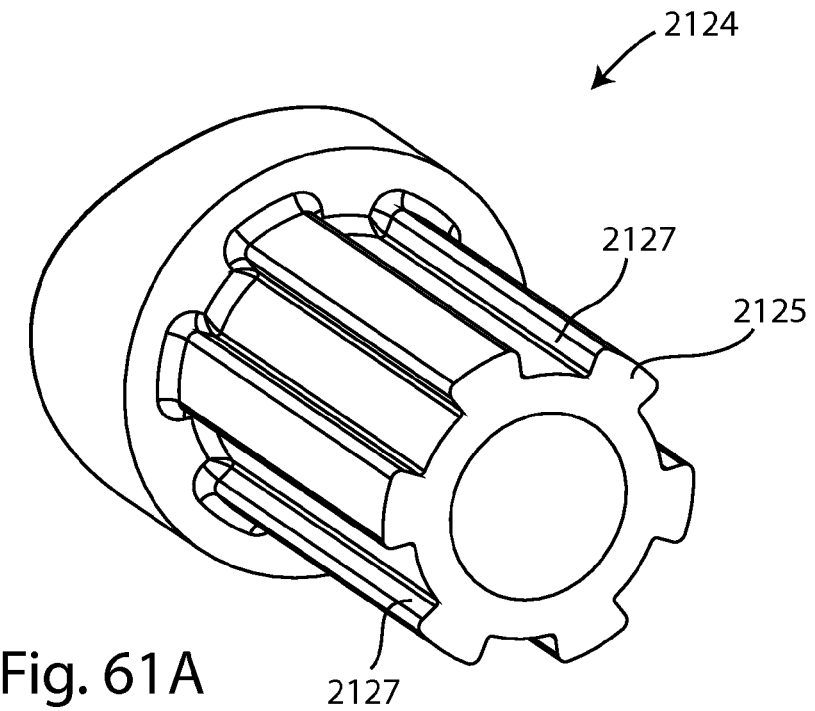
FIG. 61A is an isometric view of another rotatable cam configured to interact with the rotatable hub of FIG. 60A.
Figure 61B:
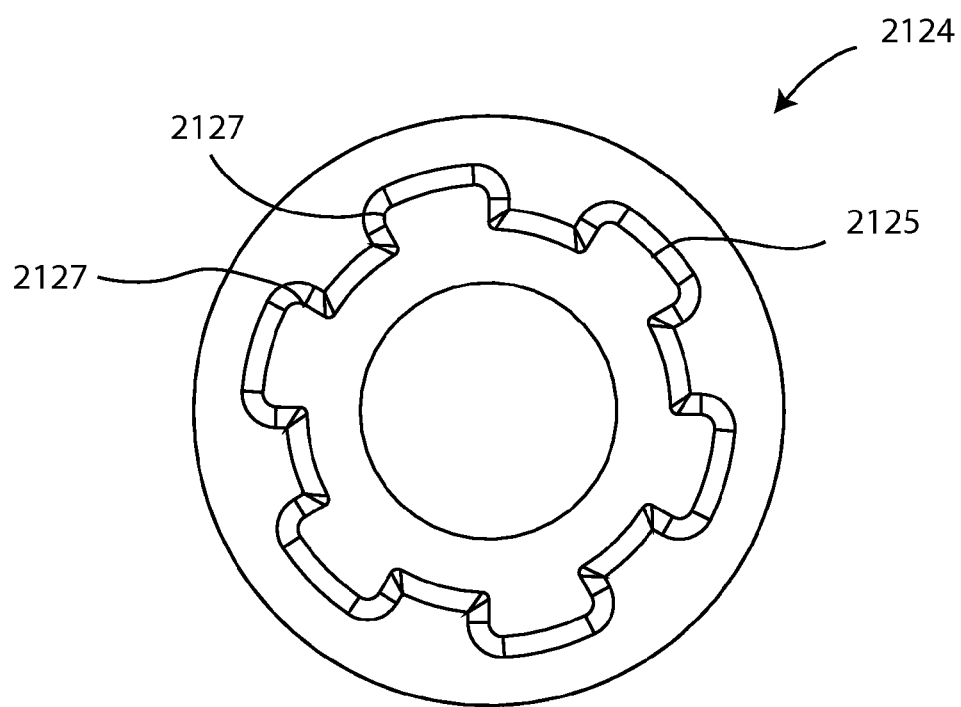
FIG. 61B is a bottom view of the proximal end of the rotatable cam of FIG. 61A.
Figure 62A:
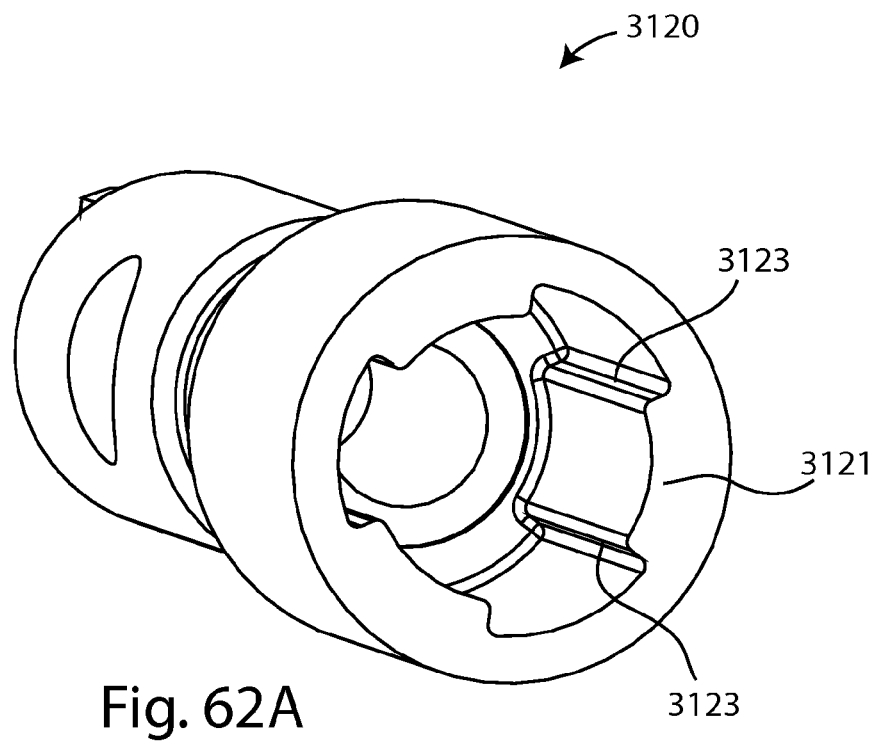
FIG. 62A is an isometric view of yet another rotatable hub in accordance with another example of the present disclosure.
Figure 62B:
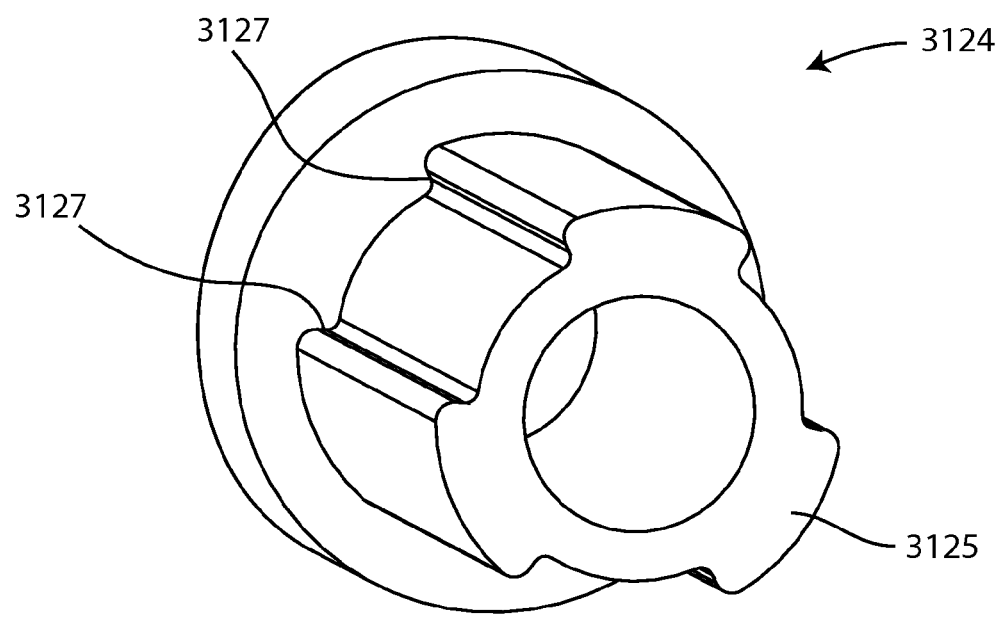
FIG. 62B is an isometric view of yet another rotatable cam configured to interact with the rotatable hub of FIG. 62A.
Figure 63A:
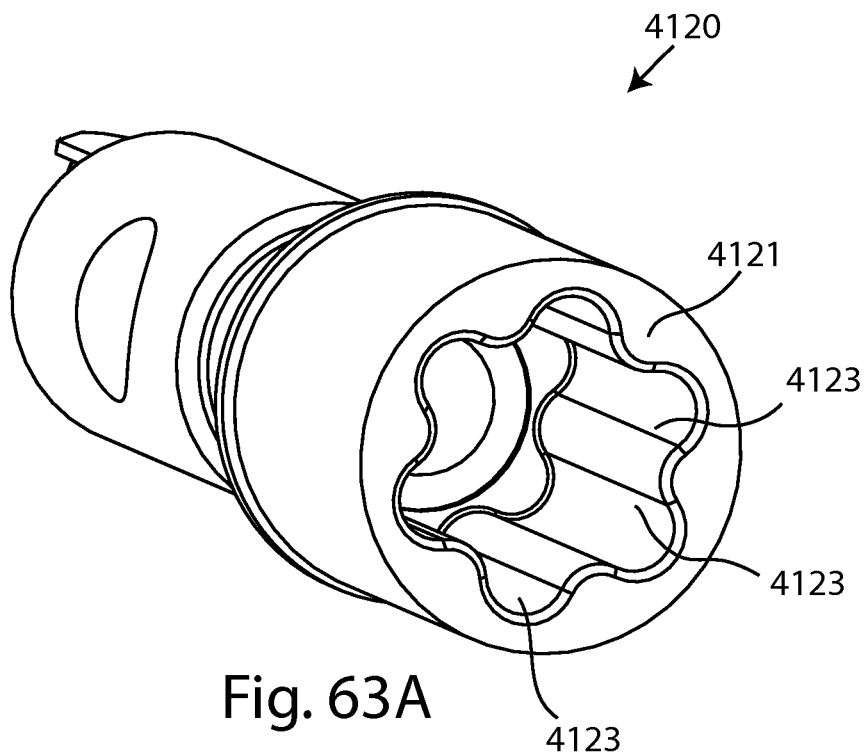
FIG. 63A is an isometric view of yet another rotatable hub in accordance with another example of the present disclosure.
Figure 63B:
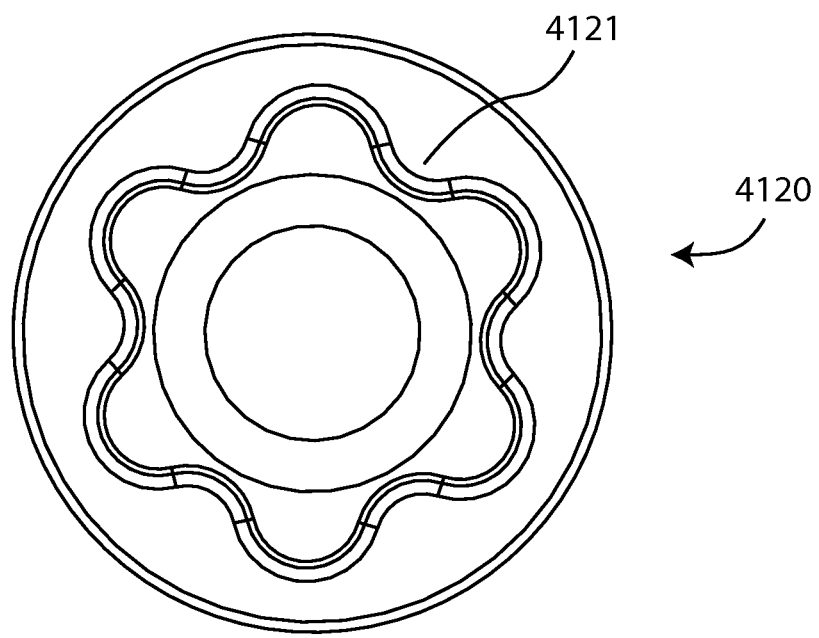
FIG. 63B is a top view of the distal end of the rotatable hub of FIG. 63A.
Figure 64A:
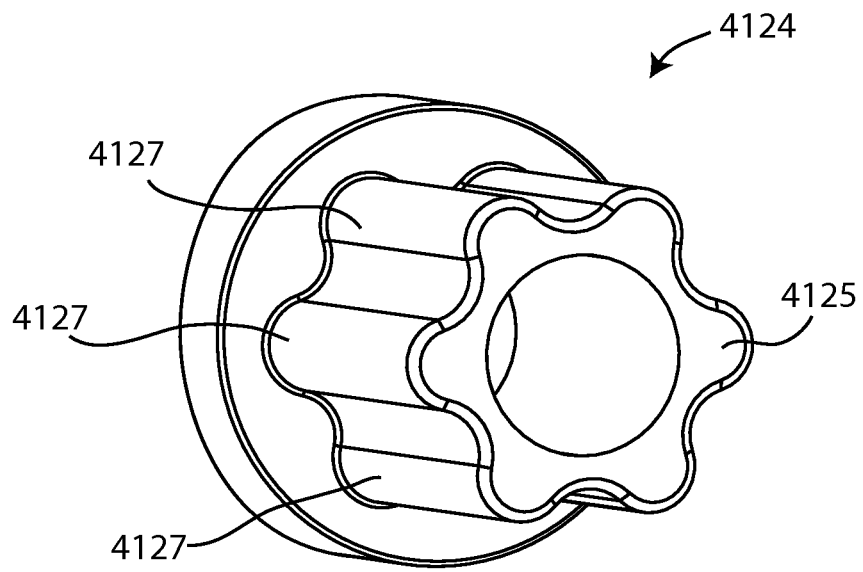
FIG. 64A is an isometric view of yet another rotatable cam configured to interact with the rotatable hub of FIG. 63A.
Figure 64B:
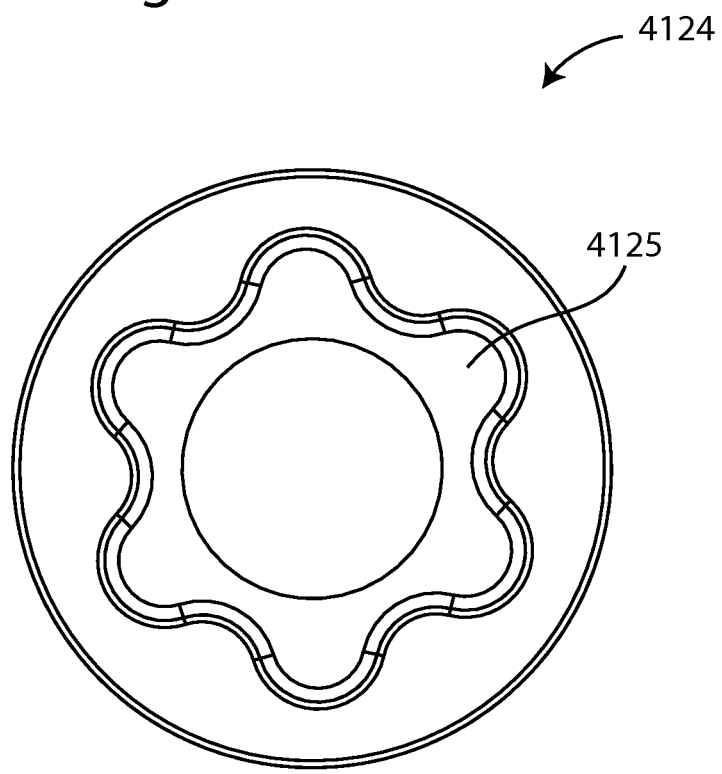
FIG. 64B is a bottom view of the proximal end of the rotatable cam of FIG. 64A.
Figure 65A:
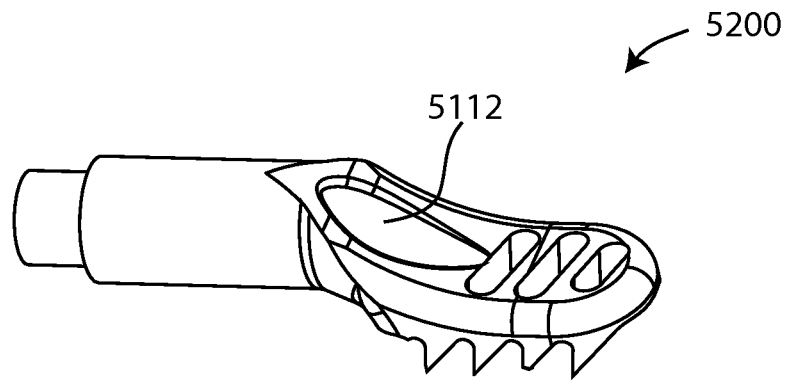
FIG. 65A is an isometric view of a distal end of a tissue removal member according to one example of the present disclosure.
Figure 65B:
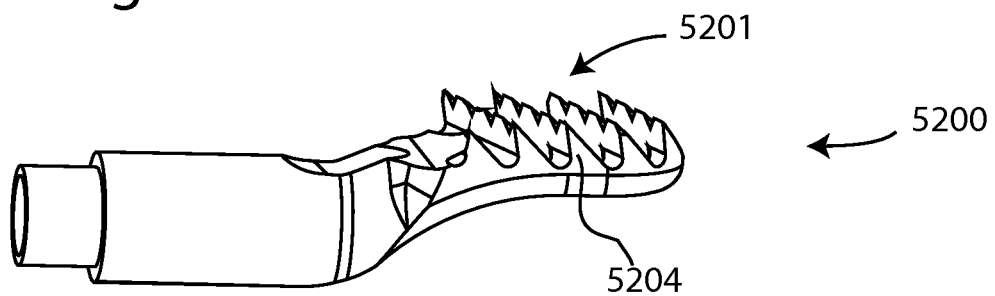
FIG. 65B is another isometric view of the tissue removal member of FIG. 65A.
Figure 65C:
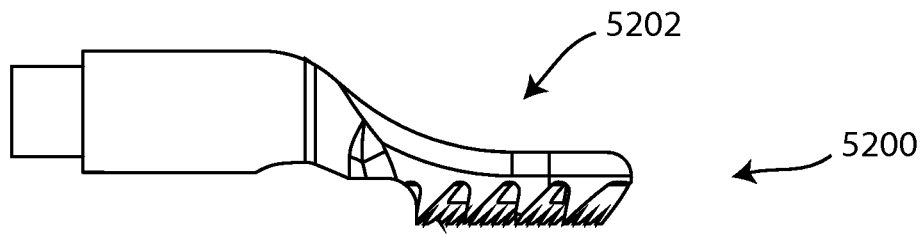
FIG. 65C is a side view of the tissue removal member of FIG. 65A.
Figure 65D:
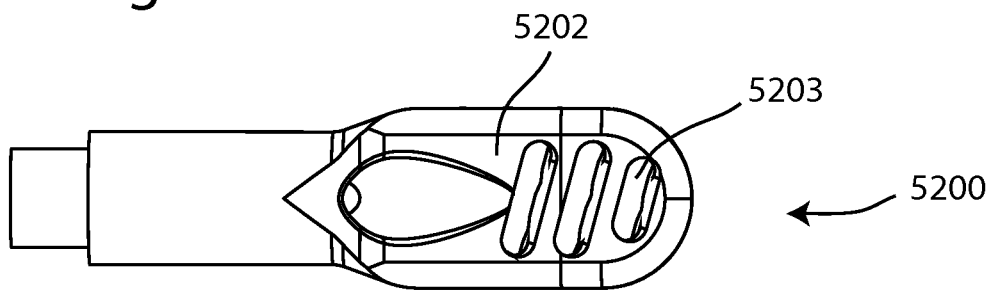
FIG. 65D is a top view of the tissue removal member of FIG. 65A.
Figure 66A:
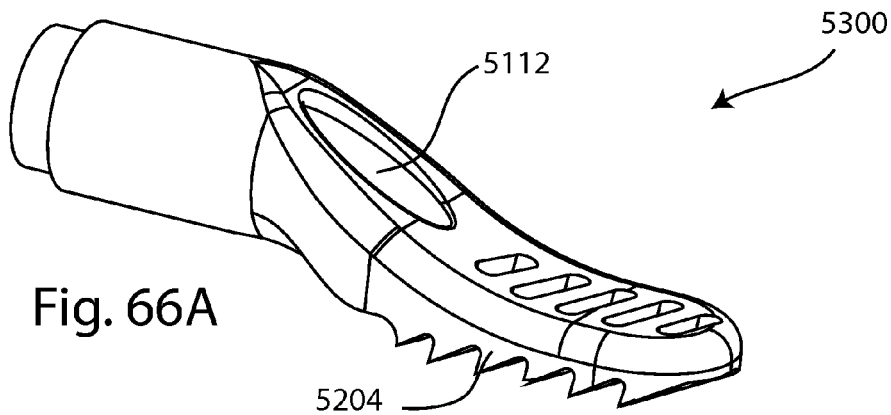
FIG. 66A is an isometric view of another tissue removal member according to another example of the present disclosure.
Figure 66B:
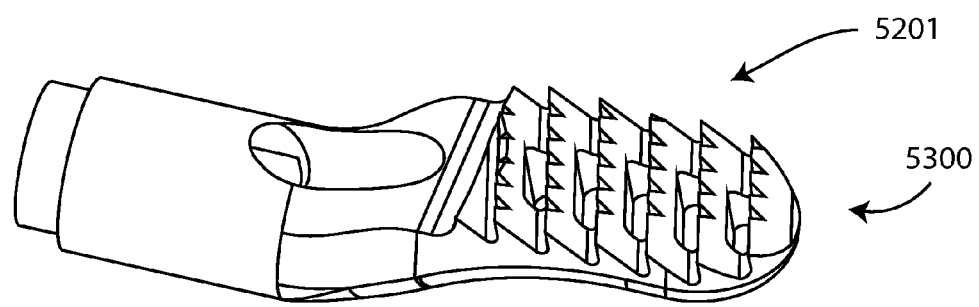
FIG. 66B is another isometric view of the tissue removal member of FIG. 66A.
Figure 66C:
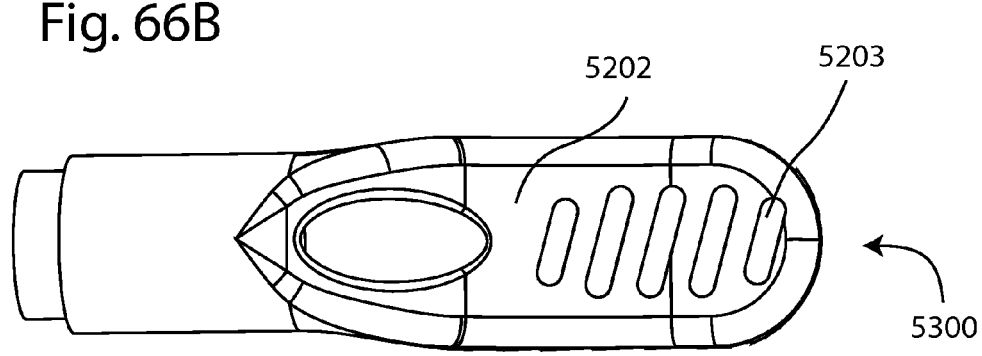
FIG. 66C is a top view of the tissue removal member of FIG. 66A.
Figure 67A:
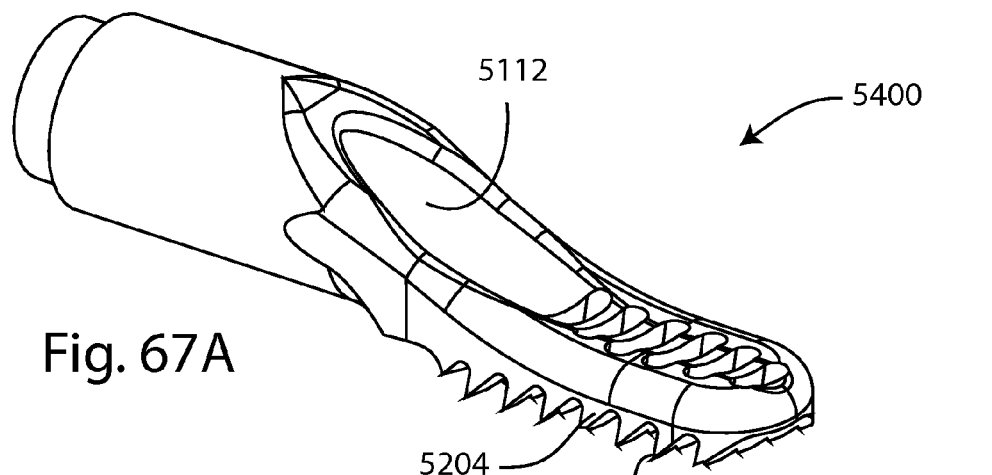
FIG. 67A is an isometric view of yet another tissue removal member according to another example of the present disclosure.
Figure 67B:
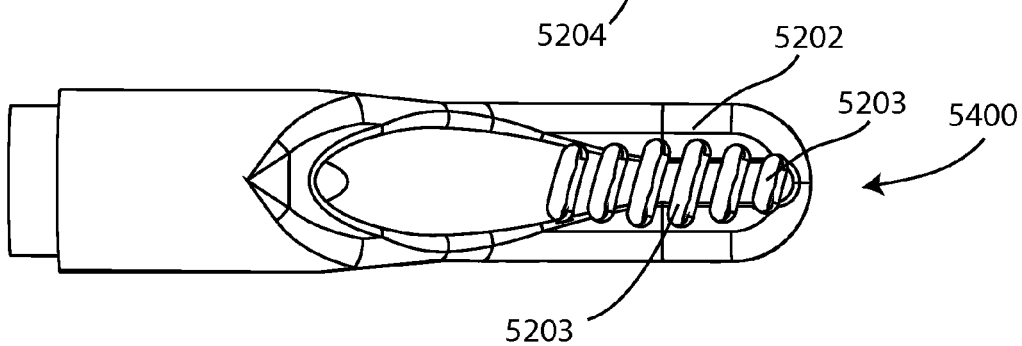
FIG. 67B is a top view of the tissue removal member of FIG. 67A.
Figure 67C:
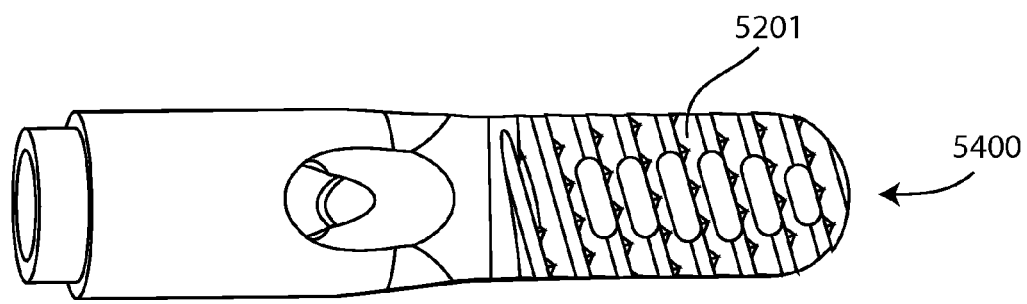
FIG. 67C is a bottom view of the tissue removal member of FIG. 67A.
Figure 68A:
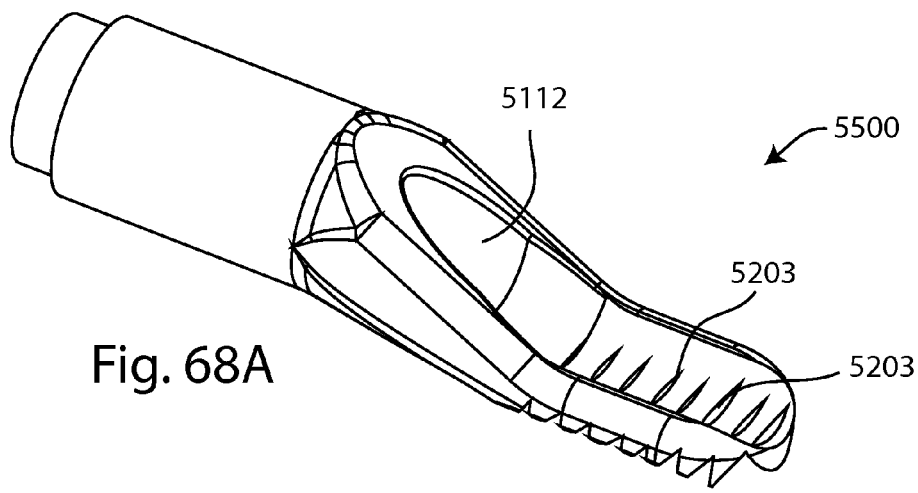
FIG. 68A is an isometric view of yet another tissue removal member according to another example of the present disclosure.
Figure 68B:
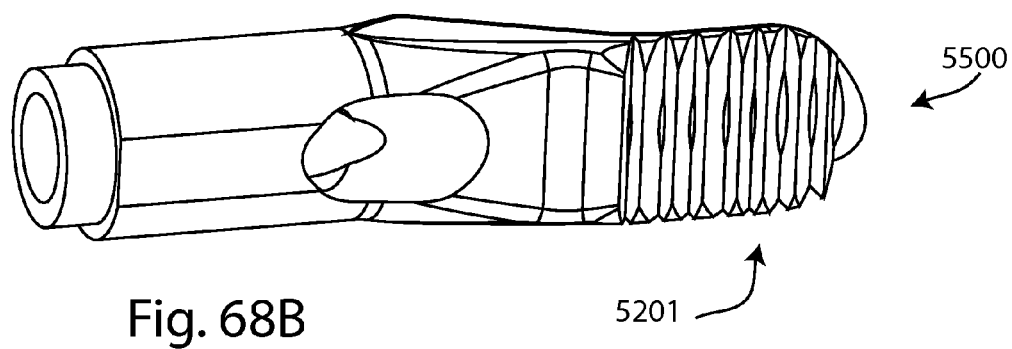
FIG. 68B is an isometric view of the tissue removal member of FIG. 68A.
Figure 68C:
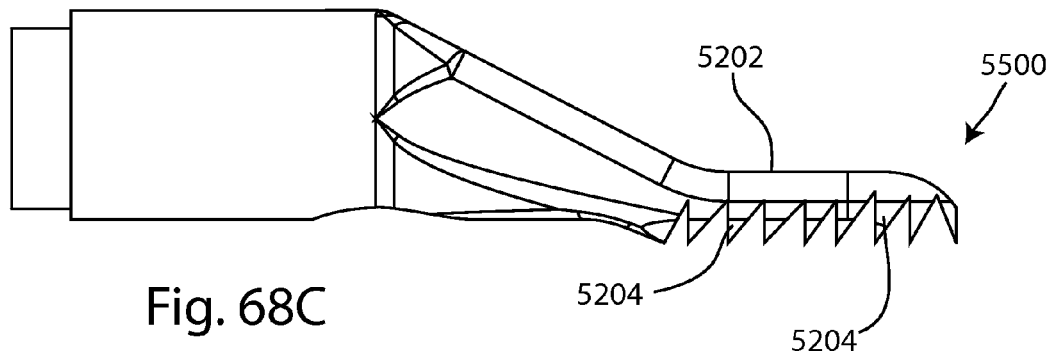
FIG. 68C is a side view of the tissue removal member of FIG. 68A.

In another example, the hub connection feature 1121 and corresponding shaped cam connection feature 1125 can have a somewhat cross shape as can be seen throughout FIGS. 50-59, which may include multiple dove-tail shaped connections around a circular member. FIG. 59 shows the hub 1120 and cam 1124 as the cam 1124 is about to be inserted into the hub 1120.

Figure 56A:
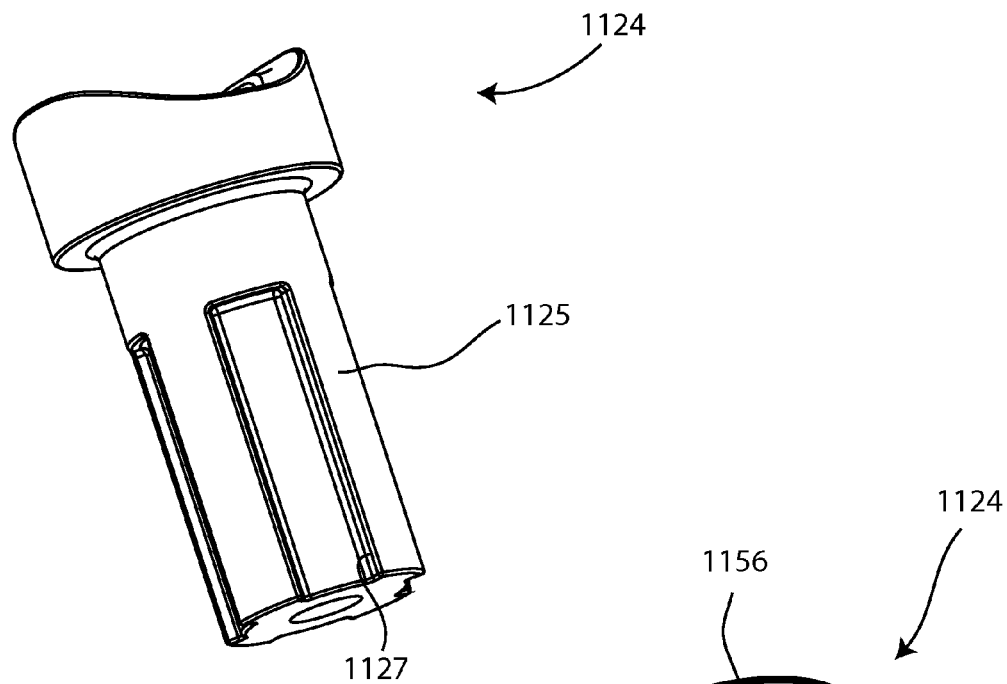
FIG. 56A is an isometric view of a rotatable cam in accordance with one example of the present disclosure.
Figure 56B:
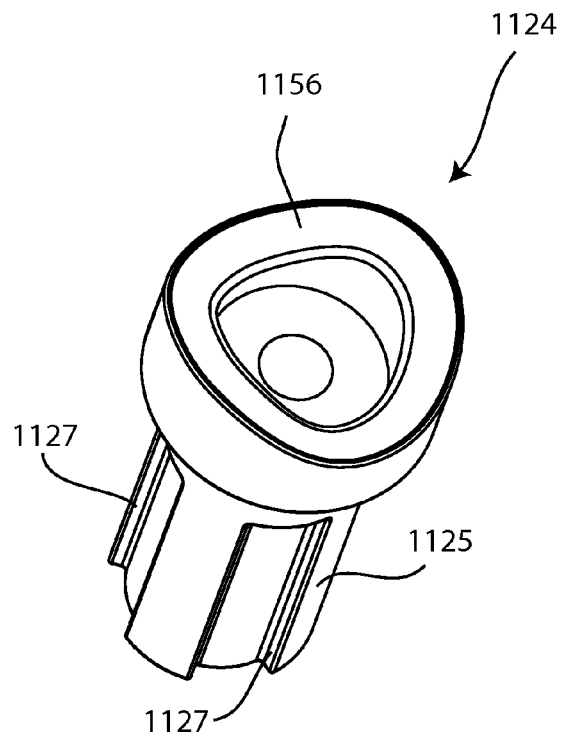
FIG. 56B is another isometric view of the rotatable cam of FIG. 56A.
Figure 58A:
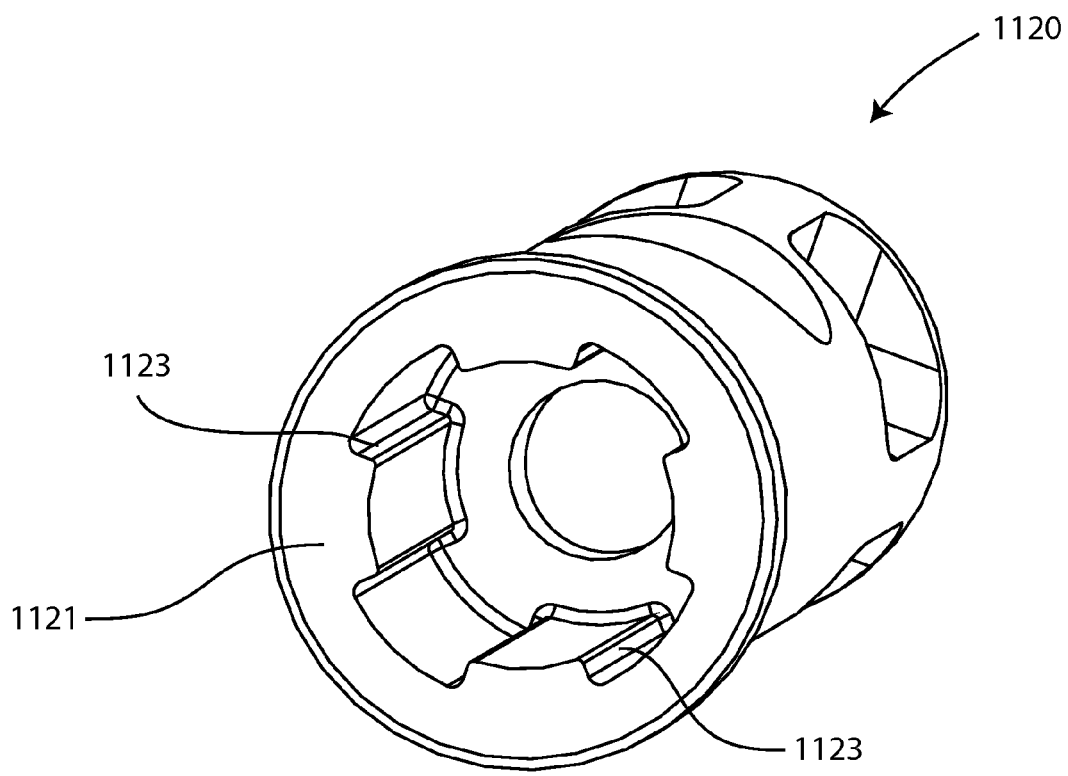
FIG. 58A is an isometric view of a rotatable hub in accordance with one example of the present disclosure.
Figure 58B:
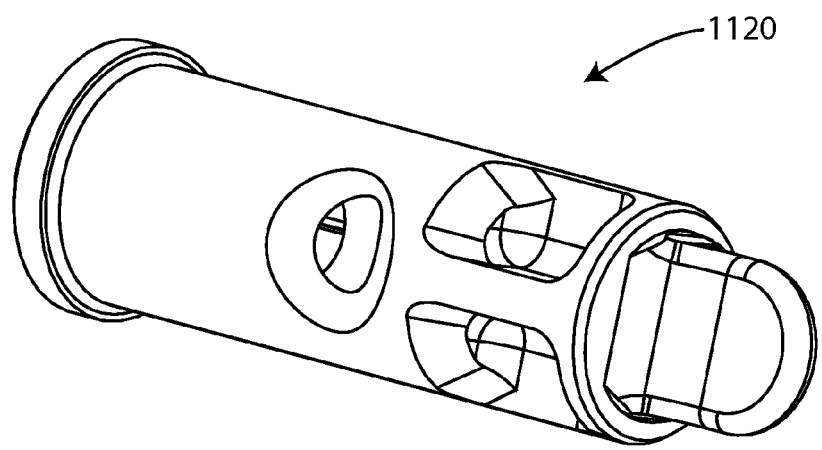
FIG. 58B is another isometric view of the rotatable hub of FIG. 58A.

The hub 1120 includes at least one elongated driving surface 1123 that can run substantially parallel to the longitudinal axis 1105. The cam 1124 is correspondingly shaped to complement the hub 1120 and can include at least one elongated drive surface 1127 that runs substantially parallel to the longitudinal axis 1105. When assembled, the hub 1120 and cam 1124 form at least one interface between the at least one elongate driving surface 1123 (FIG. 58A) and the at least one elongate driven surface 1127 (FIGS. 56A-56B). The interface forms a contact surface area through which rotational forces are transmitted from the at least one elongate driving surface 1123 of the rotary hub 1120 to the complimentarily shaped at least one elongate driven surface 1127 of the cam 1124. This allows the forces to be spread out over a wide area to reduce point load forces between the driving and the driven surfaces, which reduces friction and wear between the driving and the driven surfaces as the cam 1124 rotates and reciprocally translates with respect to the hub 1120.

FIGS. 60A-64B illustrate yet other examples of hub and cam designs which may be used according to the present disclosure. Referring to FIGS. 56-64B, each of the different hubs 1120, 2120, 3120, 4120 disclosed herein can include at least one elongate driving surface 1123, 2123, 3123, 4123, respectively, that can run substantially parallel to the longitudinal axis. Each of the different cams 1124, 2124, 3124, 4124 disclosed herein is correspondingly shaped to complement the appropriate hub design and can include at least one elongate driven surface 1127, 2127, 3127, 4127, respectively, that runs substantially parallel to the longitudinal axis.

Referring to FIGS. 51A-59, inner shaft 1114 can extend proximally through cam 1124, and can be engaged with cam 1124 through washers 1152 and snap rings 1154 so that inner shaft 1114 does not rotate with cam 1124, but is reciprocatively carried with cam 1124 between a proximal, or retracted, and a distal, or extended, position. Distal to cam 1124, a fixed cam 1126 may be connected to outer sleeve 1116, and may be rigidly connected to outer housing 1118. Fixed cam 1126 may be referred to as a first cam, and cam 1124 may be referred to as a second cam or rotatable cam. As rotatable cam 1124 rotates, undulating fixed cam surface 1180 (FIG. 52) on fixed cam 1126 and undulating rotatable cam surface 1156 on rotatable cam 1124 cooperate to convert the rotary motion of the hub 1120 and rotatable cam 1124 to reciprocating movement of the rotatable cam 1124 and inner shaft 1114. At least one ball bearing 1190 may be positioned between the cam surfaces 1156, 1180 to reduce friction between the cam surfaces. The surfaces 1156, 1180 may therefore be dished or concave to complement the ball bearing 1190, as may be appreciated in FIGS. 53-54 and 57. A spring 1128 can be positioned between the hub 1120 and rotatable cam 1124, and the spring bias of spring 1128 acts to return the rotatable cam 1124, inner shaft 1114 and head 1108 to the distal position. It is appreciated that in other embodiments, the relative sequence of the system components may vary to accomplish the same objectives. For example, in another embodiment the relative positions of the rotatable cam 1124 and fixed cam 1126 may be reversed, or the location of the spring 1128 may differ.

Figure 53:
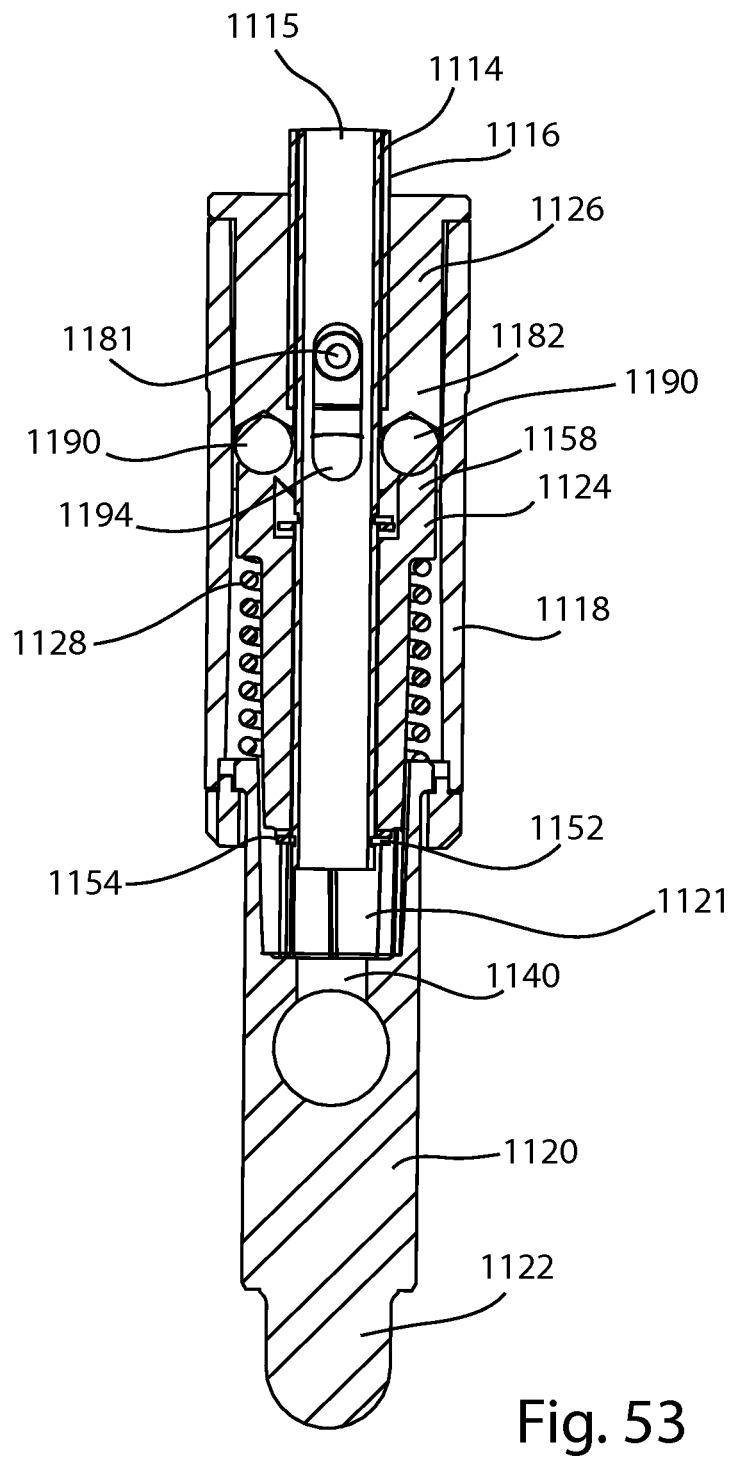
FIG. 53 is a longitudinal cross-sectional view of a handle portion and a segment of a shaft portion of the reciprocating surgical instrument of FIG. 50 in a retracted position.
Figure 54:
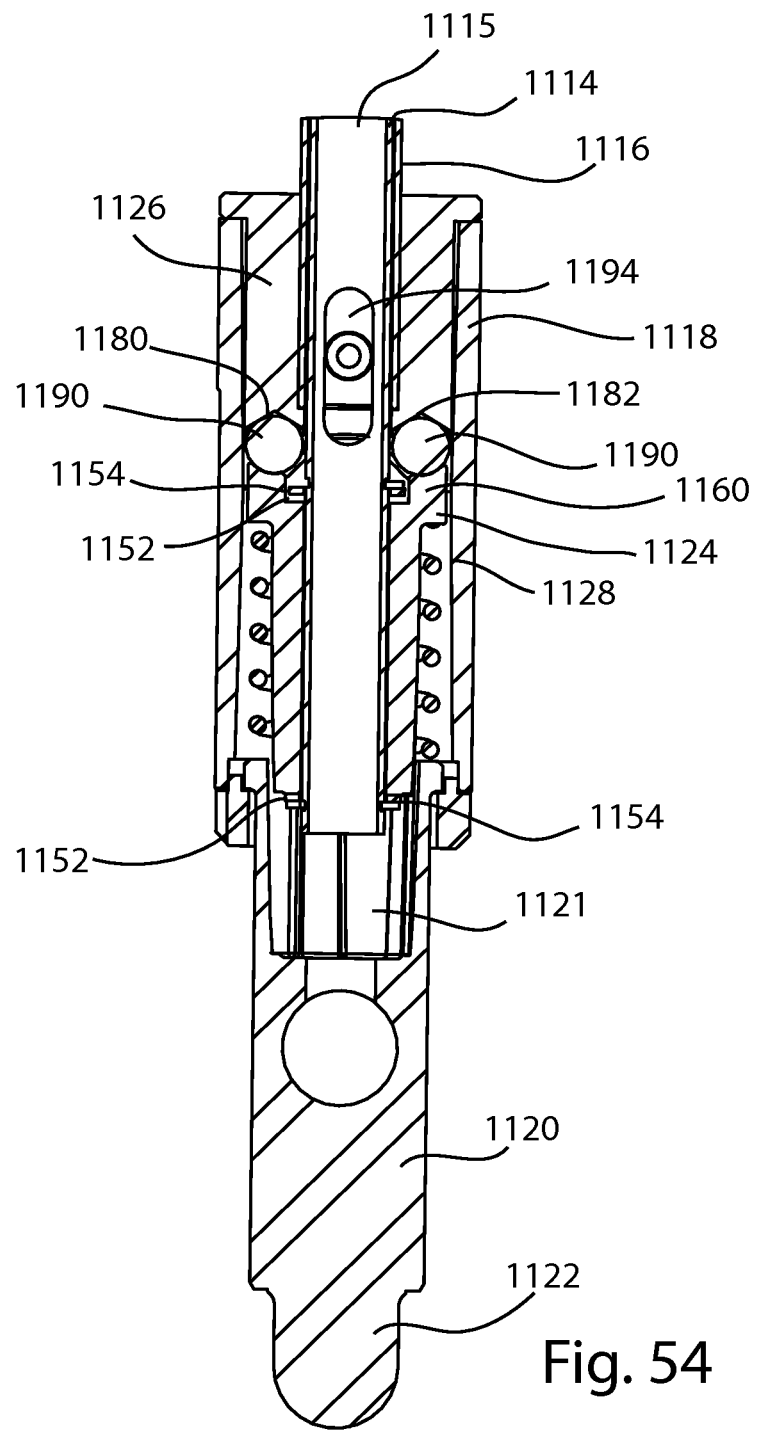
FIG. 54 is a longitudinal cross-sectional view of a handle portion and a segment of a shaft portion of the reciprocating surgical instrument of FIG. 50 in the extended position.
Figure 55A:
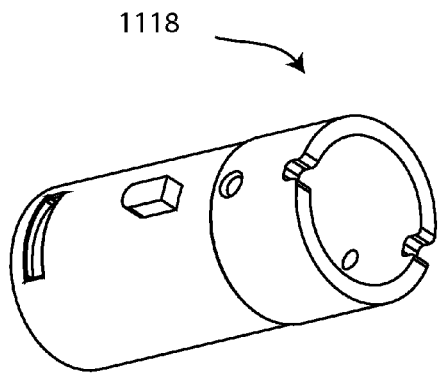
FIG. 55A is an isometric view of an outer housing of the reciprocating surgical instrument of FIG. 50.
Figure 55B:
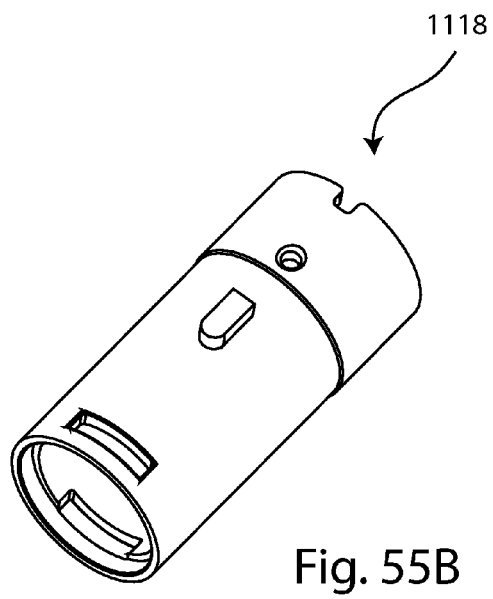
FIG. 55B is another isometric view of the outer housing of the reciprocating surgical instrument of FIG. 55A.
Figure 55C:
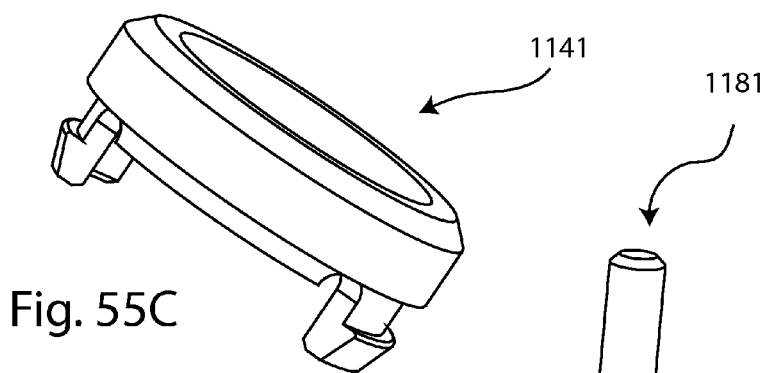
FIG. 55C is an isometric view of an outer housing end piece of the reciprocating surgical instrument of FIG. 50.
Figure 55D:
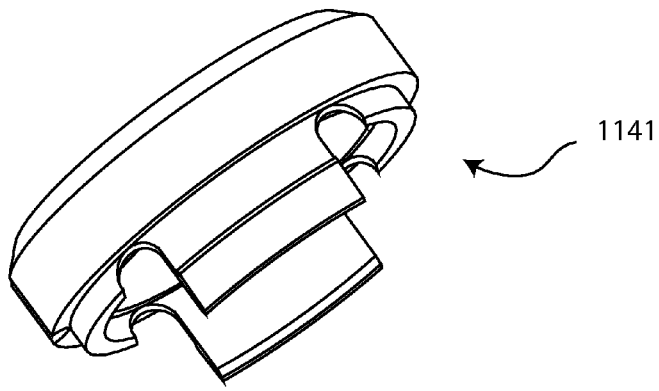
FIG. 55D is another isometric view of the outer housing end piece of the reciprocating surgical instrument of FIG. 55C.
Figure 55E:
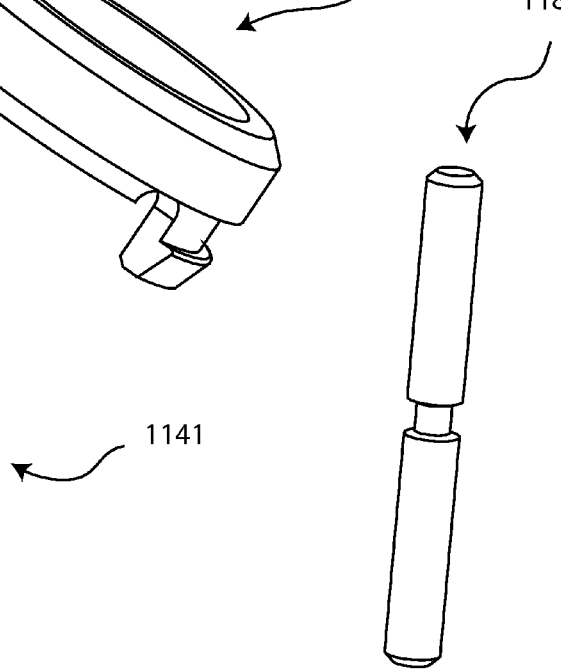
FIG. 55E is an isometric view of an anti-rotation member of the reciprocating surgical instrument of FIG. 50.

FIGS. 53 and 54 show longitudinal cross-sectional views of the handle portion 1106 of instrument 1100 in the retracted and extended positions, respectively.

The reciprocating instrument systems disclosed herein can incorporate a variety of working members, tissue removal members, or heads located at an end of the translation member. FIGS. 65A-69C illustrate tissue removal members 5200, 5300, 5400, 5500, and 5600 which are rasp heads. Each of these rasp heads can have a top surface 5202 which can be convex, concave, flat or combinations thereof. Each of these rasp heads can also have a working surface 5201 with at least one tooth 5204 or cutting edge arranged on the working surface 5201. Multiple teeth 5204 or cutting edges may be arranged in at least one row. In one embodiment, the rasp head 5200 has four rows of teeth 5204. In another embodiment, the rasp head 5300 has six rows of teeth 5204. In yet another embodiment, the rasp heads 5400, 5500 have eight rows of teeth 5204. In still other embodiments, the rasp head 5600 has seven rows of teeth 5204. The rows of teeth 5204 may be orthogonally or obliquely arranged relative to a longitudinal axis of the translation member; both arrangements are shown.

Each of the working members disclosed herein can have one or more suction ports or suction pathways, such as suction ports 1112, 5112. Each of the working members disclosed herein can also have one or more apertures, such as aperture 5203, formed between the working surface, such as 5201, and the top surface, such as 5202. Each of the working members disclosed herein can have rows of teeth, such as 5204, arranged to remove tissue as the working member reciprocates and/or to channel the removed tissue toward the at least one aperture and the suction pathway. In some embodiments, the at least one tooth arranged in at least one row is perpendicularly transverse to the longitudinal axis of the working member. In other embodiments, the at least one tooth arranged in at least one row is non-perpendicularly transverse to the longitudinal axis of the working member. In each of the embodiments disclosed herein, the at least one tooth arranged in at least one row can be angled in the proximal or distal directions to help direct the removed tissue toward or away from the suction pathway. In some embodiments, the at least one aperture is perpendicularly transverse to the longitudinal axis of the working member. In other embodiments, the at least one aperture is non-perpendicularly transverse to the longitudinal axis of the working member, or oblique to the longitudinal axis. In each of the embodiments disclosed herein, the at least one aperture can be angled in the proximal or distal directions to help direct the removed tissue toward or away from the suction pathway.

Figure 69A:
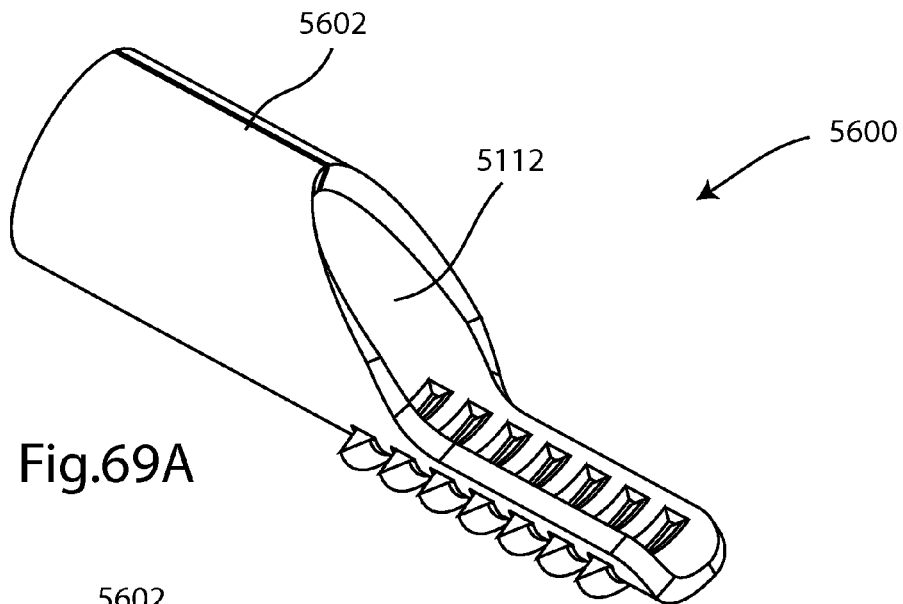
FIG. 69A is an isometric view of yet another tissue removal member according to another example of the present disclosure.
Figure 69B:
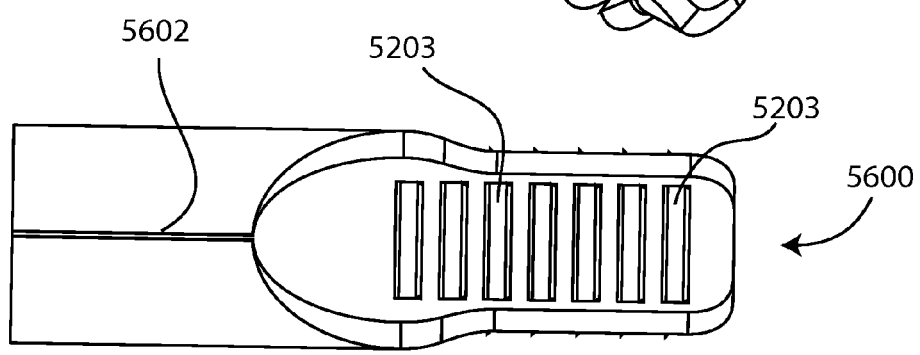
FIG. 69B is a top view of the tissue removal member of FIG. 69A.
Figure 69C:
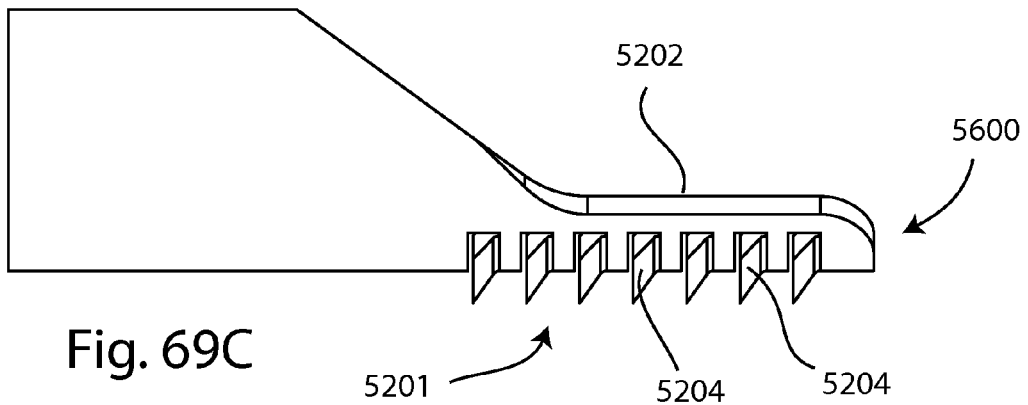
FIG. 69C is a side view of the tissue removal member of FIG. 69A.

Referring to FIGS. 69A-69C, the rasp head 5600 can be formed from a flat sheet of material by cutting, punching, bending or otherwise shaping the flat piece of material to form the rasp head 5600. In one example, a flattened projection of the rasp head 5600 may be stamped from a flat sheet of material in a primary operation. The stamped piece may then be bent around a mandrel in a secondary operation to form the tubular structure shown in FIGS. 69A-69C. A seam 5602 may occur along the rasp head 5600, and may be welded, brazed, glued, or otherwise fastened or secured in another secondary operation. The material can be metal, including but not limited to stainless steel, titanium or any other suitable material or metal.

Figure 70A:
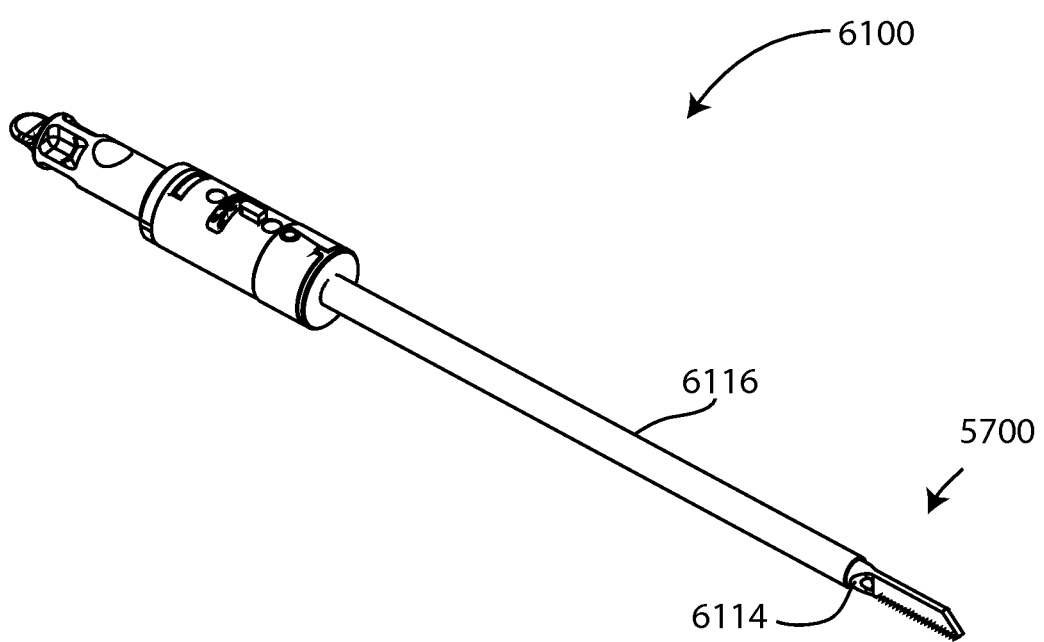
FIG. 70A is an isometric view of a reciprocating surgical instrument with a saw shaped working member attached to the distal end.
Figure 70B:
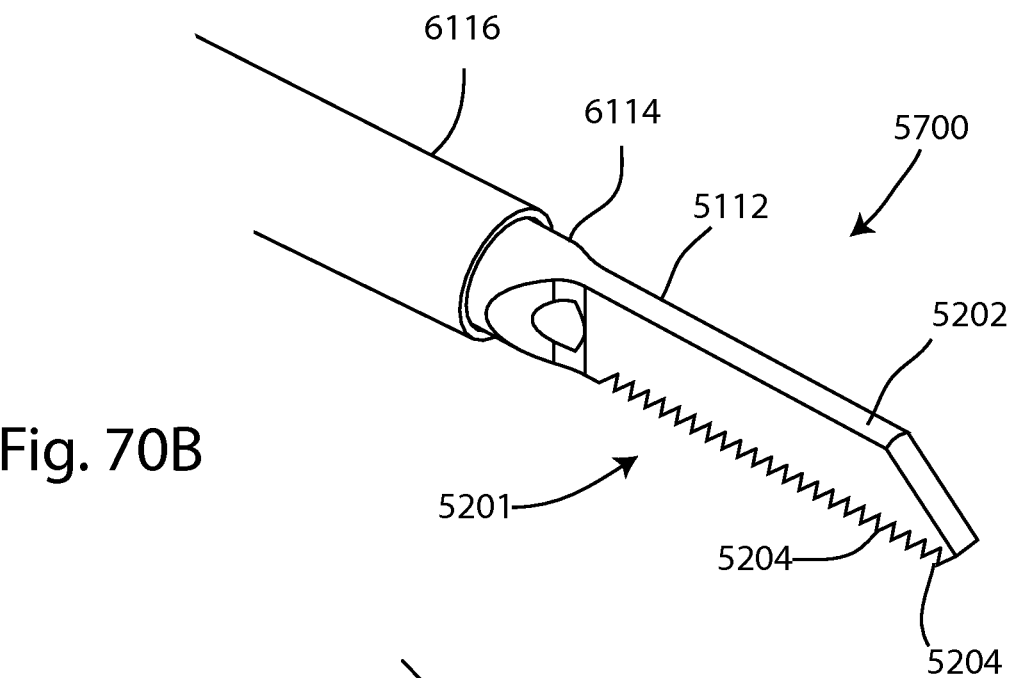
FIG. 70B is an enlarged view of the distal end of the reciprocating surgical instrument of FIG. 70A.
Figure 70C:
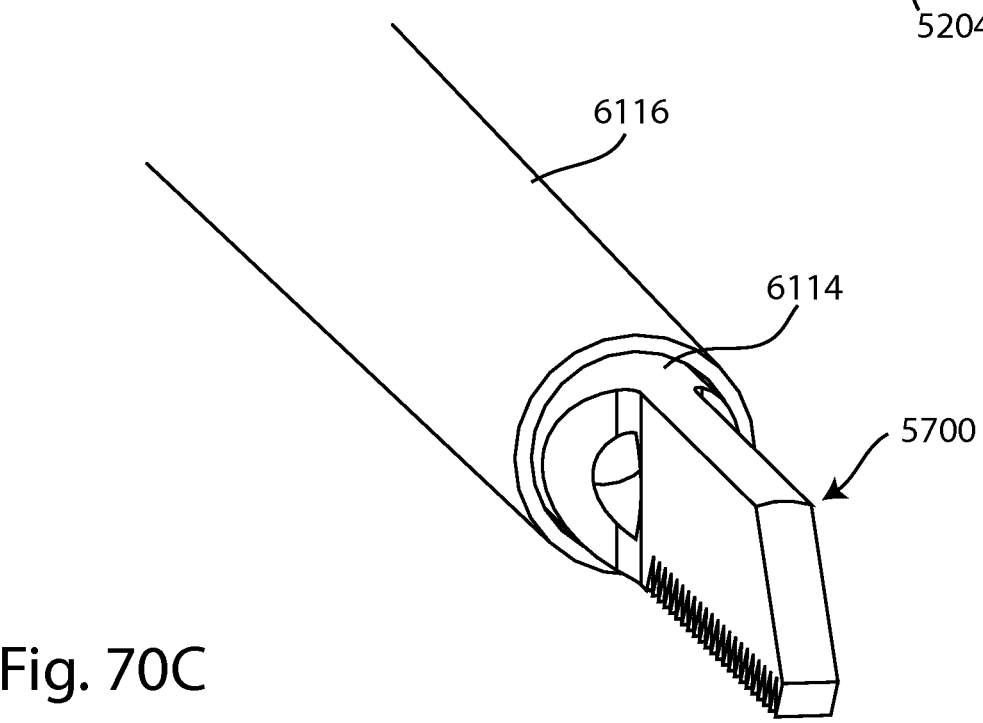
FIG. 70C is another isometric enlarged view of the distal end of the reciprocating surgical instrument of FIG. 70A.
Figure 71A:
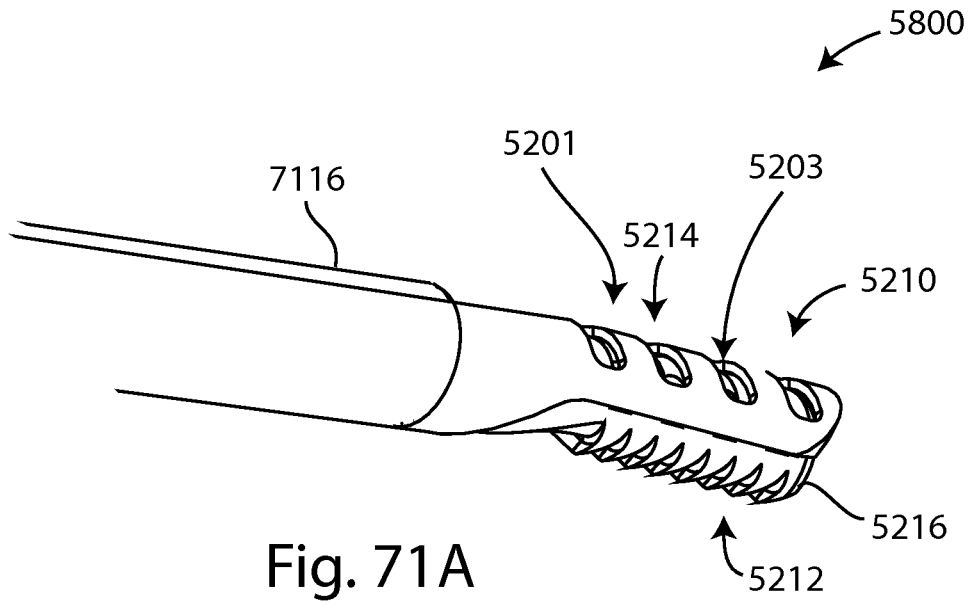
FIG. 71A is an isometric view of the working member with an enclosed shaver on one side and an open rasp on the other side.
Figure 71B:
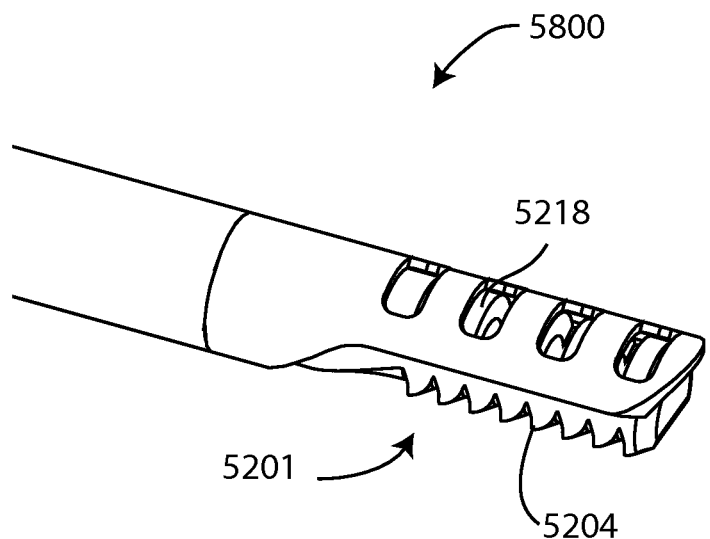
FIG. 71B is another isometric view of the working member of FIG. 71A.
Figure 71C:
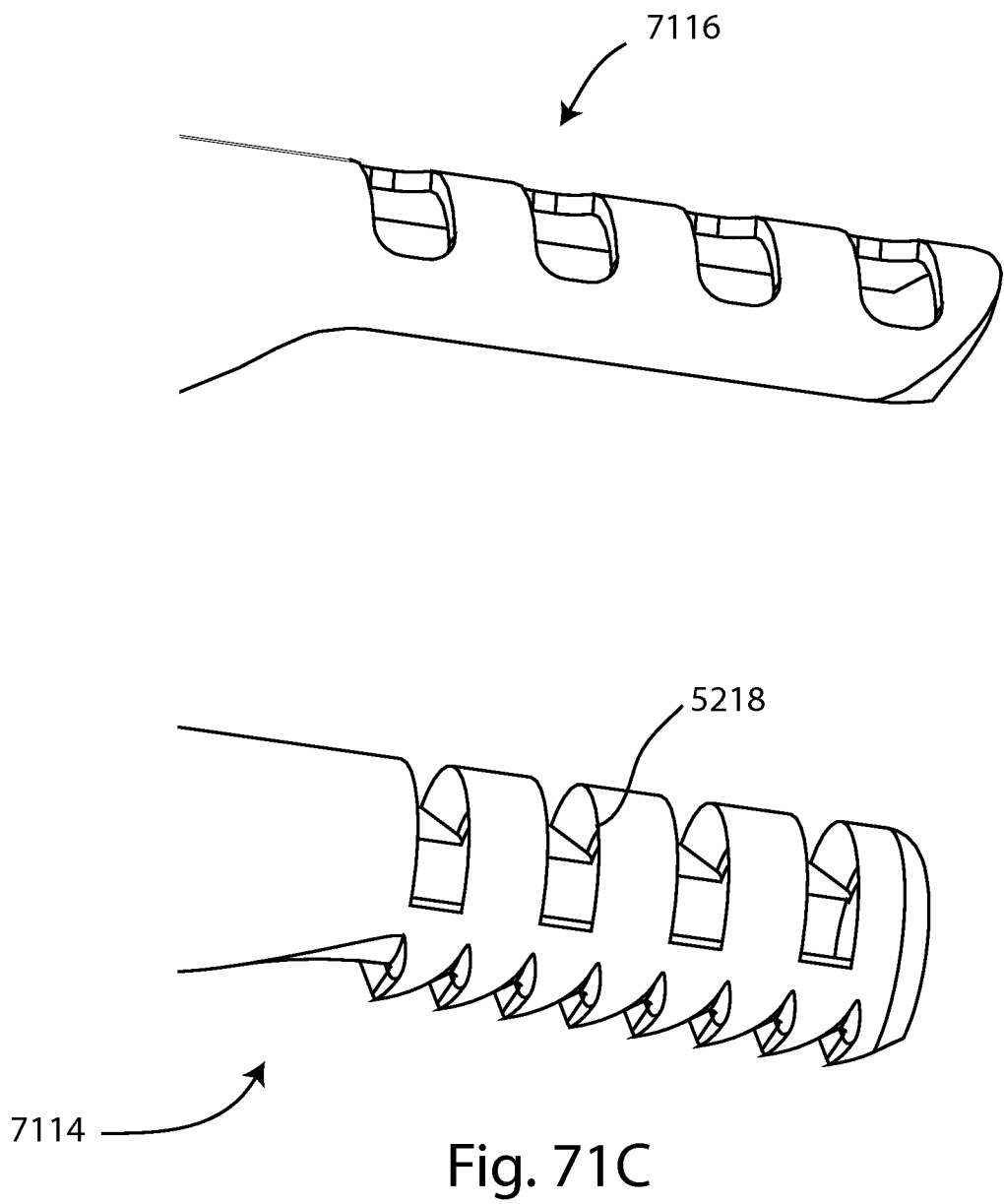
FIG. 71C is an isometric exploded view of the working member of FIG. 71A.
Figure 71D:
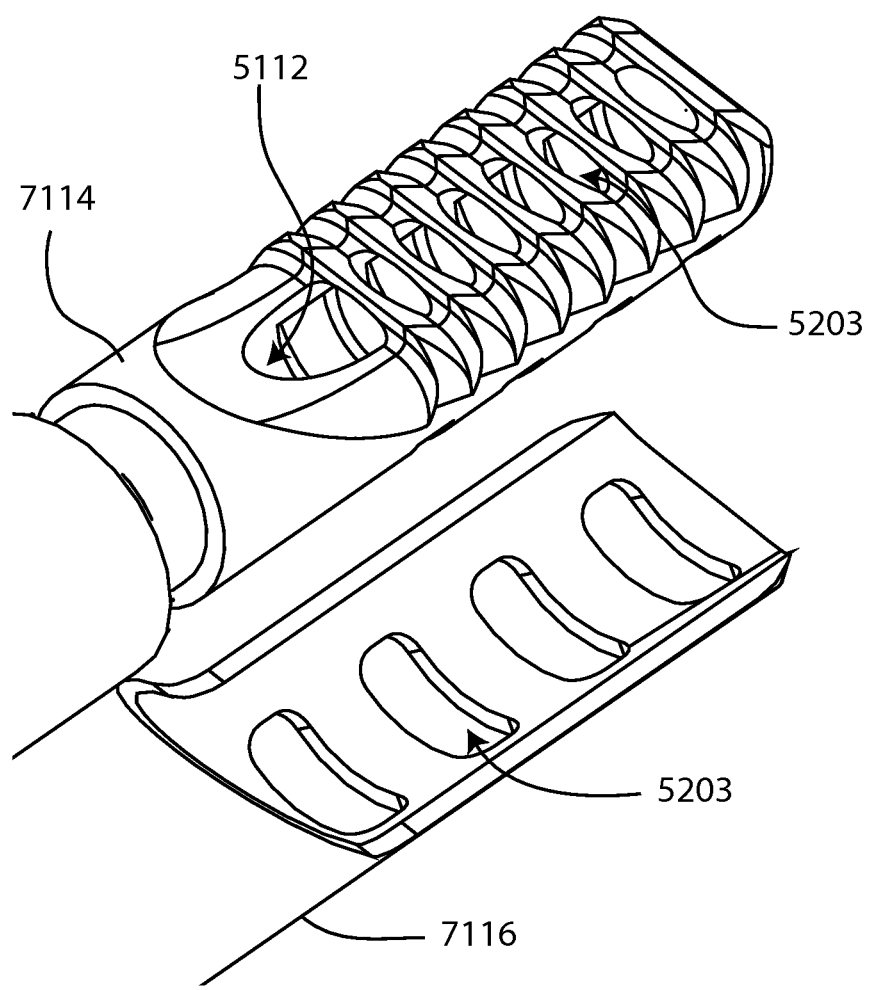
FIG. 71D is another isometric exploded view of the working member of FIG. 71A.
Figure 72A:
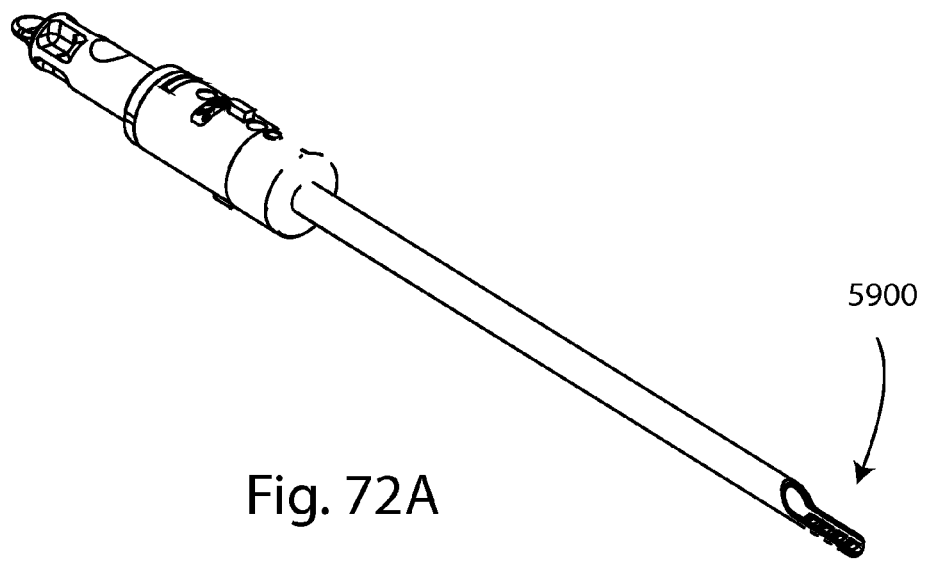
FIG. 72A is an isometric view of a reciprocating surgical instrument with a low profile enclosed shaver on the distal end of the surgical instrument.
Figure 72B:
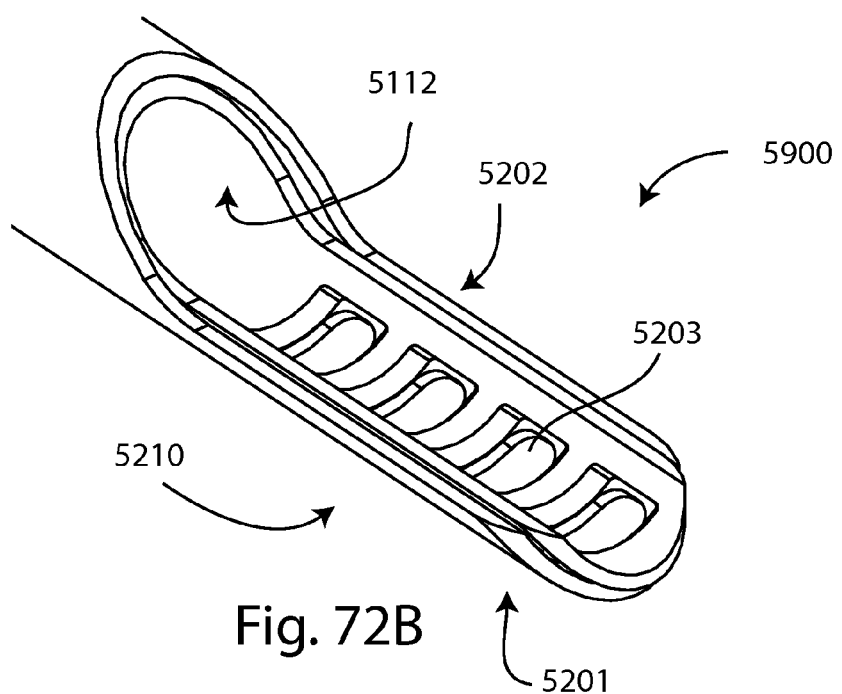
FIG. 72B is an enlarged view of the low profile enclosed shaver on the distal end of the surgical instrument of FIG. 72A.
Figure 72C:
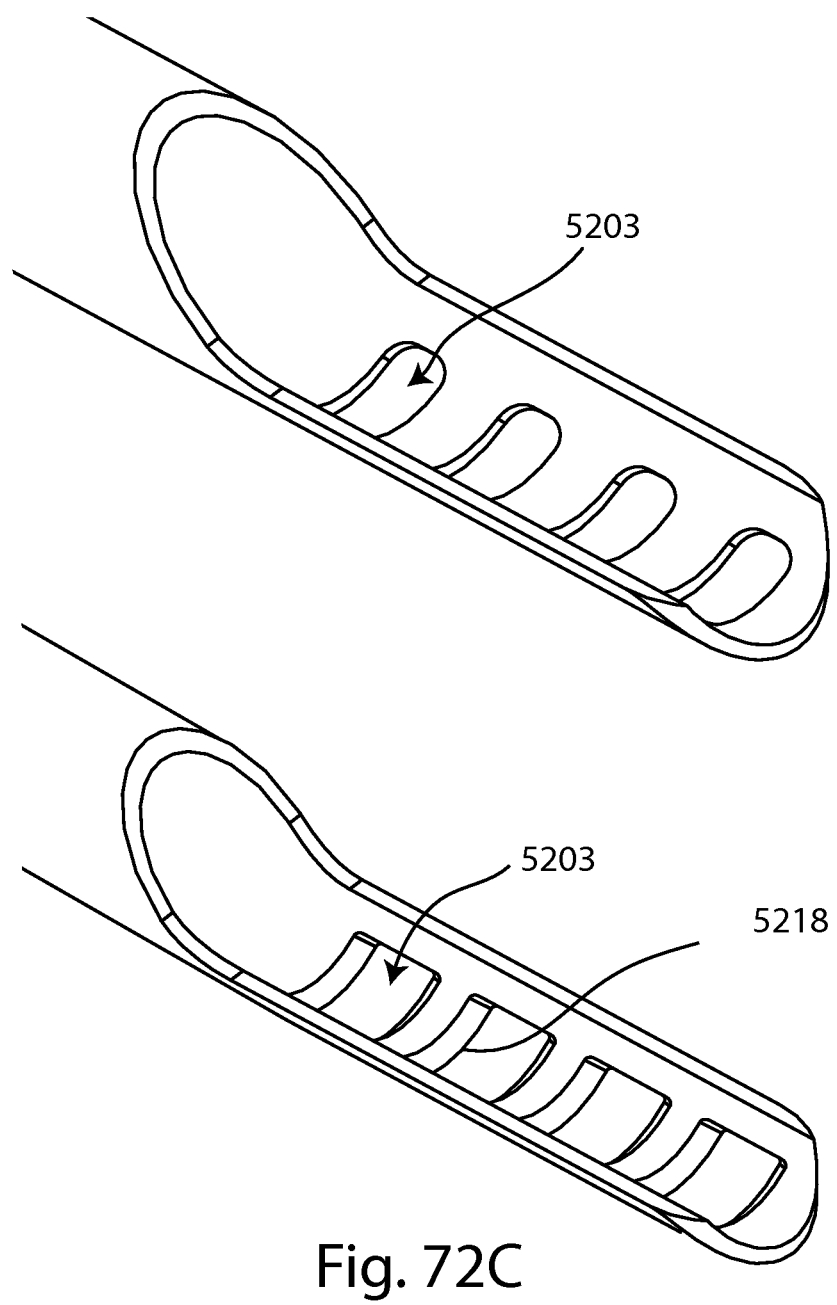
FIG. 72C is an isometric exploded view of the working member of FIG. 72A.
Figure 72D:
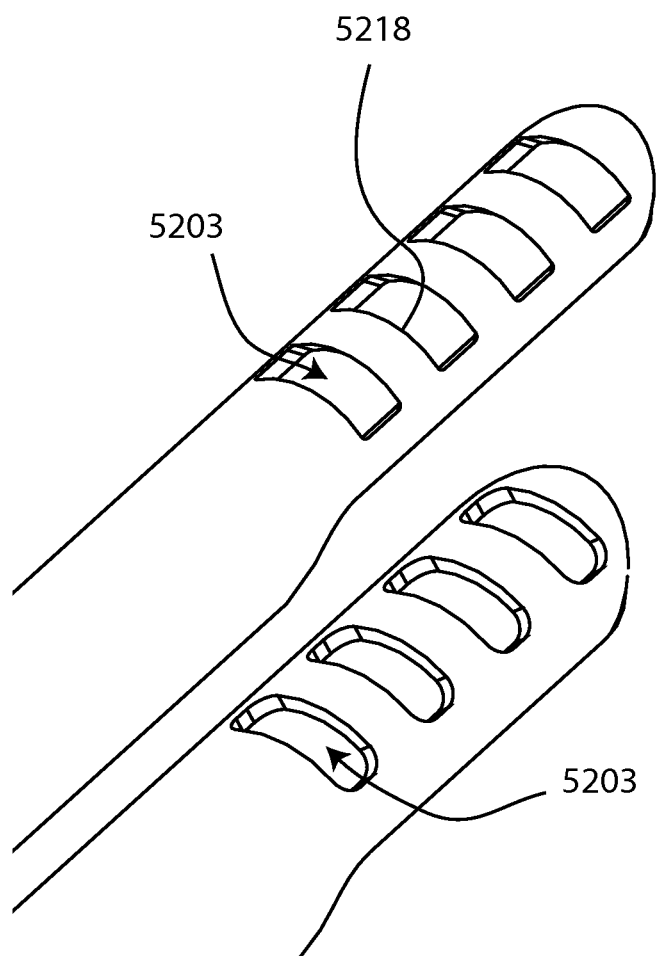
FIG. 72D is another isometric exploded view of the working member of FIG. 72A.
Figure 73A:
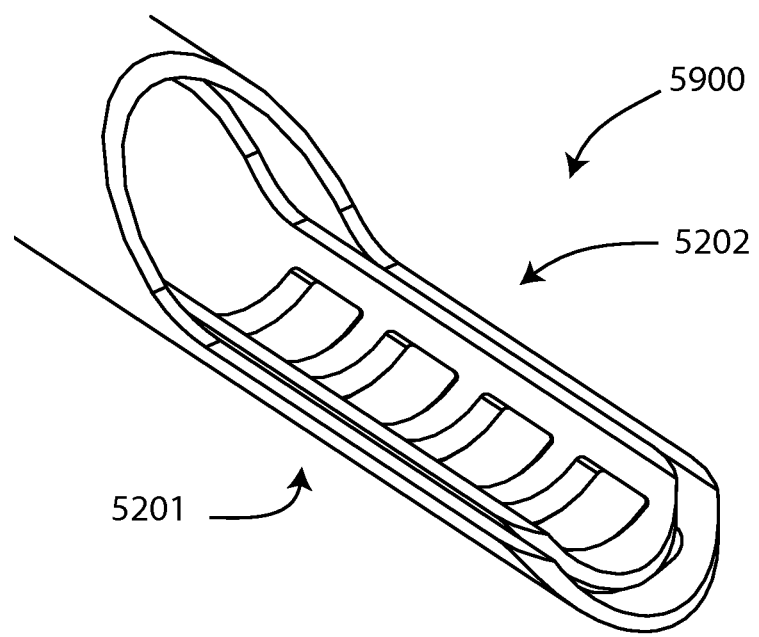
FIG. 73A is an isometric view of the enclosed shaver of FIG. 72A with the shaving blade in the retracted position.
Figure 73B:
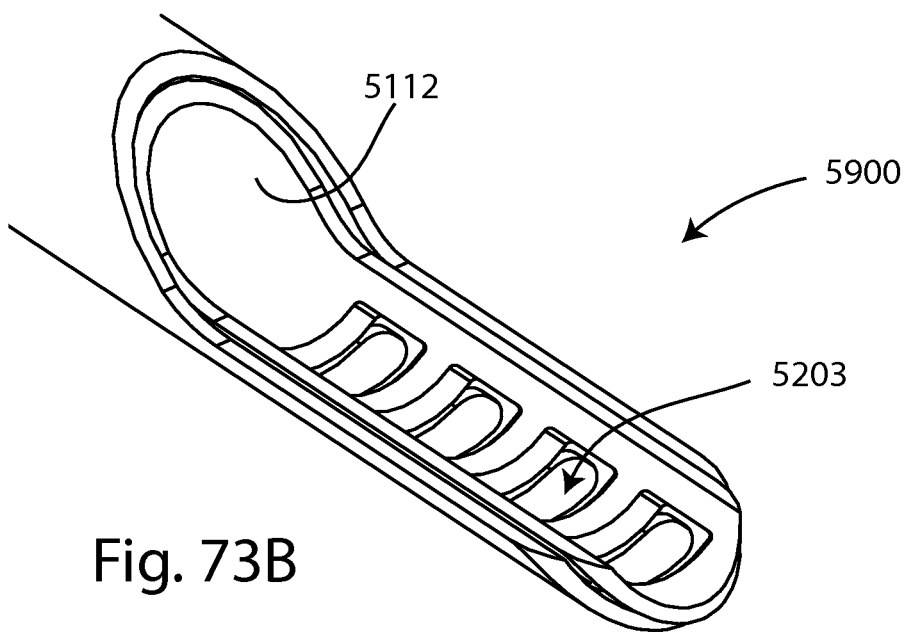
FIG. 73B is an isometric view of the enclosed shaver FIG.
Figure 73C:
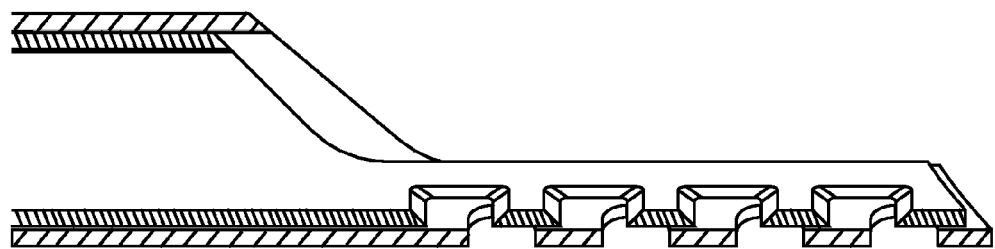
FIG. 73C is an enlarged longitudinal cross sectional view of the enclosed shaver of FIG. 72A.
Figure 74A:
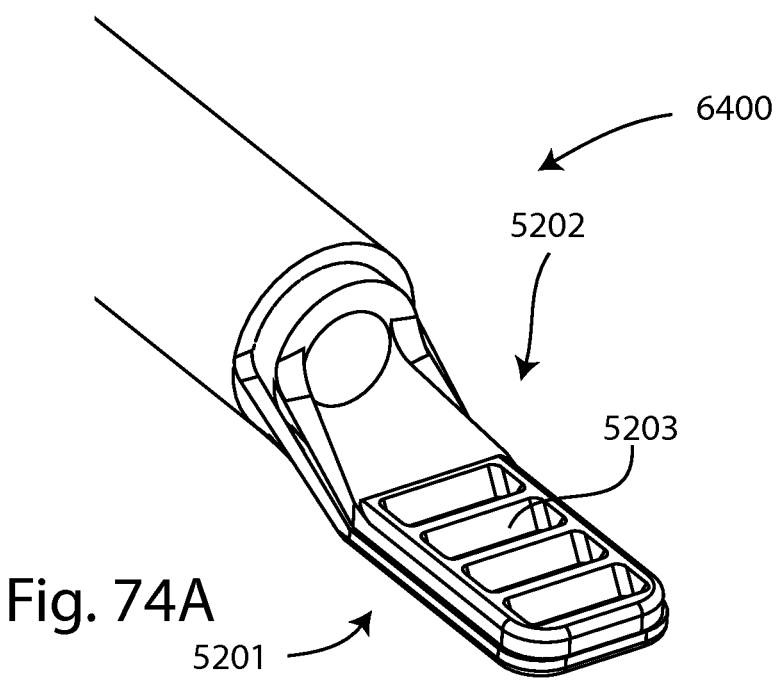
FIG. 74A is an isometric view of another example of the shaver with the blade in the retracted position in accordance with the present disclosure.
Figure 74B:
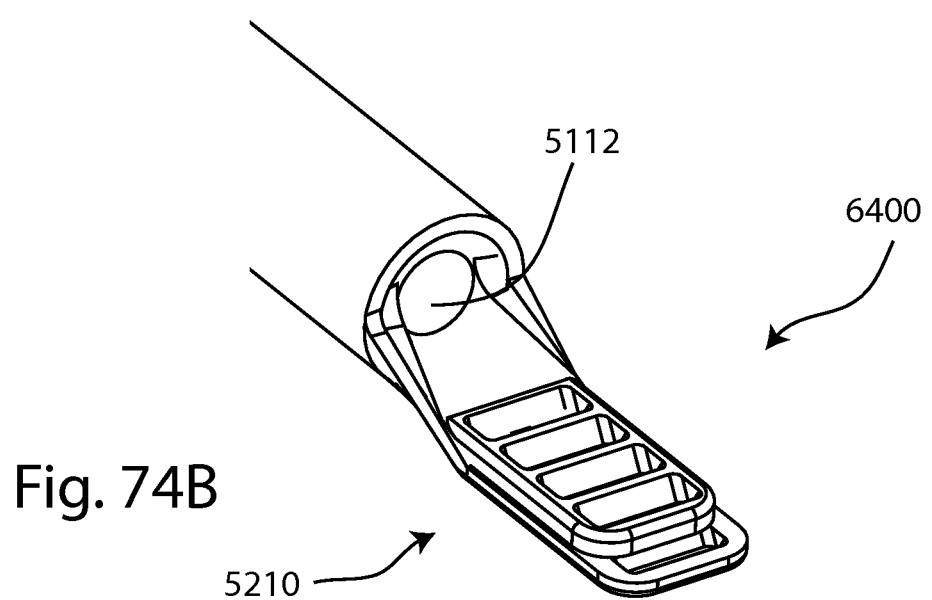
FIG. 74B is another isometric view of the shaver of FIG. 74A with the blade in the extended position.
Figure 74C:
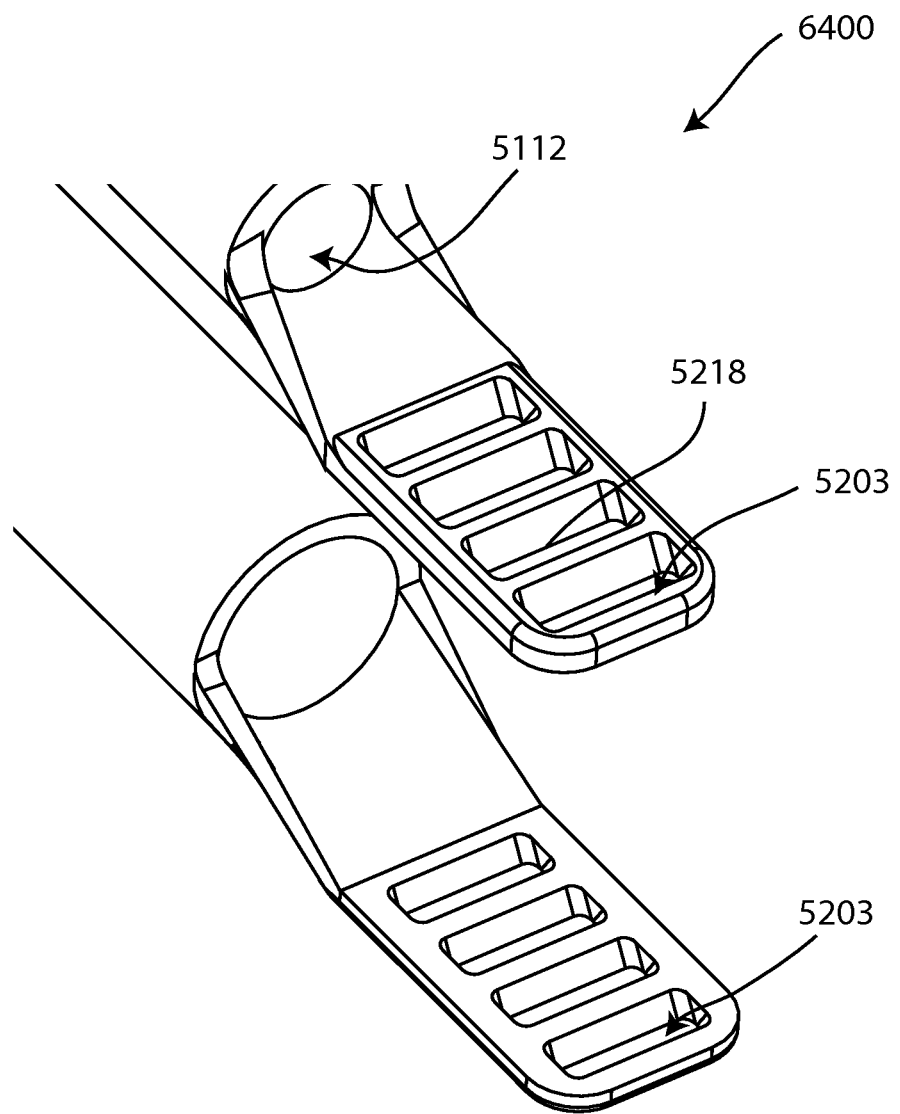
FIG. 74C is an isometric exploded view of the working member of FIG. 74A.
Figure 74D:
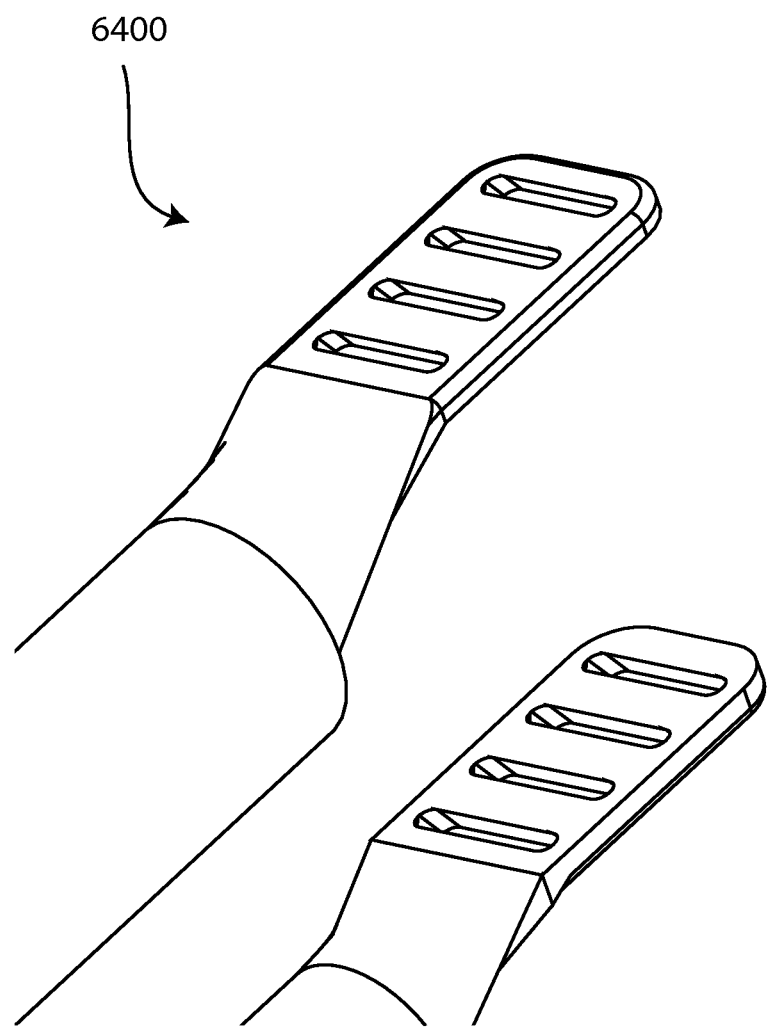
FIG. 74D is another isometric exploded view of the working member of FIG. 74A.

Referring now to FIGS. 70A-70C, a reciprocating surgical instrument 6100 is shown with a saw shaped working end 5700, or head. The saw shaped working end 5700 can have a plurality of teeth 5204 or cutting edges arranged in a plurality of rows. The working end 5700 can also have a suction port 5112 to remove resected tissues.

Referring now to FIGS. 71A-71D, a tissue removal member or working end 5800 is shown having a shaver working surface 5210 and a rasp working surface 5212 opposite the shaver working surface 5210. The shaver working surface 5210 includes a stationary shaft 7116 with one or more apertures or windows 5214 formed in the stationary shaft 7116. The moving portion 5216 reciprocates back and forth causing blade surfaces 5218 or cutting edges to resect any tissue that enters into the windows 5214. The shaver working surface 5210 can be useful for chondroplasty operations to correct conditions such as chondromalacia.

FIGS. 72A-74D include various embodiments of low profile shaver tissue removal members or working ends 5900, 6400 which do not include a rasp head on the surface opposite the shaver surface 5210. This allows these shaver heads to fit into tighter spaces without damaging the surrounding tissue which is desirable in joint operations where there is little room to maneuver the shaver to perform a chondroplasty. In these examples, the shaver blade reciprocates back and forth allowing tissue to enter through the apertures formed within the stationary shaft in a first position and then cutting the tissue as the blade moves toward a second position. Each of the shavers disclosed herein may include suction ports to remove the resected tissue once it has been removed by the shaver. Each of the shavers disclosed herein may have a convex, concave, and/or flat working surface, or combinations thereof.

Figure 75A:
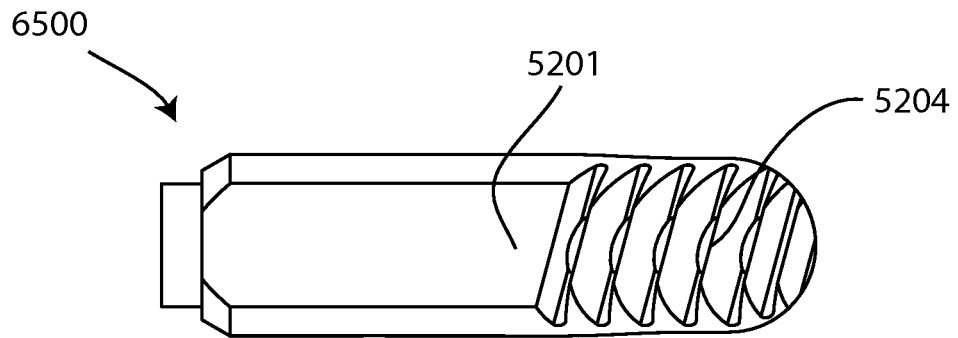
FIG. 75A is a bottom view of yet another tissue removal member according to another example of the present disclosure.
Figure 75B:
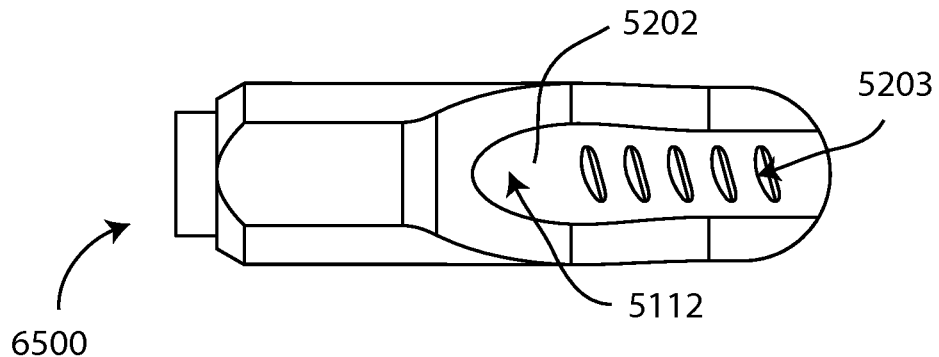
FIG. 75B is a top view of the tissue removal member of FIG. 75A.
Figure 75C:
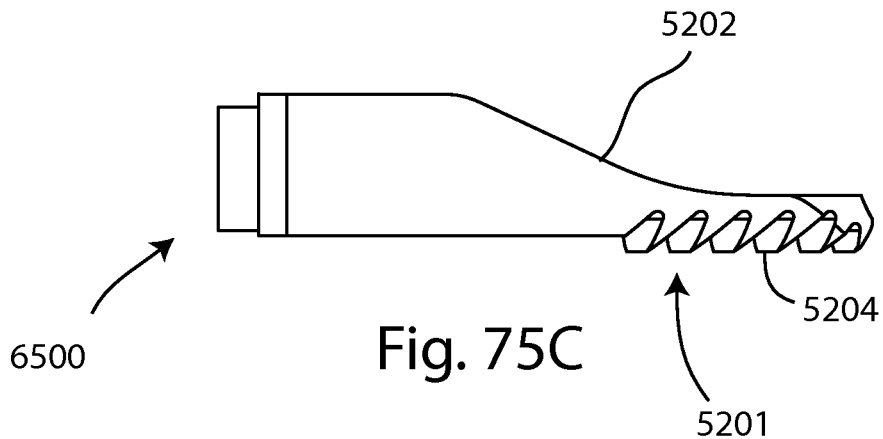
FIG. 75C is a side view of the tissue removal member of FIG. 75A.
Figure 75D:
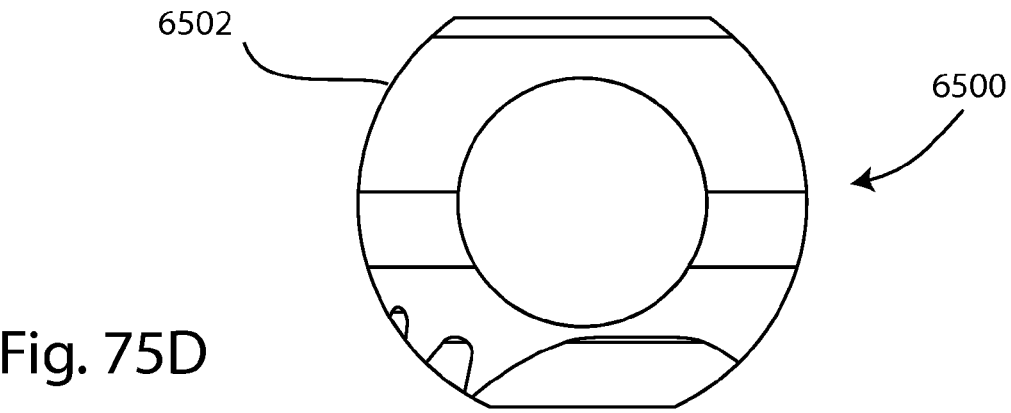
FIG. 75D is a right view of the tissue removal member of FIG. 75A.
Figure 75E:
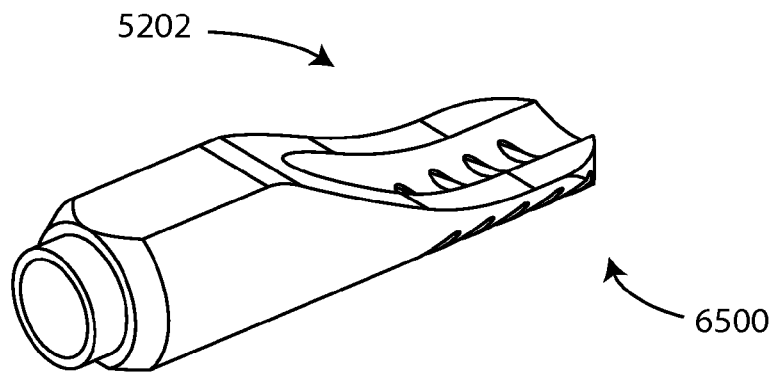
FIG. 75E is an isometric view of the tissue removal member of FIG. 75A.
Figure 75F:
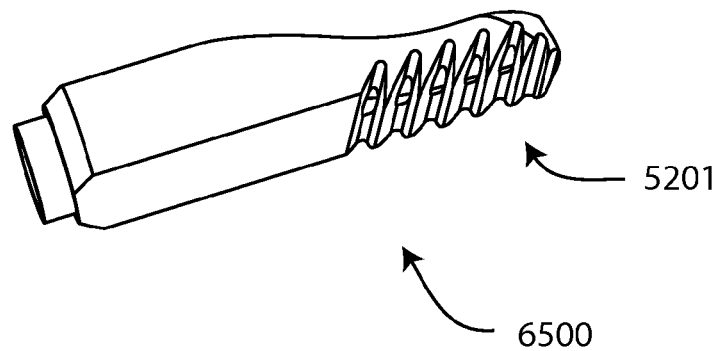
FIG. 75F is another isometric view of the tissue removal member of FIG. 75A.

Referring to FIGS. 75A-75F, a working member 6500 or rasp head may be fabricated from round cannulated or tubular stock with a sequence of external material removal operations, as may be appreciated best in FIG. 75C. Rasp head 6500 is bounded by an outside diameter 6502, which may be the outside diameter of a round bar or tube stock. The external material removal operations may include turning, milling, grinding, and the like.

In other embodiments (not shown) the stationary outer shaft can be extended over the shaver area to increase suction forces directly above the apertures where the tissue is cut.

One way to view the teachings set forth above is to characterize certain structures as tissue removal means. In the various embodiments set forth above the tissue removal means can be said to be element 140 as shown in FIGS. 3A and 3B, or element 272 in FIGS. 11A and 11B, or element 292 in FIGS. 13A and 13B, or element 302 in FIGS. 14A and 14B, or element 312 in FIGS. 15A and 15B, or element 322 in FIGS. 16A and 16B, or element 332 in FIGS. 17A and 17B, or element 354 in FIGS. 18A and 18B, or element 411 in FIGS. 19A-22, or element 509 in FIG. 27, or the tissue removal surfaces seen in FIGS. 23A, 23C, 24, 25A, 25B, 26A, or element 600 in FIGS. 34A-34B, or element 620 in FIGS. 35A-35C, or element 740 in FIGS. 37A-37C, or element 760 in FIGS. 38A-38C, or element 780 in FIGS. 39A-39C, or element 800 in FIGS. 40A-40C, or element 820 in FIGS. 41A-41C, or element 840 in FIGS. 42A and 42B, or element 860 in FIGS. 43A and 43B, or element 880 in FIGS. 44A and 44B, or element 900 in FIGS. 45A-45D, or element 920 in FIGS. 46A and 46B, or element 940 in FIGS. 47A and 47B, or element 960 in FIGS. 48A-48C, or element 980 in FIGS. 49A and 49B. Other tissue removal means are contemplated within the scope of the invention, including but not limited to tissue removal surfaces comprising teeth, ridges, or sharpened or roughened surfaces.

Certain aspects of the teaching set forth above can be characterized as motion conversion means for converting rotary motion of a tissue removal member to reciprocal motion. Structure for the motion conversion means is found in at least FIGS. 8 and 9 in elements 118 and 120, and in FIGS. 30 and 31 in elements 526 and 524. Other motion conversion means are contemplated within the scope of the invention, including but not limited to a rotating hub or sluff chamber and a fixed housing, a cam and a cam follower, and complementary cam and cam follower surfaces.

Certain aspects of the teaching set forth above can be characterized as soft tissue ablation or coagulation means for destroying or coagulating soft tissue. Structure for the soft tissue ablation or coagulation means is found in at least FIGS. 19A-24, and FIGS. 26A-26C in RF ablation electrodes 422, 442 and 462. Other soft tissue ablation means are contemplated within the scope of the invention, including but not limited to other RF current emitting elements, electrical energy emitting elements, heat emitting elements, microwave emitting elements, and other energy emitting elements capable of selectively destroying or coagulating soft tissue.

Certain aspects of the teaching set forth above can be characterized as means for suction. Structure for suction means is found in at least FIGS. 3-9 in elements 112, 148, 166, 178, and 238. Another structure for suction means is also found in at least FIGS. 27, 30 and 31 in elements 512, 515, 540 and 538, and in FIGS. 34, 35, 36, 37, 38, 39, 40, 41, 42, 43, 44, 45, 46, 47, 48, 49 in elements 606, 634, 712, 702, 744, 768, 788, 808, 828, 846, 868, 890, 908, 928, 948, 968, and 990. Other suction means are contemplated within the scope of the invention, for example any suction opening found on any of the rasp or cutting heads disclosed herein may form a suction pathway in combination with suction pathway elements of the any inner sleeves and hubs disclosed herein.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term or in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features.

Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, any rasping, cutting, or shaving head may be combined with any handle portion or driving hub configuration. Similarly, suction, RF ablation, infusion, and/or imaging capability may be included with any rasping and/or shaving system disclosed herein. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A tissue removal device comprising:
   a first cam, wherein the first cam comprises an undulating cam surface;
   a hub axially fixed to the first cam, wherein the hub is rotatable relative to the first cam about an axis of rotation;
   a second cam between the hub and the first cam, wherein the second cam is rotationally fixed to the hub, wherein the second cam is axially slidable relative to the hub along the axis of rotation, wherein the second cam comprises an undulating cam surface;
   a translation member comprising a distal working member and an opposite proximal portion, wherein the translation member is rotationally fixed to the first cam, wherein the translation member is axially slidable relative to the first cam along the axis of rotation, wherein the translation member is axially fixed relative to the second cam, wherein the translation member is rotatable relative to the second cam about the axis of rotation; and,
   wherein, during rotation of the hub about the axis of rotation, the second cam rotates with the hub relative to the first cam, wherein the cam surface of the first cam and the cam surface of the second cam cooperate to convert rotation of the hub and second cam to reciprocating translation of the second cam and the translation member relative to the first cam along the axis of rotation, and the second cam and the translation member thereby undergo reciprocal translation relative to the first cam along the axis of rotation.

2. The system of claim 1, wherein the cam surface of the first cam comprises alternating high points and low points, wherein the high points protrude farther toward the second cam than do the low points, wherein the cam surface of the second cam comprises alternating high points and low points, wherein the high points protrude farther toward the first cam than do the low points.

3. The system of claim 1, comprising at least one spherical ball bearing between the cam surface of the first cam and the cam surface of the second cam.

4. The system of claim 3, wherein at least one of the cam surface of the first cam and the cam surface of the second cam is concave to complement the at least one ball bearing.

5. The system of claim 1, comprising a housing rigidly fixed to the first cam, wherein the housing is axially fixed relative to the hub.

6. The system of claim 1, wherein the hub comprises at least one driving surface extending parallel to the axis of rotation, wherein the second cam comprises at least one drive surface extending parallel to the axis of rotation, wherein the driving surface and the drive surface form an interface through which rotational forces are transmitted from the hub to the second cam.

7. The system of claim 1, wherein the working member comprises a tissue removal member.

8. A reciprocating instrument for use with a powered rotary handpiece, the reciprocating instrument comprising:
   a tissue removal member comprising a top surface, an opposite working surface, and an aperture, wherein the working surface comprises a cutting edge, wherein the aperture extends through the tissue removal member between the top and working surfaces;
   a hub comprising a handpiece connection feature connectable to the handpiece;
   a first cam, wherein the first cam comprises a cam surface that comprises alternating high points and low points;
   a second cam rotationally fixed to the hub and axially fixed to the tissue removal member, wherein the second cam comprises a cam surface with alternating high points and low points, wherein the high points protrude farther toward the first cam than do the low points;
   wherein the high points of the cam surface of the first cam protrude farther toward the second cam than do the low points; and,
   wherein, when the handpiece connection feature is connected to the handpiece and the handpiece is powered, the hub and the second cam rotate relative to the tissue removal member about an axis of rotation, and the second cam and tissue removal member reciprocally translate relative to the hub along the axis of rotation.

9. The reciprocating instrument of claim 8,
   wherein the first cam is rigidly fixed to the hub; and,
   wherein, when the handpiece connection feature is connected to the handpiece and the handpiece is powered, the second cam and the first cam cooperate to cause the second cam and tissue removal member to reciprocally translate relative to the hub along the axis of rotation.

10. The reciprocating instrument of claim 9, comprising:
    a housing rigidly fixed to the first cam, wherein the housing is axially fixed relative to the hub, and wherein the second cam is between the hub and the first cam.

11. The reciprocating instrument of claim 8, wherein the working surface comprises multiple cutting edges.

12. The reciprocating instrument of claim 8, wherein the tissue removal member comprises multiple apertures extending through the tissue removal member between the top and working surfaces.

13. The reciprocating instrument of claim 8, wherein the tissue removal member comprises a suction port near the cutting edge.

14. A reciprocating instrument for use with a powered rotary handpiece, the reciprocating instrument comprising:
    a tissue removal member comprising a cutting edge;
    a hub comprising a handpiece connection feature connectable to the handpiece;
    a first cam axially fixed to the hub, wherein the first cam comprises a cam surface; and
    a second cam rotationally fixed to the hub and axially fixed to the tissue removal member, wherein the second cam comprises a cam surface;
    at least one spherical ball bearing between the cam surface of the first cam and the cam surface of the second cam; and,
    wherein, when the handpiece connection feature is connected to the handpiece and the handpiece is powered, the hub and the second cam rotate relative to the tissue removal member about an axis of rotation, and the second cam and the first cam cooperate to cause the second cam and the tissue removal member to reciprocally translate relative to the hub and the first cam along the axis of rotation.

15. The reciprocating instrument of claim 14, comprising: a housing rigidly fixed to the first cam, wherein the housing is axially fixed to the hub, and wherein the second cam is between the hub and the first cam.

16. The reciprocating instrument of claim 14, wherein the cam surface of the first cam undulates, wherein the cam surface of the second cam undulates, wherein the cam surface of the first cam and the cam surface of the second cam cooperate to cause the second cam and the tissue removal member to reciprocally translate relative to the hub and the first cam along the axis of rotation.

17. The system of claim 14, wherein at least one of the cam surface of the first cam and the cam surface of the second cam is concave to complement the at least one ball bearing.

18. The system of claim 14, wherein the hub comprises at least one driving surface extending parallel to the axis of rotation, wherein the second cam comprises at least one drive surface extending parallel to the axis of rotation, and wherein the driving surface and the drive surface form an interface through which rotational forces are transmitted from the hub to the second cam.

* * * * *